(12) United States Patent
Johnson et al.

(10) Patent No.: US 10,683,387 B2
(45) Date of Patent: Jun. 16, 2020

(54) BOTTLEBRUSH COPOLYMERS AND USES THEREOF

(71) Applicant: Massachusetts Institute of Technology, Cambridge, MA (US)

(72) Inventors: Jeremiah A. Johnson, Boston, MA (US); Qixian Chen, Somerville, MA (US); Farrukh Vohidov, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 125 days.

(21) Appl. No.: 15/725,036

(22) Filed: Oct. 4, 2017

(65) Prior Publication Data

US 2018/0094099 A1     Apr. 5, 2018

Related U.S. Application Data

(60) Provisional application No. 62/404,098, filed on Oct. 4, 2016.

(51) Int. Cl.
| | |
|---|---|
| C08G 61/02 | (2006.01) |
| C08G 61/08 | (2006.01) |
| C08G 61/12 | (2006.01) |
| A61K 9/06 | (2006.01) |
| A61K 47/30 | (2006.01) |
| A61K 9/14 | (2006.01) |
| A61K 31/192 | (2006.01) |
| A61K 31/5383 | (2006.01) |
| A61K 31/573 | (2006.01) |

(52) U.S. Cl.
CPC .............. C08G 61/02 (2013.01); A61K 9/06 (2013.01); A61K 9/146 (2013.01); A61K 31/192 (2013.01); A61K 31/5383 (2013.01); A61K 31/573 (2013.01); A61K 47/30 (2013.01); C08G 61/08 (2013.01); C08G 61/12 (2013.01); *C08G 2210/00* (2013.01); *C08G 2261/126* (2013.01); *C08G 2261/132* (2013.01); *C08G 2261/143* (2013.01); *C08G 2261/3324* (2013.01); *C08G 2261/354* (2013.01); *C08G 2261/418* (2013.01); *C08G 2261/75* (2013.01); *C08G 2261/90* (2013.01)

(58) Field of Classification Search
None
See application file for complete search history.

(56) References Cited

U.S. PATENT DOCUMENTS

| | | | |
|---|---|---|---|
| 4,359,425 A | 11/1982 | Totani et al. | |
| 5,811,515 A | 9/1998 | Grubbs et al. | |
| 8,067,505 B2 | 11/2011 | Harris et al. | |
| 9,381,253 B2 | 7/2016 | Johnson et al. | |
| 9,447,129 B2 | 9/2016 | Johnson et al. | |
| 10,023,536 B2 | 7/2018 | Johnson et al. | |
| 10,105,449 B2 | 10/2018 | Johnson et al. | |
| 10,159,749 B2 | 12/2018 | Johnson et al. | |
| 2002/0183473 A1 | 12/2002 | Matyjaszewski et al. | |
| 2002/0198328 A1* | 12/2002 | L'alloret | A61K 8/91 525/326.7 |
| 2003/0065023 A1 | 4/2003 | Swindell et al. | |
| 2005/0109976 A1 | 5/2005 | Fuchs et al. | |
| 2011/0300219 A1 | 12/2011 | Lippard et al. | |
| 2013/0296491 A1 | 11/2013 | Xia et al. | |
| 2013/0324666 A1 | 12/2013 | Yan et al. | |
| 2014/0308234 A1 | 4/2014 | Johnson et al. | |
| 2014/0142249 A1 | 5/2014 | Cho et al. | |
| 2015/0225438 A1 | 8/2015 | Johnson et al. | |
| 2016/0024246 A1 | 1/2016 | Mahanthappa et al. | |
| 2016/0289392 A1 | 10/2016 | Grubbs et al. | |
| 2016/0296631 A1 | 10/2016 | Johnson et al. | |
| 2016/0361702 A1 | 12/2016 | Cohen et al. | |

(Continued)

FOREIGN PATENT DOCUMENTS

| | | |
|---|---|---|
| CN | 101412792 A | 4/2009 |
| KR | 20120113694 A | 10/2012 |

(Continued)

OTHER PUBLICATIONS

International Search Report and Written Opinion for PCT/US2017/055145, dated Jan. 23, 2018.
Invitation to Pay Additional Fees for PCT/US2017/044259, dated Nov. 8, 2017.
International Search Report and Written Opinion for PCT/US2017/044259, dated Jan. 9, 2018.
Bolton et al., Synthesis and Melt Self-Assembly of PS-PMMA-PLA Triblock Bottlebrush Copolymers. Macromolecules, 2014;47(9):2864-74. DOI: 10.1021/ma500625k.
Hoogenboom et al., l-Lactide Polymerization Utilizing a Hydroxy-Functionalized 3,6-Bis(2-pyridyl)pyridazine as Supramolecular (Co)initiator: Construction of Polymeric [2×2] Grids. Macromolecules, 2003;36(13):4743-9. DOI: 10.1021/ma034119e.

(Continued)

*Primary Examiner* — Ana L. Woodward
(74) *Attorney, Agent, or Firm* — Wolf, Greenfield & Sacks, P.C.

(57) ABSTRACT

Materials (e.g., particles, hydrogels) that provide extended release of one or more therapeutic agents are useful platforms for drug delivery. In part, the present invention relates to new triblock (ABC) bottlebrush copolymers which can be used in the formulation of particles and hydrogels for the extended release of therapeutic agents. In certain embodiments, the triblock bottlebrush copolymers, particles, and hydrogels described herein are thermally-responsive and gel at physiological temperature (e.g., upon administration to a subject), providing injectable and/or implantable gels which can be used for extended release drug delivery. The present invention also provides methods for extended release drug delivery, and methods of treating and/or preventing a disease or conditions in a subject, using the inventive copolymers, particles, and hydrogels. In addition, the present invention provides methods of preparing the triblock bottlebrush copolymers described herein.

51 Claims, 27 Drawing Sheets

(56) References Cited

U.S. PATENT DOCUMENTS

| | | | |
|---|---|---|---|
| 2017/0000909 | A1 | 1/2017 | Gianneschi et al. |
| 2017/0073311 | A1 | 3/2017 | Johnson et al. |
| 2018/0030213 | A1 | 2/2018 | Johnson et al. |
| 2018/0036415 | A9 | 2/2018 | Johnson et al. |
| 2018/0094099 | A1 | 4/2018 | Johnson et al. |
| 2018/0258233 | A9 | 9/2018 | Johnson et al. |
| 2019/0038751 | A1 | 2/2019 | Johnson et al. |
| 2019/0038782 | A1 | 2/2019 | Johnson et al. |
| 2019/0054187 | A1 | 2/2019 | Johnson et al. |

FOREIGN PATENT DOCUMENTS

| | | | |
|---|---|---|---|
| WO | WO 2010/047765 | A1 | 4/2010 |
| WO | WO 2013/169739 | A1 | 11/2013 |
| WO | WO 2014/169073 | A1 | 10/2014 |
| WO | WO 2016/023036 | A1 | 2/2016 |

OTHER PUBLICATIONS

Hu et al., Enhancing Gelation of Doubly Thermosensitive Hydrophilic ABC Linear Triblock Copolymers in Water by Thermoresponsive Hairy Nanoparticles. Macromolecules, 2016;49(15):5502-13. DOI: 10.1021/acs.macromol.6b01156.
Verduzco et al., Structure, function, self-assembly, and applications of bottlebrush copolymers. Chem. Soc. Rev., 2015;44:2405-20.
Zheng et al., Construction of Smart Supramolecular Polymeric Hydrogels Cross-linked by Discrete Organoplatinum(II) Metallacycles via Post-Assembly Polymerization. J. Am. Chem. Soc., 2016;138(14):4927-37. DOI: 10.1021/jacs.6b01089.
Extended European Search Report for EP 14782253.0, dated Nov. 11, 2016.
International Preliminary Report on Patentability for PCT/US2014/033554, dated Oct. 22, 2015.
International Search Report and Written Opinion for PCT/US2014/033554, dated Aug. 29, 2014.
International Search Report and Written Opinion for PCT/US2015/015032, dated May 8, 2015.
International Preliminary Report on Patentability for Application No. PCT/US2015/015032, dated Aug. 18, 2016.
International Search Report for PCT/US2017/036447, dated Sep. 7, 2017.
International Preliminary Report on Patentability for Application No. PCT/US2017/036447 dated Dec. 20, 2018.
International Preliminary Report on Patentability for PCT/US2017/055145, dated Apr. 18, 2019.
International Search Report and Written Opinion for PCT/US2017/064784, dated Mar. 1, 2018.
International Preliminary Report on Patentability for Application No. PCT/US2017/48641 dated Mar. 7, 2019.
International Preliminary Report on Patentability for PCT/US2017/044259, dated Feb. 7, 2019.
International Search Report and Written Opinion for PCT/US2018/040488, dated Oct. 15, 2018.
International Search Report and Written Opinion for PCT/US2018/040494, dated Oct. 10, 2018.
International Search Report and Written Opinion for Application No. PCT/US2018/040496 dated Jan. 14, 2019.
Ahn et al., Two-photon fluorescence microscopy imaging of cellular oxidative stress using profluorescent nitroxides. J Am Chem Soc. Mar. 14, 2012;134(10):4721-30. doi: 10.1021/ja210315x. Epub Mar. 1, 2012.
Aime et al., Lanthanide(III) chelates for NMR biomedical applications. Chem. Soc. Rev., 1998;27:19-29.
Aime et al., Pushing the sensitivity envelope of lanthanide-based magnetic resonance imaging (MRI) contrast agents for molecular imaging applications. Acc Chem Res. Jul. 21, 2009;42(7):822-31. doi: 10.1021/ar800192p.
Alge et al., Synthetically tractable click hydrogels for three-dimensional cell culture formed using tetrazine-norbornene chemistry. Biomacromolecules. Apr. 8, 2013;14(4):949-53. doi: 10.1021/bm4000508. Epub Mar. 8, 2013.
Allen et al., Chemically crosslinked isoreticular metal-organic frameworks. Chem Commun (Camb). Apr. 21, 2013;49(31):3200-2. doi: 10.1039/c3cc40635k. Epub Mar. 14, 2013.
Allen et al., Exploration of chemically cross-linked metal-organic frameworks. Inorg Chem. Jul. 7, 2014;53(13):7014-9. doi: 10.1021/ic500951b. Epub Jun. 19, 2014.
Altintas et al., ATRP-based polymers with modular ligation points under thermal and thermomechanical stress. Polym. Chem., Feb. 2015;6:2854-68.
Altintas et al., Constructing star polymersvia modular ligation strategies. Polym. Chem., 2012;3:34-45. DOI: 10.1039/C1PY00249J.
Amouri et al., Host-guest interactions: design strategy and structure of an unusual cobalt cage that encapsulates a tetrafluoroborate anion. Angew Chem Int Ed Engl. Jul. 18, 2005;44(29):4543-6.
Anderson, Late Transition Metal Complexes of Pentafluorophenylphosphino-Pincer Ligands. Doctoral Thesis. Victoria University of Wellington. 2012:ii, iii, 32.
Angelov et al., EPR and rheological study of hybrid interfaces in gold-clay-epoxy nanocomposites. Langmuir. Nov. 11, 2014;30(44):13411-21. doi: 10.1021/la503361k. Epub Oct. 30, 2014.
Angot et al., Living Radical Polymerization Immobilized on Wang Resins: Synthesis and Harvest of Narrow Polydispersity Poly(methacrylate)s. Macromolecules, 2001;34(4):768-774. DOI: 10.1021/ma0011690.
Anraku et al., Size-controlled long-circulating PICsome as a ruler to measure critical cut-off disposition size into normal and tumor tissues. Chem Commun (Camb). Jun. 7, 2011;47(21):6054-6. doi: 10.1039/c1cc11465d. Epub Apr. 26, 2011.
Arvizo et al., Modulating pharmacokinetics, tumor uptake and biodistribution by engineered nanoparticles. PLoS One. 2011;6(9):e24374. doi: 10.1371/journal.pone.0024374. Epub Sep. 13, 2011.
Aryal et al., Polymeric nanoparticles with precise ratiometric control over drug loading for combination therapy. Mol Pharm. Aug. 1, 2011;8(4):1401-7. doi: 10.1021/mp200243k. Epub Jul. 6, 2011.
Ayala et al., Hierarchical structure and porosity in UiO-66 polyMOFs. Chem Commun (Camb). Mar. 9, 2017;53(21):3058-3061. doi: 10.1039/c6cc10225e.
Bapat et al., Dynamic-covalent nanostructures prepared by Diels-Alder reactions of styrene-maleic anhydride-derived copolymers obtained by one-step cascade block copolymerization. Polym. Chem., 2012;3:3112-3120. DOI: 10.1039/C2PY20351K.
Bapat et al., Redox-Responsive Dynamic-Covalent Assemblies: Stars and Miktoarm Stars. Macromolecules, 2013;46(6):2188-2198. DOI: 10.1021/ma400169m.
Barbour et al., An intermolecular (H2O)10 cluster in a solid-state supramolecular complex. Nature. 1998;393(6686): 671-673.
Barner et al., Synthesis of core-shell poly(divinylbenzene) microspheres via reversible addition fragmentation chain transfer graft polymerization of styrene. J. Polym. Sci. A Polym. Chem., 42: 5067-5076. doi:10.1002/pola.20328.
Barnes et al., Using an RNAi Signature Assay to Guide the Design of Three-Drug-Conjugated Nanoparticles with Validated Mechanisms, In Vivo Efficacy, and Low Toxicity. J Am Chem Soc. Sep. 28, 2016;138(38):12494-501. doi: 10.1021/jacs.6b06321. Epub Sep. 14, 2016.
Barrett et al., pH-Based Regulation of Hydrogel Mechanical Properties Through Mussel-Inspired Chemistry and Processing. Advanced Functional Materials. Mar. 6, 2013;23(9):1111-1119.
Bar-Shir et al., Single 19F Probe for Simultaneous Detection of Multiple Metal Ions Using miCEST MRI. J. Am. Chem. Soc., 2015;137(1):78-81. DOI: 10.1021/ja511313k.
Bates et al., Block Copolymers—Designer Soft Materials. Physics Today 1999;52(2):32.
Bates et al., Multiblock polymers: panacea or Pandora's box? Science. Apr. 27, 2012;336(6080):434-40. doi: 10.1126/science.1215368.

(56) References Cited

OTHER PUBLICATIONS

Bates et al., Polymer-polymer phase behavior. Science. Feb. 22, 1991;251(4996):898-905.

Beck et al., Multistimuli, multiresponsive metallo-supramolecular polymers. J Am Chem Soc. Nov. 19, 2003;125(46):13922-3.

Bender et al., Site-isolated luminescent europium complexes with polyester macroligands: metal-centered heteroarm stars and nanoscale assemblies with labile block junctions. J Am Chem Soc. Jul. 24, 2002;124(29):8526-7.

Binauld et al., Precise Synthesis of Molecularly Defined Oligomers and Polymers by Orthogonal Iterative Divergent/Convergent Approaches. Macromol. Rapid Commun., 32: 147-168. doi:10.1002/marc.201000548.

Blencowe et al., Core cross-linked star polymers via controlled radical polymerisation. Polymer Jan. 2009;50(1):5-32.

Blinco et al., Profluorescent Nitroxides as Sensitive Probes of Oxidative Change and Free Radical Reactions. Australian Journal of Chemistry 2010;64(4):373-389. https://doi.org/10.1071/CH10442.

Boase et al., Molecular imaging with polymers. Polym. Chem., 2012,3, 1384-1389. DOI: 10.1039/C2PY20132A.

Bobko et al., Reversible reduction of nitroxides to hydroxylamines: roles for ascorbate and glutathione. Free Radic Biol Med. Feb. 1, 2007;42(3):404-12. Epub Nov. 10, 2006.

Brasch et al., Work in progress: nuclear magnetic resonance study of a paramagnetic nitroxide contrast agent for enhancement of renal structures in experimental animals. Radiology. Jun. 1983;147(3):773-9.

Brasch, Work in progress: methods of contrast enhancement for NMR imaging and potential applications. A subject review. Radiology. Jun. 1983;147(3):781-8.

Brown et al., Halide-induced supramolecular ligand rearrangement. J Am Chem Soc. Nov. 10, 2004;126(44):14316-7.

Brummelhuis et al., Stimuli-responsive star polymers through thiol-yne core functionalization/crosslinking of block copolymer micelles. Polym. Chem., 2011;2:1180-1184. DOI: 10.1039/C1PY00002K.

Budil et al., Nonlinear-Least-Squares Analysis of Slow-Motion EPR Spectra in One and Two Dimensions Using a Modified Levenberg-Marquardt Algorithm. Elsevier. Journal of Magnetic Resonance, Series A. Jun. 1996;120(2):155-189.

Buerkle et al., Supramolecular gels formed from multi-component low molecular weight species. Chem Soc Rev. Sep. 21, 2012;41(18):6089-102. doi: 10.1039/c2cs35106d. Epub Jun. 7, 2012.

Bunzen et al., Self-assembly of M24L48 polyhedra based on empirical prediction. Angew Chem Int Ed Engl. Mar. 26, 2012;51(13):3161-3. doi: 10.1002/anie.201108731.

Burdynska et al., Synthesis of Star Polymers Using ARGET ATRP. Macromolecules, 2010;43(22):9227-9229. DOI: 10.1021/ma101971z.

Burnworth et al., Decoupling Optical Properties in Metallo-Supramolecular Poly (p-phenylene ethynylene)s. Macromolecules. 2008;41(6):2157-2163.

Burnworth et al., Optically healable supramolecular polymers. Nature. Apr. 21, 2011;472(7343):334-7. doi: 10.1038/nature09963.

Burts et al., Brush-first and click: efficient synthesis of nanoparticles that degrade and release doxorubicin in response to light. Photochem Photobiol. Mar.-Apr. 2014;90(2):380-5. doi: 10.1111/php.12182. Epub Nov. 25, 2013.

Burts et al., Brush-first synthesis of core-photodegradable miktoarm star polymers via ROMP: towards photoresponsive self-assemblies. Macromol Rapid Commun. Jan. 2014;35(2):168-173. doi: 10.1002/marc.201300618. Epub Nov. 22, 2013.

Burts et al., Using EPR to Compare PEG-branch-nitroxide "Bivalent-Brush Polymers" and Traditional PEG Bottle-Brush Polymers: Branching Makes a Difference. Macromolecules, Oct. 2012;45(20):8310-8318.

Cabral et al., Accumulation of sub-100 nm polymeric micelles in poorly permeable tumours depends on size. Nat Nanotechnol. Oct. 23, 2011;6(12):815-23. doi: 10.1038/nnano.2011.166.

Caiolfa et al., Polymer-bound camptothecin: initial biodistribution and antitumour activity studies. J Control Release. Mar. 1, 2000;65(1-2):105-19.

Calvez et al., One step synthesis of MOF-polymer composites. RSC Adv., 2016;6:17314-7.

Campos-Fernández et al., A One-Pot, High-Yield Synthesis of a Paramagnetic Nickel Square from Divergent Precursors by Anion Template Assembly. Angewandte Chemie International Edition. Dec. 3, 1999;38(23):3477-3479.

Campos-Fernández et al., Fine-tuning the ring-size of metallacyclophanes: a rational approach to molecular pentagons. J Am Chem Soc. Jan. 31, 2001;123(4):773-4.

Caravan et al., Gadolinium(III) Chelates as MRI Contrast Agents: Structure, Dynamics, and Applications. Chem Rev. Sep. 8, 1999;99(9):2293-352.

Castilla et al., Stereochemistry in subcomponent self-assembly. Acc Chem Res. Jul. 15, 2014;47(7):2063-73. doi: 10.1021/ar5000924. Epub May 2, 2014.

Chakrabarty et al., Supramolecular coordination: self-assembly of finite two- and three-dimensional ensembles. Chem Rev. Nov. 9, 2011;111(11):6810-918. doi: 10.1021/cr200077m. Epub Aug. 24, 2011.

Chambron et al., Topologically complex molecules obtained by transition metal templation: it is the presentation that determines the synthesis strategy. New Journal of Chemistry. 2013;37(1):49-57.

Chand et al., Self-assembly of a novel macrotricyclic Pd(II) metallocage encapsulating a nitrate ion. Chem Commun (Camb). Sep. 7, 2001;(17):1652-3.

Chang et al., Dose-dense chemotherapy improves mechanisms of antitumor immune response. Cancer Res. Jan. 1, 2013;73(1):119-27. doi: 10.1158/0008-5472.CAN-12-2225. Epub Oct. 29, 2012.

Chen et al., Polymeric phosphorylcholine-camptothecin conjugates prepared by controlled free radical polymerization and click chemistry. Bioconjug Chem. Dec. 2009;20(12):2331-41. doi: 10.1021/bc900339x.

Chen et al., Synthesis of superporous hydrogels: hydrogels with fast swelling and superabsorbent properties. J Biomed Mater Res. Jan. 1999;44(1):53-62.

Cheon et al., Synergistically integrated nanoparticles as multimodal probes for nanobiotechnology.Acc Chem Res. Dec. 2008;41(12):1630-40. doi: 10.1021/ar800045c.

Chifotides et al., Anion-π interactions in supramolecular architectures. Acc Chem Res. Apr. 16, 2013;46(4):894-906. doi: 10.1021/ar300251k. Epub Mar. 11, 2013.

Choi et al., Self-confirming "AND" logic nanoparticles for fault-free MRI. J Am Chem Soc. Aug. 18, 2010;132(32):11015-7. doi: 10.1021/ja104503g.

Chou et al., In vitro and in vivo studies of FePt nanoparticles for dual modal CT/MRI molecular imaging. J Am Chem Soc. Sep. 29, 2010;132(38):13270-8. doi: 10.1021/ja1035013.

Clever et al., Inclusion of anionic guests inside a molecular cage with palladium(II) centers as electrostatic anchors. Angew Chem Int Ed Engl. 2009;48(38):7010-2. doi: 10.1002/anie.200902717.

Cok et al., Synthesis of Model Network Hydrogels via Tetrazine-Olefin Inverse Electron Demand Diels-Alder Cycloaddition. Macromolecular Symposia. Jul. 2013;329(1):108-112.

Conrad et al., Tunable, temperature-responsive polynorbornenes with side chains based on an elastin peptide sequence. Angew Chem Int Ed Engl. 2009;48(44):8328-30. doi: 10.1002/anie.200903888.

Cook et al., Biomedical and biochemical applications of self-assembled metallacycles and metallacages. Acc Chem Res. Nov. 19, 2013;46(11):2464-74. doi: 10.1021/ar400010v. Epub Jun. 20, 2013.

Cook et al., Metal-organic frameworks and self-assembled supramolecular coordination complexes: comparing and contrasting the design, synthesis, and functionality of metal-organic materials. Chem Rev. Jan. 9, 2013;113(1):734-77. doi: 10.1021/cr3002824. Epub Nov. 2, 2012.

Cook et al., Recent Developments in the Preparation and Chemistry of Metallacycles and Metallacages via Coordination. Chem Rev. Aug. 12, 2015;115(15):7001-45. doi: 10.1021/cr5005666. Epub Mar. 27, 2015.

(56) References Cited

OTHER PUBLICATIONS

Cordier et al., Self-healing and thermoreversible rubber from supramolecular assembly. Nature. Feb. 21, 2008;451(7181):977-80. doi: 10.1038/nature06669.

Dag et al., Three-arm star ring opening metathesis polymers via alkyne-azide click reaction. J. Polym. Sci. A Polym. Chem., 47: 2344-2351. doi:10.1002/pola.23324.

Davies et al., Environmentally responsive MRI contrast agents. Chem Commun (Camb). Oct. 28, 2013;49(84):9704-21. doi: 10.1039/c3cc44268c.

Davis et al., A novel nitroxide is an effective brain redox imaging contrast agent and in vivo radioprotector. Free Radic Biol Med. Aug. 1, 2011;51(3):780-90. doi: 10.1016/j.freeradbiomed.2011.05.019. Epub May 25, 2011.

Davis et al., Nanoparticle therapeutics: an emerging treatment modality for cancer. Nat Rev Drug Discov. Sep. 2008;7(9):771-82. doi: 10.1038/nrd2614.

De La Cruz et al., Theory of microphase separation in graft and star copolymers. Macromolecules, 1986;19(10):2501-8. DOI: 10.1021/ma00164a008.

Desmarets et al., Design, Self-Assembly, and Molecular Structures of 3D Copper(II) Capsules Templated by BF4—Guest Anions. European Journal of Inorganic Chemistry. Oct. 2009;(29-30):4396-4400. doi: 10.1002/ejic.200900606.

Detape et al., Advanced multimodal nanoparticles delay tumor progression with clinical radiation therapy. J Control Release. Sep. 28, 2016;238:103-113. doi: 10.1016/j.jconrel.2016.07.021. Epub Jul. 14, 2016.

Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.

Dhar et al., Targeted delivery of a cisplatin prodrug for safer and more effective prostate cancer therapy in vivo. Proc Natl Acad Sci U S A. Feb. 1, 2011;108(5):1850-5. doi: 10.1073/pnas.1011379108. Epub Jan. 13, 2011.

Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.

Doane et al., The unique role of nanoparticles in nanomedicine: imaging, drug delivery and therapy. Chem Soc Rev. Apr. 7, 2012;41(7):2885-911. doi: 10.1039/c2cs15260f. Epub Jan. 27, 2012.

Duncan, The dawning era of polymer therapeutics. Nat Rev Drug Discov. May 2003;2(5):347-60.

Durr et al., Mild and Efficient Modular Synthesis of Poly(acrylonitrile-co-butadiene) Block and Miktoarm Star Copolymer Architectures. Macromolecules, 2013;46(1):49-62. DOI: 10.1021/ma302017c.

Elliott et al., Metabolism of brain tissue slices and suspensions from various mammals. J Neurophysiol. Nov. 1948;11(6):473-84.

Eryazici et al., Square-planar Pd(II), Pt(II), and Au(III) terpyridine complexes: their syntheses, physical properties, supramolecular constructs, and biomedical activities. Chem Rev. Jun. 2008;108(6):1834-95. doi: 10.1021/cr0781059.

Eryazici et al., Two Large-Pore Metal-Organic Frameworks Derived from a Single Polytopic Strut. Crystal Growth & Design. Mar. 7, 2012;12(3):1075-1080.

Feng et al., A metabonomic analysis of organ specific response to USPIO administration. Biomaterials. Sep. 2011;32(27):6558-69. doi: 10.1016/j.biomaterials.2011.05.035.

Ferrauto et al., Frequency-encoded MRI-CEST agents based on paramagnetic liposomes/RBC aggregates. Nano Lett. Dec. 10, 2014;14(12):6857-62. doi: 10.1021/nl5026612. Epub Nov. 10, 2014.

Ferrauto et al., Lanthanide-loaded erythrocytes as highly sensitive chemical exchange saturation transfer MRI contrast agents. J Am Chem Soc. Jan. 15, 2014;136(2):638-41. doi: 10.1021/ja411793u. Epub Dec. 30, 2013.

Forgan et al., Chemical topology: complex molecular knots, links, and entanglements. Chem Rev. Sep. 14, 2011;111(9):5434-64. doi: 10.1021/cr200034u. Epub Jun. 21, 2011.

Foster et al., Differentially Addressable Cavities within Metal-Organic Cage-Cross-Linked Polymeric Hydrogels. J Am Chem Soc. Aug. 5, 2015;137(30):9722-9. doi: 10.1021/jacs.5b05507. Epub Jul. 23, 2015.

Fox et al., Soluble polymer carriers for the treatment of cancer: the importance of molecular architecture. Acc Chem Res. Aug. 18, 2009;42(8):1141-51. doi: 10.1021/ar900035f.

Fujita et al., Coordination assemblies from a Pd(II)-cornered square complex. Acc Chem Res. Apr. 2005;38(4):371-80.

Fujita et al., Metal-directed self-assembly of two- and three-dimensional synthetic receptors. Chem. Soc. Rev., 1998;27:417-25. doi: 10.1039/A827417Z.

Fujita et al., Self-Assembly of M30L60 Icosidodecahedron. Chem 2016;1:91.

Fujita et al., Self-assembly of ten molecules into nanometre-sized organic host frameworks. Nature Nov. 1995;378:469-71. doi:10.1038/378469a0.

Fullenkamp et al., Mussel-Inspired Histidine-Based Transient Network Metal Coordination Hydrogels. Macromolecules. Jan. 18, 2013;46(3):1167-1174.

Furukawa et al., Structuring of metal-organic frameworks at the mesoscopic/macroscopic scale. Chem Soc Rev. Aug. 21, 2014;43(16):5700-34. doi: 10.1039/c4cs00106k.

Furukawa et al., The chemistry and applications of metal-organic frameworks. Science. Aug. 30, 2013;341:1230444. doi: 10.1126/science.1230444.

Gadzikwa et al., Covalent surface modification of a metal-organic framework: selective surface engineering via Cu(I)-catalyzed Huisgen cycloaddition. Chem Commun (Camb). Nov. 21, 2008;(43):5493-5. doi: 10.1039/b805101a. Epub Oct. 8, 2008.

Gamage et al., MOF-5-Polystyrene: Direct Production from Monomer, Improved Hydrolytic Stability, and Unique Guest Adsorption. Angew Chem Int Ed Engl. Sep. 19, 2016;55(39):12099-103. doi: 10.1002/anie.201606926. Epub Aug. 24, 2016.

Gao et al., Development of star polymers as unimolecular containers for nanomaterials. Macromol Rapid Commun. May 14, 2012;33(9):722-34. doi: 10.1002/marc.201200005. Epub Mar. 14, 2012.

Gao et al., Modular Approaches to Star and Miktoarm Star Polymers by ATRP of Cross-Linkers. Macromol. Symp., 291-292: 12-16. doi:10.1002/masy.201050502.

Gao et al., Synthesis of Acid-Labile PEG and PEG-Doxorubicin-Conjugate Nanoparticles via Brush-First ROMP. ACS Macro Lett. Sep. 16, 2014;3(9):854-857. Epub Aug. 13, 2014.

Gao et al., Synthesis of functional polymers with controlled architecture by CRP of monomers in the presence of cross-linkers: From stars to gels. Progress in Polymer Science Apr. 2009;34(4):317-350.

Gao et al., Synthesis of Star Polymers by a New "Core-First" Method: Sequential Polymerization of Cross-Linker and Monomer. Macromolecules, 2008;41(4):1118-1125.

Ge et al., A Pyrene-functionalized Polynorbornene for Ratiometric Fluorescence Sensing of Pyrophosphate. Chem. Asian J. 2016;11:687.

Gilgorich et al., Palladium-catalyzed reductive coupling of styrenes and organostannanes under aerobic conditions. J Am Chem Soc. Nov. 21, 2007;129(46):14193-5. Epub Oct. 27, 2007.

Glunde et al., Magnetic resonance spectroscopy in metabolic and molecular imaging and diagnosis of cancer. Chem Rev. May 12, 2010;110(5):3043-59. doi: 10.1021/cr9004007.

Goh et al., Highly efficient synthesis of low polydispersity core cross-linked star polymers by Ru-catalyzed living radical polymerization. Macromol Rapid Commun. Mar. 2, 2011;32(5):456-61. doi: 10.1002/marc.201000641. Epub Jan. 7, 2011.

Goto et al., "Clickable" metal-organic framework. J Am Chem Soc. Nov. 5, 2008;130(44):14354-5. doi: 10.1021/ja7114053. Epub Oct. 8, 2008.

Greenwald et al., Effective drug delivery by PEGylated drug conjugates. Adv Drug Deliv Rev. Feb. 10, 2003;55(2):217-50.

Grumbley et al., Photoresponsive Polymers Containing Nitrobenzyl Esters via Ring-Opening Metathesis Polymerization. Macromolecules. 2011;44(20):7956-61.

Hackelbusch et al., Chain Dynamics in Supramolecular Polymer Networks. Macromolecules. 2013;46(15):6273-6286.

(56) References Cited

OTHER PUBLICATIONS

Hackelbusch et al., Multiresponsive Polymer Hydrogels by Orthogonal Supramolecular Chain Cross-Linking. Macromolecules. 2014;47(12):4028-4036.

Haddleton et al., Well-defined oligosaccharide-terminated polymers from living radical polymerization. Biomacromolecules. 2000 Summer;1(2):152-6.

Hafkamp et al., Organogel formation and molecular imprinting by functionalized gluconamides and their metal complexes. Chemical Communications. 1997;6:545-546. doi: 10.1039/A608266A.

Hall et al., Platinum(IV) antitumour compounds: their bioinorganic chemistry. Coord Chem Rev. 2002;232:49-67.

Hall et al., The cellular distribution and oxidation state of platinum(II) and platinum(IV) antitumour complexes in cancer cells. J Biol Inorg Chem. Sep. 2003;8(7):726-32. Epub Jul. 12, 2003.

Han et al., Recent Development of Peptide Coupling Reagents in Organic Synthesis. Tetrahedron, 2004;60:2447-2467.

Hansell et al., Additive-free clicking for polymer functionalization and coupling by tetrazine-norbornene chemistry. J Am Chem Soc. Sep. 7, 2011;133(35):13828-31. doi: 10.1021/ja203957h. Epub Aug. 11, 2011.

Hao et al., Dendrimers as scaffolds for multifunctional reversible addition-fragmentation chain transfer agents: Syntheses and polymerization. J. Polym. Sci. A Polym. Chem., 2004;42:5877-5890. doi:10.1002/pola.20434.

Hardy et al., Generation of metallosupramolecular polymer gels from multiply functionalized grid-type complexes. New J. Chem., 2012;36:668-73.

Harrington et al., Holdfast heroics: comparing the molecular and mechanical properties of Mytilus californianus byssal threads. J Exp Biol. Dec. 2007;210(Pt 24):4307-18.

Harrington et al., Iron-clad fibers: a metal-based biological strategy for hard flexible coatings. Science. Apr. 9, 2010;328(5975):216-20. doi: 10.1126/science.1181044. Epub Mar. 4, 2010.

Harris et al., Giant hollow M(n)L(2n) spherical complexes: structure, functionalisation and applications. Chem Commun (Camb). Aug. 4, 2013;49(60):6703-12. doi: 10.1039/c3cc43191f.

Harrison et al., A multimeric MR-optical contrast agent for multimodal imaging. Chem Commun (Camb). Oct. 9, 2014;50(78):11469-71. doi: 10.1039/c4cc05651e.

Harrison et al., Multimeric Near IR-MR Contrast Agent for Multimodal In Vivo Imaging. J Am Chem Soc. Jul. 22, 2015;137(28):9108-16. doi: 10.1021/jacs.5b04509. Epub Jul. 14, 2015.

Harvey et al., Lanthanide Complexes as Paramagnetic Probes for 19F Magnetic Resonance. Eur. J. Inorg. Chem., 2012: 2015-2022. doi:10.1002/ejic.201100894.

Hatje et al., Increases in Anthropogenic Gadolinium Anomalies and Rare Earth Element Concentrations in San Francisco Bay over a 20 Year Record. Environ Sci Technol. Apr. 19, 2016;50(8):4159-68. doi: 10.1021/acs.est.5b04322. Epub Jan. 25, 2016.

Hedrick et al., Dendrimer-like Star Block and Amphiphilic Copolymers by Combination of Ring Opening and Atom Transfer Radical Polymerization. Macromolecules, 1998;31(25):8691-8705. DOI: 10.1021/ma980932b.

Hein et al., Copper-catalyzed azide-alkyne cycloaddition (CuAAC) and beyond: new reactivity of copper(I) acetylides. Chem Soc Rev. Apr. 2010;39(4):1302-15. doi: 10.1039/b904091a. Epub Mar. 4, 2010.

Helms et al., One-Pot Reaction Cascades Using Star Polymers with Core-Confined Catalysts. Angewandte Chemie, 2005;44:6384-6387. doi:10.1002/ange.200502095.

Hirakawa et al., Removal of Perchlorate Anion from an Aqueous Solution by Encapsulation in an Anion-templated Self-assembled Molecular Capsule. Chemistry Letters. 2009;38(3):290-291.

Holbrook et al., Gd(III)-Dithiolane Gold Nanoparticles for T1-Weighted Magnetic Resonance Imaging of the Pancreas. Nano Lett. May 11, 2016;16(5):3202-9. doi: 10.1021/acs.nanolett.6b00599. Epub Apr. 20, 2016.

Holliday et al., Strategies for the Construction of Supramolecular Compounds through Coordination Chemistry. Angew Chem Int Ed Engl. Jun. 1, 2001;40(11):2022-2043.

Holten-Andersen et al., Metal-coordination: using one of nature's tricks to control soft material mechanics. J. Mater. Chem. B. 2014;2:2467-2472.

Holten-Andersen et al., pH-induced metal-ligand cross-links inspired by mussel yield self-healing polymer networks with near-covalent elastic moduli. PNAS. Feb. 15, 2011;108:2651-2655.

Hosono et al., Metal-Organic Polyhedral Core as a Versatile Scaffold for Divergent and Convergent Star Polymer Synthesis. J Am Chem Soc. May 25, 2016;138(20):6525-31. doi: 10.1021/jacs.6b01758. Epub May 11, 2016.

Hu et al., Nanoparticle-based combination therapy toward overcoming drug resistance in cancer. Biochem Pharmacol. Apr. 15, 2012;83(8):1104-11. doi: 10.1016/j.bcp.2012.01.008. Epub Jan. 18, 2012.

Huang et al., Polymer-Stabilized Perfluorobutane Nanodroplets for Ultrasound Imaging Agents. J Am Chem Soc. Jan. 11, 2017;139(1):15-18. doi: 10.1021/jacs.6b08800. Epub Dec. 29, 2016.

Huinink et al., Topotecan versus paclitaxel for the treatment of recurrent epithelial ovarian cancer. J Clin Oncol. Jun. 1997;15(6):2183-93.

Huynh, Novel Polymeric Micelles via RAFT Polymerization for Platinum Drug Delivery. Doctoral Thesis. The University of New South Wales. 2012:i, 57-58.

Hyodo et al., Assessment of tissue redox status using metabolic responsive contrast agents and magnetic resonance imaging. J Pharm Pharmacol. Aug. 2008;60(8):1049-60. doi: 10.1211/jpp.60.8.0011.

Hyodo et al., Brain redox imaging using blood-brain barrier-permeable nitroxide MRI contrast agent. J Cereb Blood Flow Metab. Jun. 2008;28(6):1165-74. doi: 10.1038/jcbfm.2008.5. Epub Feb. 13, 2008.

Hyodo et al., Probing the intracellular redox status of tumors with magnetic resonance imaging and redox-sensitive contrast agents. Cancer Res. Oct. 15, 2006;66(20):9921-8.

Iha et al., Applications of Orthogonal "Click" Chemistries in the Synthesis of Functional Soft Materials. Chem. Rev., 2009;109(11):5620-5686. DOI: 10.1021/cr900138t.

Inglis et al., Well-defined star shaped polymer-fullerene hybrids via click chemistry. Soft Matter, 2010;6:82-84. DOI: 10.1039/B920806M.

Jackson et al., pH triggered self-assembly of core cross-linked star polymers possessing thermoresponsive cores. Chem. Commun., 2011;47:6807-6809. DOI: 10.1039/C1CC11785H.

Jamieson et al., Structure, Recognition, and Processing of Cisplatin-DNA Adducts. Chem Rev. Sep. 8, 1999;99(9):2467-98.

Jansze et al., Ligand Aspect Ratio as a Decisive Factor for the Self-Assembly of Coordination Cages. J Am Chem Soc. Feb. 17, 2016;138(6):2046-54. doi: 10.1021/jacs.5b13190. Epub Feb. 8, 2016.

Jesberger et al., Hyperbranched polymers as scaffolds for multifunctional reversible addition-fragmentation chain-transfer agents: A route to polystyrene-core-polyesters and polystyrene-block-poly(butyl acrylate)-core-polyesters. J. Polym. Sci. A Polym. Chem., 2003;41:3847-3861. doi:10.1002/pola.10976.

Jiang et al., Iterative Exponential Growth Synthesis and Assembly of Uniform Diblock Copolymers. J Am Chem Soc. Aug. 3, 2016;138(30):9369-72. doi: 10.1021/jacs.6b04964. Epub Jul. 20, 2016.

Jiang et al., Thiophene-coated functionalized M12L24 spheres: synthesis, characterization, and electrochemical properties. Chem Asian J. Oct. 2012;7(10):2230-4. doi: 10.1002/asia.201200413. Epub Jul. 9, 2012.

Johnson et al., Construction of Linear Polymers, Dendrimers, Networks, and Other Polymeric Architectures by Copper-Catalyzed Azide-Alkyne Cycloaddition "Click" Chemistry. Macromol Rapid Commun Jul. 2008;29(12-13):1052-72.

Johnson et al., Core-clickable PEG-branch-azide bivalent-bottle-brush polymers by ROMP: grafting-through and clicking-to. J Am Chem Soc. Jan. 26, 2011;133(3):559-66. doi: 10.1021/ja108441d. Epub Dec. 13, 2010.

(56) References Cited

OTHER PUBLICATIONS

Johnson et al., Drug-loaded, bivalent-bottle-brush polymers by graft-through ROMP. Macromolecules. Dec. 28, 2010;43(24):10326-10335.

Johnson et al., Efficient Synthesis of Doxorubicin Releasing Brush Polymers by Graft-Through Romp. Polymer Preprints. 2010;51(2):96-97.

Johnson et al., Synthesis of degradable model networks via ATRP and click chemistry. J Am Chem Soc. May 24, 2006;128(20):6564-5.

Jokerst et al., Molecular imaging with theranostic nanoparticles. Acc Chem Res. Oct. 18, 2011;44(10):1050-60. doi: 10.1021/ar200106e. Epub Sep. 15, 2011.

Jokerst et al., Nanoparticle PEGylation for imaging and therapy. Nanomedicine (Lond). Jun. 2011;6(4):715-28. doi: 10.2217/nnm.11.19.

Joralemon et al., PEGylated polymers for medicine: from conjugation to self-assembled systems. Chem Commun (Camb). Mar. 7, 2010;46(9):1377-93. doi: 10.1039/b920570p. Epub Jan. 28, 2010.

Kalyani et al., Oxidatively intercepting Heck intermediates: Pd-catalyzed 1,2- and 1,1-arylhalogenation of alkenes. J Am Chem Soc. Feb. 20, 2008;130(7):2150-1. doi: 10.1021/ja0782798. Epub Jan. 30, 2008.

Kawamoto et al., Dual Role for 1,2,4,5-Tetrazines in Polymer Networks: Combining Diels—Alder Reactions and Metal Coordination to Generate Functional Supramolecular Gels. ACS Macro Letters 2015;4(4):458-61. doi: 10.1021/acsmacrolett.5b00221.

Kawamoto et al., Graft-through Synthesis and Assembly of Janus Bottlebrush Polymers from A-Branch-B Diblock Macromonomers. J Am Chem Soc. Sep. 14, 2016;138(36):11501-4. doi: 10.1021/jacs.6b07670. Epub Sep. 1, 2016.

Kean et al., Increasing the maximum achievable strain of a covalent polymer gel through the addition of mechanically invisible cross-links. Adv Mater. Sep. 10, 2014;26(34):6013-8. doi: 10.1002/adma.201401570. Epub Jul. 17, 2014.

Keana et al., Nitroxides as potential contrast enhancing agents for MRI application: influence of structure on the rate of reduction by rat hepatocytes, whole liver homogenate, subcellular fractions, and ascorbate. Magn Reson Med. Dec. 1987;5(6):525-36.

Khanna et al., Designing Miktoarm Polymers Using a Combination of "Click" Reactions in Sequence with Ring-Opening Polymerization. Macromolecules, 2010;43(13):5688-5698. DOI: 10.1021/ma100845a.

Kikuchi et al., Stepwise DNA condensation by a histone-mimic peptide-coated M12L24 spherical complex. Chem. Sci., 2014;5:3257-60.

Kim et al., Anion-directed self-assembly of coordination polymer into tunable secondary structure. J Am Chem Soc. Jun. 9, 2004;126(22):7009-14.

Kim et al., Supporting Information Experimental Section. J Am Chem Soc. Jun. 9, 2004;126(22):7009-14. Available at: http://pubs.acs.org/doi/suppl/10.1021/ja049799v/suppl_file/ja049799vsi20040219_113203.pdf Retrieved Apr. 24, 2015.

Kirchhoff et al., Boronic acids: new coupling partners in room-temperature Suzuki reactions of alkyl bromides. Crystallographic characterization of an oxidative-addition adduct generated under remarkably mild conditions. J Am Chem Soc. Nov. 20, 2002;124(46):13662-3.

Kishi et al., An M2L4 molecular capsule with an anthracene shell: encapsulation of large guests up to 1 nm. J Am Chem Soc. Aug. 3, 2011;133(30):11438-41. doi: 10.1021/ja2037029. Epub Jul. 8, 2011.

Kokuryo et al., SPIO-PICsome: development of a highly sensitive and stealth-capable MRI nano-agent for tumor detection using SPIO-loaded unilamellar polyion complex vesicles (PICsomes). J Control Release. Aug. 10, 2013;169(3):220-7. doi: 10.1016/j.jconrel.2013.03.016. Epub Mar. 29, 2013.

Kolishetti et al., Engineering of self-assembled nanoparticle platform for precisely controlled combination drug therapy. Proc Natl Acad Sci U S A. Oct. 19, 2010;107(42):17939-44. doi: 10.1073/pnas.1011368107. Epub Oct. 4, 2010.

Kreutzer et al., Water-Soluble, Unimolecular Containers Based on Amphiphilic Multiarm Star Block Copolymers. Macromolecules, 2006;39(13):4507-4516. DOI: 10.1021/ma060548b.

Kuppler et al., Potential applications of metal-organic frameworks. Coord. Chem. Rev. 2009;253:3042-66.

Kwon et al., Block copolymer micelles as long-circulating drug vehicles. Adv Drug Delivery Rev. 1995;16:295-309.

Lammers et al., Simultaneous delivery of doxorubicin and gemcitabine to tumors in vivo using prototypic polymeric drug carriers. Biomaterials. Jul. 2009;30(20):3466-75. doi: 10.1016/j.biomaterials.2009.02.040. Epub Mar. 21, 2009.

Laurier et al., Iron(III)-based metal-organic frameworks as visible light photocatalysts. J Am Chem Soc. Oct. 2, 2013;135(39):14488-91. doi: 10.1021/ja405086e. Epub Sep. 17, 2013.

Lee et al., Multifunctional nanoparticles for multimodal imaging and theragnosis. Chem Soc Rev. Apr. 7, 2012;41(7):2656-72. doi: 10.1039/c2cs15261d. Epub Dec. 21, 2011.

Lee et al., Mussel-Inspired Adhesives and Coatings. Annu Rev Mater Res. Aug. 1, 2011;41:99-132.

Lee et al., Single-molecule mechanics of mussel adhesion. Proc Natl Acad Sci U S A. Aug. 29, 2006;103(35):12999-3003. Epub Aug. 18, 2006.

Lee et al., Stimuli-responsive molecular brushes. Progress in Polymer Science (Oxford), 35(1-2), 24-44. DOI: 10.1016/j.progpolymsci.2009.11.002.

Leibfarth et al., Scalable synthesis of sequence-defined, unimolecular macromolecules by Flow-IEG. Proc Natl Acad Sci U S A. Aug. 25, 2015;112(34):10617-22. doi: 10.1073/pnas.1508599112. Epub Aug. 12, 2015.

Leininger et al., Self-assembly of discrete cyclic nanostructures mediated by transition metals. Chem Rev. Mar. 8, 2000;100(3):853-908.

Li et al., Polycatechol Nanoparticle MRI Contrast Agents. Small, 2016;12(5):668-677. https://doi.org/10.1002/smll.201502754.

Li et al., A magnetic switch for spin-catalyzed interconversion of nuclear spin isomers. J Am Chem Soc. Mar. 31, 2010;132(12):4042-3. doi: 10.1021/ja910282p.

Li et al., Cross-linked supramolecular polymer gels constructed from discrete multi-pillar[5]arene metallacycles and their multiple stimuli-responsive behavior. J Am Chem Soc. Jun. 18, 2014;136(24):8577-89. doi: 10.1021/ja413047r. Epub Mar. 11, 2014.

Li et al., Design and synthesis of an exceptionally stable and highly porous metal-organic framework. Nature Nov. 1999;402:276-79. doi:10.1038/46248.

Li et al., Distance-Dependent Paramagnet-Enhanced Nuclear Spin Relaxation of H2@C60 Derivatives Covalently Linked to a Nitroxide Radical. J. Phys. Chem. Lett., 2010;1(14):2135-2138. DOI: 10.1021/jz100645w.

Li et al., Highly fluorescent M2L4 molecular capsules with anthracene shells. Chem Commun (Camb). Aug. 14, 2011;47(30):8605-7. doi: 10.1039/c1cc12946e. Epub Jun. 28, 2011.

Li et al., Isostructural M2L4 molecular capsules with anthracene shells: synthesis, crystal structures, and fluorescent properties. Chemistry. Jul. 2, 2012;18(27):8358-65. doi: 10.1002/chem.201200155. Epub May 25, 2012.

Li et al., Metallo/clusto hybridized supramolecular polymers. Soft Matter. Dec. 7, 2014;10(45):9038-53. doi: 10.1039/c4sm01684j.

Li et al., Pinpointing the extent of electronic delocalization in the Re(I)-to-tetrazine charge-separated excited state using time-resolved infrared spectroscopy. J Am Chem Soc. Aug. 26, 2009;131(33):11656-7. doi: 10.1021/ja903901n.

Li et al., Star Polymers via Cross-Linking Amphiphilic Macroinitiators by AGET ATRP in Aqueous Media. J. Am. Chem. Soc., 2009;131(30):10378-10379. DOI: 10.1021/ja904204g.

Li et al., Surface Properties of Bottlebrush Polymer Thin Films. Macromolecules. 2012;45(17):7118-7127.

Liang et al., The copper(I)-catalyzed alkyne-azide cycloaddition (CuAAC) "click" reaction and its applications. An overview. Coordination Chemistry Reviews Dec. 2011;255(23-24):2933-2945.

Liao et al., A convergent synthetic platform for single-nanoparticle combination cancer therapy: ratiometric loading and controlled

(56) References Cited

OTHER PUBLICATIONS release of cisplatin, doxorubicin, and camptothecin. J Am Chem Soc. Apr. 23, 2014;136(16):5896-9. doi: 10.1021/ja502011g. Epub Apr. 11, 2014.

Liao et al., A palladium-catalyzed three-component cross-coupling of conjugated dienes or terminal alkenes with vinyl triflates and boronic acids. J Am Chem Soc. Apr. 20, 2011;133(15):5784-7. doi: 10.1021/ja201358b. Epub Mar. 30, 2011.

Liao et al., Palladium-catalyzed hydroarylation of 1,3-dienes with boronic esters via reductive formation of pi-allyl palladium intermediates under oxidative conditions. J Am Chem Soc. Aug. 4, 2010;132(30):10209-11. doi: 10.1021/ja105010t.

Liao et al., Two-component control of guest binding in a self-assembled cage molecule. Chem Commun (Camb). Jul. 21, 2010;46(27):4932-4. doi: 10.1039/c0cc00234h. Epub Jun. 2010.

Lim et al., Multiplexed imaging of therapeutic cells with multispectrally encoded magnetofluorescent nanocomposite emulsions. J Am Chem Soc. Dec. 2, 2009;131(47):17145-54. doi: 10.1021/ja904472z.

Liu et al., "Brush-first" method for the parallel synthesis of photocleavable, nitroxide-labeled poly(ethylene glycol) star polymers. J Am Chem Soc. Oct. 3, 2012;134(39):16337-44. doi: 10.1021/ja3067176. Epub Sep. 24, 2012.

Liu et al., Aqueous Dispersion Polymerization of 2-Methoxyethyl Acrylate for the Synthesis of Biocompatible Nanoparticles Using a Hydrophilic RAFT Polymer and a Redox Initiator. Macromolecules, 2011;44(13):5237-5245. DOI: 10.1021/ma200984h.

Liu et al., Assembly of trigonal and tetragonal prismatic cages from octahedral metal ions and a flexible molecular clip. Inorg Chem. Jul. 23, 2007;46(15):5814-6. Epub Jan. 26, 2007.

Liu et al., Composites of metal-organic frameworks and carbon-based materials: preparations, functionalities and applications. J. Mater. Chem. A, 2016;4:3584-616.

Liu et al., Discrete M2L2 metallacycle and M2L4 cage frameworks and anion competitive reactions of Cu2L4 type receptor. Inorganic Chemistry Communications. Jun. 2009;12(6):457-460.

Liu et al., Nuts and bolts of chemical exchange saturation transfer MRI. NMR Biomed. Jul. 2013;26(7):810-28. doi: 10.1002/nbm.2899. Epub Jan. 10, 2013.

Liu et al., Particles without a Box: Brush-first Synthesis of Photodegradable PEG Star Polymers under Ambient Conditions. J Vis Exp. 2013;80:e50874, doi:10.3791/50874.

Liu et al., Synthesis of functional core, star polymers via RAFT polymerization for drug delivery applications. Macromol Rapid Commun. May 14, 2012;33(9):760-6. doi: 10.1002/marc.201200029. Epub Apr. 12, 2012.

Lock et al., One-Component Supramolecular Filament Hydrogels as Theranostic Label-Free Magnetic Resonance Imaging Agents. ACS Nano. Jan. 24, 2017;11(1):797-805.

Love et al., A practical and highly active ruthenium-based catalyst that effects the cross metathesis of acrylonitrile. Angew Chem Int Ed Engl. Nov. 4, 2002;41(21):4035-7.

Loveless et al., Chemoresponsive viscosity switching of a metallo-supramolecular polymer network near the percolation threshold. J. Mater Chem. 2007;17:56-61.

Loveless et al., Rational Control of Viscoelestic Properties in Multicomponent Associative Polymer Networks. Macromolecules. 2005;38(24):10171-10177.

Lutz et al., From precision polymers to complex materials and systems. Nat Rev Mat, 2016;1:1. doi:10.1038/natrevmats.2016.24.

Lynd et al., Influence of Polydispersity on the Self-Assembly of Diblock Copolymers. Macromolecules, 2005;38(21):8803-10.

Ma et al., Nanoparticles for combination drug therapy. ACS Nano. Nov. 26, 2013;7(11):9518-25. doi: 10.1021/nn405674m.

Mackay et al., Self-assembling chimeric polypeptide-doxorubicin conjugate nanoparticles that abolish tumours after a single injection. Nat Mater. Dec. 2009;8(12):993-9. doi: 10.1038/nmat2569. Epub Nov. 8, 2009.

Macrenaris et al., Cell-Permeable Esterase-Activated Ca(II)-Sensitive MRI Contrast Agent. Bioconjug Chem. Feb. 17, 2016;27(2):465-73. doi: 10.1021/acs.bioconjchem.5b00561. Epub Jan. 6, 2016.

Maeda et al., Polymeric drugs for efficient tumor-targeted drug delivery based on EPR-effect. Eur J Pharm Biopharm. Mar. 2009;71(3):409-19. doi: 10.1016/j.ejpb.2008.11.010. Epub Dec. 3, 2008.

Mai et al., Self-assembly of block copolymers. Chem Soc Rev. Sep. 21, 2012;41(18):5969-85. doi: 10.1039/c2cs35115c. Epub Jul. 9, 2012.

Mastarone et al., A modular system for the synthesis of multiplexed magnetic resonance probes. J Am Chem Soc. Apr. 13, 2011;133(14):5329-37. doi: 10.1021/ja1099616. Epub Mar. 17, 2011.

Matson et al., Synthesis of fluorine-18 functionalized nanoparticles for use as in vivo molecular imaging agents. J Am Chem Soc. May 28, 2008;130(21):6731-3. doi: 10.1021/ja802010d. Epub May 2, 2008.

Matsumoto et al., High-resolution mapping of tumor redox status by magnetic resonance imaging using nitroxides as redox-sensitive contrast agents. Clin Cancer Res. Apr. 15, 2006;12(8):2455-62.

Matsumura et al., A new concept for macromolecular therapeutics in cancer chemotherapy: mechanism of tumoritropic accumulation of proteins and the antitumor agent smancs. Cancer Res. Dec. 1986;46(12 Pt 1):6387-92.

Matyjaszewski et al., Nanostructured functional materials prepared by atom transfer radical polymerization. Nat Chem. Jul. 2009;1(4):276-88. doi: 10.1038/nchem.257. Epub Jun. 22, 2009.

McCammant et al., Palladium-catalyzed 1,4-difunctionalization of butadiene to form skipped polyenes. J Am Chem Soc. Mar. 20, 2013;135(11):4167-70. doi: 10.1021/ja3110544. Epub Mar. 12, 2013.

McConnell et al., Stimuli-Responsive Metal-Ligand Assemblies. Chem Rev. Aug. 12, 2015;115(15):7729-93. doi: 10.1021/cr500632f. Epub Apr. 16, 2015.

McDonald et al., Polymer@MOF@MOF: "grafting from" atom transfer radical polymerization for the synthesis of hybrid porous solids. Chem. Commun. 2015;51:11994-6.

McKenzie et al., Highly Efficient and Versatile Formation of Biocompatible Star Polymers in Pure Water and Their Stimuli-Responsive Self-Assembly. Macromolecules, 2014;47(22):7869-7877. DOI: 10.1021/ma502008j.

McKenzie et al., Visible Light Mediated Controlled Radical Polymerization in the Absence of Exogenous Radical Sources or Catalysts. Macromolecules, 2015;48(12):3864-3872. DOI: 10.1021/acs.macromol.5b00965.

Medarova et al., In vivo imaging of siRNA delivery and silencing in tumors. Nat Med. Mar. 2007;13(3):372-7. Epub Feb. 25, 2007.

Mendichovszky et al., Gadolinium and nephrogenic systemic fibrosis: time to tighten practice. Pediatr Radiol. May 2008;38(5):489-96; quiz 602-3. Epub Oct. 18, 2007.

Meng et al., Controlling the transmission of stereochemical information through space in terphenyl-edged Fe4L6 cages. J Am Chem Soc. Aug. 31, 2011;133(34):13652-60. doi: 10.1021/ja205254s. Epub Aug. 9, 2011.

Menyo et al., Versatile tuning of supramolecular hydrogels through metal complexation of oxidation-resistant catechol-inspired ligands. Soft Matter. 2013;9:10314-10323.

Meyer et al., The dynamic chemistry of molecular borromean rings and Solomon knots. Chemistry. Nov. 8, 2010;16(42):12570-81. doi: 10.1002/chem.201001806.

Mi et al., A pH-activatable nanoparticle with signal-amplification capabilities for non-invasive imaging of tumour malignancy. Nat Nanotechnol. Aug. 2016;11(8):724-30. doi: 10.1038/nnano.2016.72. Epub May 16, 2016.

Mi et al., Hydrothermally synthesized PEGylated calcium phosphate nanoparticles incorporating Gd-DTPA for contrast enhanced MRI diagnosis of solid tumors. Journal of Controlled Release Jan. 2014;174(28):63-71.

(56) References Cited

OTHER PUBLICATIONS

Miyake et al., Precisely tunable photonic crystals from rapidly self-assembling brush block copolymer blends. Angew Chem Int Ed Engl. Nov. 5, 2012;51(45):11246-8. doi: 10.1002/anie.201205743. Epub Sep. 13, 2012.

Moghimi et al., Long-circulating and target-specific nanoparticles: theory to practice. Pharmacol Rev. Jun. 2001;53(2):283-318.

Mukherjee et al., pH-Sensitive Nanoaggregates for Site-Specific Drug-Delivery as Well as Cancer Cell Imaging. ACS Omega, 2016;1(5):755-764. DOI: 10.1021/acsomega.6b00167.

Mukherjee et al., Site-Specific Amphiphilic Magnetic Copolymer Nanoaggregates for Dual Imaging. Macromolecules, 2015;48(19):6791-6800. DOI: 10.1021/acs.macromol.5b01716.

Mukherjee et al., Oximes as reversible links in polymer chemistry: dynamic macromolecular stars. Polym. Chem., 2014;5:6923-6931. DOI: 10.1039/C4PY01282H.

Muthukrishnan et al., Synthesis and Characterization of Glycomethacrylate Hybrid Stars from Silsesquioxane Nanoparticles. Macromolecules, 2005;38(26):10631-10642. DOI: 10.1021/ma051949e.

Na et al., Development of a T1 contrast agent for magnetic resonance imaging using MnO nanoparticles. Angew Chem Int Ed Engl. 2007;46(28):5397-401.

Na et al., Inorganic Nanoparticles for MRI Contrast Agents. Adv. Mater., 21: 2133-2148. doi:10.1002/adma.200802366.

Nair et al., Modulating mechanical properties of self-assembled polymer networks by multifunctional complementary hydrogen bonding. Soft Matter. 2011;7(2):553-559.

Nair et al., Multiresponsive Reversible Polymer Networks Based on Hydrogen Bonding and Metal Coordination. Macromolecules. 2011;44(9):3346-3357.

Nardone et al., Pediatric nephrogenic systemic fibrosis is rarely reported: a RADAR report. Pediatr Radiol. Feb. 2014;44(2):173-80. doi: 10.1007/s00247-013-2795-x. Epub Sep. 21, 2013.

Nese et al., Synthesis, Characterization, and Properties of Starlike Poly(n-butyl acrylate)-b-poly(methyl methacrylate) Block Copolymers. Macromolecules, 2010;43(3):1227-35. DOI: 10.1021/ma902447p.

Nguyen et al., Nitroxide-Based Macromolecular Contrast Agents with Unprecedented Transverse Relaxivity and Stability for Magnetic Resonance Imaging of Tumors. ACS Cent. Sci., 2017;3(7):800-811. DOI: 10.1021/acscentsci.7b00253.

Nicholls et al., DNA-gadolinium-gold nanoparticles for in vivo T1 MR imaging of transplanted human neural stem cells. Biomaterials. Jan. 2016;77:291-306. doi: 10.1016/j.biomaterials.2015.11.021. Epub Nov. 14, 2015.

Nishiyama et al., Novel cisplatin-incorporated polymeric micelles can eradicate solid tumors in mice. Cancer Res. Dec. 15, 2003;63(24):8977-83.

Nitschke et al., Construction, substitution, and sorting of metallo-organic structures via subcomponent self-assembly. Acc Chem Res. Feb. 2007;40(2):103-12.

Nomura et al., Facile Controlled Synthesis of Soluble Star Shape Polymers by Ring-Opening Metathesis Polymerization (ROMP). Macromolecules, 2009;42(4):899-901. DOI: 10.1021/ma8027529.

Nomura et al., Use of Pyridine-Coated Star-Shaped ROMP Polymer As the Supporting Ligand for Ruthenium-Catalyzed Chemoselective Hydrogen Transfer Reduction of Ketones. Organometallics, 2012;31(14):5074-5080. DOI: 10.1021/om300417v.

Ohno et al., Synthesis of well-defined cyclodextrin-core star polymers. J. Polym. Sci. A Polym. Chem., 39: 2206-2214. doi:10.1002/pola.1197.

Olenyuk et al., Self-assembly of nanoscale cuboctahedra by coordination chemistry. Nature. Apr. 29, 1999;398(6730):796-9.

Oliveri et al., Heteroligated supramolecular coordination complexes formed via the halide-induced ligand rearrangement reaction. Acc Chem Res. Dec. 2008;41(12):1618-29. doi: 10.1021/ar800025w.

Pakula et al., Effect of chain topology on the self-organization and the mechanical properties of poly(n-butyl acrylate)-b-polystyrene block copolymers. Polymer, May 26, 2011;52(12):2576-83.

Paletta et al., Synthesis and Reduction Kinetics of Sterically Shielded Pyrrolidine Nitroxides. Org. Lett., 2012;14(20):5322-5325. DOI: 10.1021/ol302506f.

Park et al.,Star Synthesis Using Macroinitiators via Electrochemically Mediated Atom Transfer Radical Polymerization. Macromolecules, 2013;46(15):5856-5860 DOI: 10.1021/ma401308e.

Patel et al., Synthesis and cell adhesive properties of linear and cyclic RGD functionalized polynorbornene thin films. Biomacromolecules. Aug. 13, 2012;13(8):2546-53. doi: 10.1021/bm300795y. Epub Jul. 27, 2012.

Patrick et al., Intracellular pH measurements using perfluorocarbon nanoemulsions. J Am Chem Soc. Dec. 11, 2013;135(49):18445-57. doi: 10.1021/ja407573m. Epub Nov. 22, 2013.

Peer et al., Nanocarriers as an emerging platform for cancer therapy. Nat Nanotechnol. Dec. 2007;2(12):751-60. doi: 10.1038/nnano.2007.387.

Petros et al., Strategies in the design of nanoparticles for therapeutic applications. Nat Rev Drug Discov. Aug. 2010;9(8):615-27. doi: 10.1038/nrd2591. Epub Jul. 9, 2010.

Plummer et al., A Phase I clinical study of cisplatin-incorporated polymeric micelles (NC-6004) in patients with solid tumours. Br J Cancer. Feb. 15, 2011;104(4):593-8. doi: 10.1038/bjc.2011.6. Epub Feb. 1, 2011.

Pluth et al., Proton-mediated chemistry and catalysis in a self-assembled supramolecular host. Acc Chem Res. Oct. 20, 2009;42(10):1650-9. doi: 10.1021/ar900118t.

Pollino et al., Cross-linked and functionalized 'universal polymer backbones' via simple, rapid, and orthogonal multi-site self-assembly. Tetrahedron, 60(34), 7205-7215. DOI: 10.1016/j.tet.2004.05.055.

Qiu et al., Efficient and versatile synthesis of star polymers in water and their use as emulsifiers. Chem. Commun., 2011;47:12685-12687. DOI: 10.1039/C1CC15679A.

Rajca et al., Correction to organic radical contrast agents for magnetic resonance imaging. J Am Chem Soc. Feb. 26, 2014;136(8):3318. doi: 10.1021/ja413028d. Epub Feb. 17, 2014.

Rajca et al., Organic radical contrast agents for magnetic resonance imaging. J Am Chem Soc. Sep. 26, 2012;134(38):15724-7. Epub Sep. 17, 2012.

Ratnakar et al., Modulation of CEST images in vivo by T1 relaxation: a new approach in the design of responsive PARACEST agents. J Am Chem Soc. Oct. 9, 2013;135(40):14904-7. doi: 10.1021/ja406738y. Epub Sep. 25, 2013.

Reboul et al., Mesoscopic architectures of porous coordination polymers fabricated by pseudomorphic replication. Nat Mater. Jun. 24, 2012;11(8):717-23. doi: 10.1038/nmat3359.

Ren et al., Organic Catalyst-Mediated Ring-Opening Polymerization for the Highly Efficient Synthesis of Polyester-Based Star Polymers. ACS Macro Lett., 2012;1(6):681-686. DOI: 10.1021/mz300169m.

Ren et al., Star Polymers. Chem Rev. Jun. 22, 2016;116(12):6743-836. doi: 10.1021/acs.chemrev.6b00008. Epub Jun. 14, 2016.

Ren et al., Synthetic Strategies towards Well-Defined Complex Polymeric Architectures through Covalent Chemistry. Chemie Ingenieur Technik, 86: 2195-2214. doi:10.1002/cite.201400088.

Rizzo et al., In vivo nanotoxicity testing using the zebrafish embryo assay. J. Mater. Chem. B, 2013,1, 3918-3925. DOI: 10.1039/C3TB20528B.

Rodenas et al., Metal-organic framework nanosheets in polymer composite materials for gas separation. Nat Mater. Jan. 2015;14(1):48-55. doi: 10.1038/nmat4113. Epub Nov. 2, 2014.

Rolfe et al., Multimodal polymer nanoparticles with combined 19F magnetic resonance and optical detection for tunable, targeted, multimodal imaging in vivo. J Am Chem Soc. Feb. 12, 2014;136(6):2413-9. doi: 10.1021/ja410351h. Epub Jan. 29, 2014.

Ronson et al., Metal-organic container molecules through subcomponent self-assembly. Chem Commun (Camb). Mar. 28, 2013;49(25):2476-90. doi: 10.1039/c2cc36363a.

Rowan et al., Metal-ligand induced supramolecular polymerization: a route to responsive materials. Faraday Discuss. 2005;128:43-53.

Roy et al., Cyclic β-Peptoids. Org. Lett., 2008;10(5):921-924. DOI: 10.1021/ol7030763.

(56) References Cited

OTHER PUBLICATIONS

Rzayev et al., Molecular Bottlebrushes: New Opportunities in Nanomaterials Fabrication. ACS Macro Lett., 2012;1(9):1146-1149. DOI: 10.1021/mz300402x.
Saini et al., Pd(0)-catalyzed 1,1-diarylation of ethylene and allylic carbonates. Org Lett. Oct. 4, 2013;15(19):5008-11. doi: 10.1021/ol4023358. Epub Sep. 18, 2013.
Samuni et al., Factors influencing nitroxide reduction and cytotoxicity in vitro. Antioxid Redox Signal. Jun. 2004;6(3):587-95.
Sancey et al., Long-term in vivo clearance of gadolinium-based AGuIX nanoparticles and their biocompatibility after systemic injection. ACS Nano. Mar. 24, 2015;9(3):2477-88. doi: 10.1021/acsnano.5b00552. Epub Feb. 26, 2015.
Sanders et al., Metal-free sequential [3+2]-dipolar cycloadditions using cyclooctynes and 1,3-dipoles of different reactivity. J Am Chem Soc. Feb. 2, 2011;133(4):949-57. doi: 10.1021/ja1081519. Epub Dec. 23, 2010.
Sartori et al., Nitroxide paramagnet-induced para-ortho conversion and nuclear spin relaxation of H2 in organic solvents. J Am Chem Soc. Sep. 24, 2008;130(38):12752-6. doi: 10.1021/ja8037195. Epub Aug. 20, 2008.
Sato et al., Remarkable stabilization of M(12)L(24) spherical frameworks through the cooperation of 48 Pd(II)-pyridine interactions. J Am Chem Soc. May 6, 2009;131(17):6064-5. doi: 10.1021/ja900676f.
Saunders et al., Synthesis of amphiphilic star block copolymers using ring-opening metathesis polymerization. Macromolecules, 1992;25(7):2055-2057. DOI: 10.1021/ma00033a035.
Schmidt et al., Supramolecular three-armed star polymers via cyclodextrin host—guest self-assembly. Polym. Chem., 2012;3:3139-3145. DOI: 10.1039/C2PY20293J.
Schukraft et al., Isoreticular expansion of polyMOFs achieves high surface area materials. Chem Commun (Camb). Sep. 26, 2017;53(77):10684-10687. doi: 10.1039/c7cc04222a.
Seitz et al., Self-Assembly and Stress Relaxation in Acrylic Triblock Copolymer Gels. Macromolecules, 2007;40(4):1218-26.
Semino et al., Microscopic Model of the Metal-Organic Framework/Polymer Interface: A First Step toward Understanding the Compatibility in Mixed Matrix Membranes. ACS Appl Mater Interfaces. Jan. 13, 2016;8(1):809-19. doi: 10.1021/acsami.5b10150. Epub Dec. 22, 2015.
Sengupta et al., Temporal targeting of tumour cells and neovasculature with a nanoscale delivery system. Nature. Jul. 28, 2005;436(7050):568-72.
Seredyuk et al., Spin-crossover and liquid crystal properties in 2D cyanide-bridged Fe(II)-M(I/II) metalorganic frameworks. Inorg Chem. Nov. 1, 2010;49(21):10022-31. doi: 10.1021/ic101304v.
Sheiko et al., Cylindrical molecular brushes: Synthesis, characterization, and properties. Progress in Polymer Science (Oxford), 33(7), 759-785. DOI: 10.1016/j.progpolymsci.2008.05.001.
Shellock et al., Safety of magnetic resonance imaging contrast agents. J Magn Reson Imaging. Sep. 1999;10(3):477-84.
Shi et al., Core cross-linked star (CCS) polymers with tunable polarity: synthesis by RAFT dispersion polymerization, self-assembly and emulsification. Polym. Chem., 2013;4:1950-1959. DOI: 10.1039/C3PY21120G.
Shi et al., Producing Small Domain Features Using Miktoarm Block Copolymers with Large Interaction Parameters. ACS Macro Lett., 2015;4(11):1287-92. DOI: 10.1021/acsmacrolett.5b00712.
Shibata et al., Quantitative Synthesis of Star-Shaped Poly(vinyl ether)s with a Narrow Molecular Weight Distribution by Living Cationic Polymerization. J. Am. Chem. Soc., 2006;128(23):7497-7504. DOI: 10.1021/ja057611h.
Shin et al., Recent advances in magnetic nanoparticle-based multimodal imaging. Chem Soc Rev. Jul. 21, 2015;44(14):4501-16. doi: 10.1039/c4cs00345d.
Skomski et al., Redox-active on-surface assembly of metal-organic chains with single-site Pt(II). J Am Chem Soc. Jul. 16, 2014;136(28):9862-5. doi: 10.1021/ja504850f. Epub Jul. 1, 2014.
Smith et al., Nanomaterials for In Vivo Imaging. Chem Rev. Feb. 8, 2017;117(3):901-986. doi: 10.1021/acs.chemrev.6b00073. Epub Jan. 3, 2017.
Smulders et al., Building on architectural principles for three-dimensional metallosupramolecular construction. Chem Soc Rev. Feb. 21, 2013;42(4):1728-54. doi: 10.1039/c2cs35254k. Epub Oct. 2, 2012.
Smulders et al., Integrative self-sorting synthesis of a Fe8Pt6L24 cubic cage. Angew Chem Int Ed Engl. Jul. 2, 2012;51(27):6681-5. doi: 10.1002/anie.201202050. Epub Jun. 5, 2012.
Sowers et al., Redox-responsive branched-bottlebrush polymers for in vivo MRI and fluorescence imaging. Nature Communications2014;5:Article No. 5460.
Spiniello et al., Synthesis and characterization of fluorescently labeled core cross-linked star polymers. J. Polym. Sci. A Polym. Chem., 2008;46:2422-2432. doi:10.1002/pola.22576.
Stadler et al., Formation of Rack- and grid-type metallosupramolecular architectures and generation of molecular motion by reversible uncoiling of helical ligand strands. Chemistry. Jun. 2, 2006;12(17):4503-22.
Stang et al., Self-Assembly, Symmetry, and Molecular Architecture: Coordination as the Motif in the Rational Design of Supramolecular Metallacyclic Polygons and Polyhedra. Acc. Chem. Res., 1997;30(12):502-18. DOI: 10.1021/ar9602011.
Stenzel-Rosenbaum et al., Synthesis of Poly(styrene) Star Polymers Grown from Sucrose, Glucose, and Cyclodextrin Cores via Living Radical Polymerization Mediated by a Half-Metallocene Iron Carbonyl Complex. Macromolecules, 2001;34(16):5433-5438. DOI: 10.1021/ma0021803.
Stock et al., Synthesis of Metal-Organic Frameworks (MOFs): Routes to Various MOF Topologies, Morphologies, and Composites. Chem. Rev., 2012;112(2):933-69.
Su et al., Coordination-directed assembly of trigonal and tetragonal molecular boxes encapsulating anionic guests. Journal of the Chemical Society, Dalton Transactions. 2001:359-361. doi: 10.1039/B010118O.
Sulistio et al., Star polymers composed entirely of amino acid building blocks: a route towards stereospecific, biodegradable and hierarchically functionalized stars. Chem. Commun., 2011;47:1151-1153. DOI: 10.1039/C0CC03541F.
Sun et al., Multicomponent metal-ligand self-assembly. Curr Opin Chem Biol. Dec. 2002;6(6):757-64.
Sun et al., Self-assembled M24L48 polyhedra and their sharp structural switch upon subtle ligand variation. Science. May 28, 2010;328(5982):1144-7. doi:10.1126/science.1188605. Epub Apr. 29, 2010.
Sveinbjornsson et al., Rapid self-assembly of brush block copolymers to photonic crystals. Proc Natl Acad Sci U S A. Sep. 4, 2012;109(36):14332-6. doi: 10.1073/pnas.1213055109. Epub Aug. 21, 2012.
Swaminathan et al., Nephrogenic systemic fibrosis, gadolinium, and iron mobilization. N Engl J Med. Aug. 16, 2007;357(7):720-2.
Takamizu et al., Synthesis of oligo(thiophene)-coated star-shaped ROMP polymers: unique emission properties by the precise integration of functionality. Journal of the American Chemical Society 2012;134(18):7892-7895.
Tam et al., Recent advances in metallogels. Chem Soc Rev. Feb. 21, 2013;42(4):1540-67. doi: 10.1039/c2cs35354g. Epub Jan. 8, 2013.
Terashima et al., Star-Polymer-Catalyzed Living Radical Polymerization: Microgel-Core Reaction Vessel by Tandem Catalyst Interchange. Angew. Chem., 2011;50:7892-7895. doi:10.1002/anie.201101381.
Terreno et al., Challenges for molecular magnetic resonance imaging. Chem Rev. May 12, 2010;110(5):3019-42. doi: 10.1021/cr100025t.
Thompson et al., Labelling polymers and micellar nanoparticles via initiation, propagation and termination with ROMP. Polym. Chem., 2014;5:1954-1964.
Tirotta et al., (19)F magnetic resonance imaging (MRI): from design of materials to clinical applications. Chem Rev. Jan. 28, 2015;115(2):1106-29. doi: 10.1021/cr500286d. Epub Oct. 20, 2014.

(56) References Cited

OTHER PUBLICATIONS

Tolmasoff et al., Superoxide dismutase: correlation with life-span and specific metabolic rate in primate species. Proc Natl Acad Sci U S A. May 1980;77(5):2777-81.

Tominaga et al., Finite, spherical coordination networks that self-organize from 36 small components. Angew Chem Int Ed Engl. Oct. 25, 2004;43(42):5621-5.

Torchilin, Tumor delivery of macromolecular drugs based on the EPR effect. Adv Drug Deliv Rev. Mar. 18, 2011;63(3):131-5. doi: 10.1016/j.addr.2010.03.011. Epub Mar. 18, 2010.

Tsuji et al., Facile Palladium catalyzed decarboxylative allylation of active methylene compounds under neutral conditions using allylic carbonates. Tetrahedron Letters. 1982;23(46):4809-12.

Tu et al., Multimodal magnetic-resonance/optical-imaging contrast agent sensitive to NADH. Angew Chem Int Ed Engl. 2009;48(35):6547-51. doi: 10.1002/anie.200900984.

Tunca et al., Novel miktofunctional initiator for the preparation of an ABC-type miktoarm star polymer via a combination of controlled polymerization techniques. J. Polym. Sci. A Polym. Chem., 42: 4228-4236. doi:10.1002/pola.20284.

Uemura et al., Polymerization reactions in porous coordination polymers. Chem Soc Rev. May 2009;38(5):1228-36. doi: 10.1039/b802583p. Epub Feb. 3, 2009.

Valeur et al., Amide bond formation: beyond the myth of coupling reagents. Chem. Soc. Rev., 2009;38:606-631. DOI: 10.1039/B701677H.

Van Genabeek et al., Synthesis and Self-Assembly of Discrete Dimethylsiloxane-Lactic Acid Diblock Co-oligomers: The Dononacontamer and Its Shorter Homologues. J Am Chem Soc. Mar. 30, 2016;138(12):4210-8. doi: 10.1021/jacs.6b00629. Epub Mar. 21, 2016.

Verduzco et al., Correction: Structure, function, self-assembly, and applications of bottlebrush copolymers. Chem Soc Rev. Nov. 7, 2015;44(21):7916. doi: 10.1039/c5cs90099a.

Verwilst et al., Recent advances in Gd-chelate based bimodal optical/MRI contrast agents. Chem Soc Rev. Apr. 7, 2015;44(7):1791-806. doi: 10.1039/c4cs00336e. Epub Jan. 27, 2015.

Villaraza et al., Macromolecules, dendrimers, and nanomaterials in magnetic resonance imaging: the interplay between size, function, and pharmacokinetics. Chem Rev. May 12, 2010;110(5):2921-59. doi: 10.1021/cr900232t.

Wang et al., A supramolecular approach to combining enzymatic and transition metal catalysis. Nat Chem. Feb. 2013;5(2):100-3. doi: 10.1038/nchem.1531. Epub Jan. 6, 2013.

Wang et al., Advances of cancer therapy by nanotechnology. Cancer Res Treat. Mar. 2009;41(1):1-11. doi: 10.4143/crt.2009.41.1.1. Epub Mar. 31, 2009.

Wang et al., Block Co-PolyMOCs by Stepwise Self-Assembly. J Am Chem Soc. Aug. 24, 2016;138(33):10708-15. doi: 10.1021/jacs.6b06712. Epub Aug. 16, 2016.

Wang et al., Postsynthetic modification of metal-organic frameworks. Chem Soc Rev. May 2009;38(5):1315-29. doi: 10.1039/b802258p. Epub Jan. 20, 2009.

Wang et al., Star PolyMOCs with Diverse Structures, Dynamics, and Functions by Three-Component Assembly. Angew Chem Int Ed Engl. Jan. 2, 2017;56(1):188-192. doi: 10.1002/anie.201609261. Epub Dec. 5, 2016.

Wang et al., Synthesis of Unnatural Amino Acids Functionalized with Sterically Shielded Pyrroline Nitroxides. Org Lett. Oct. 17, 2014;16(20): 5298-5300. Published online Sep. 16, 2014. doi: [10.1021/ol502449r].

Wei et al., Exceedingly small iron oxide nanoparticles as positive MRI contrast agents. Proc. Natl. Acad. Sci. USA 2017;114(9):2325-2330.

Weng et al., Control of Gel Morphology and Properties of a Class of Metallo-Supramolecular Polyers by Good/Poor Solvent Environments. Macromolecules. 2009;42(1):236-246.

Weng et al., Effect of monomer structure on the gelation of a class of metallo-supramolecular polymers. Soft Matter. 2009;5(23):4647-4657.

Weng et al., Structural origin of the thixotropic behavior of a class of metallosupramolecular gels. Tetrahedron. Jul. 30, 2007;63(31):7419-7431.

Weng et al., Understanding the mechanism of gelation and stimuli-responsive nature of a class of metallo-supramolecular gels. J Am Chem Soc. Sep. 6, 2006;128(35):11663-72.

Westhaus et al., Triggered release of calcium from lipid vesicles: a bioinspired strategy for rapid gelation of polysaccharide and protein hydrogels. Biomaterials. Mar. 2001;22(5):453-62.

Wollinsky et al., Therapeutic and diagnostic applications of dendrimers for cancer treatment. Adv Drug Deliv Rev. Jun. 10, 2008;60(9):1037-55. doi: 10.1016/j.addr.2008.02.012. Epub Mar. 4, 2008.

Wong et al., Quantitative formation of core cross-linked star polymers via a one-pot two-step single electron transfer-living radical polymerization. Polym. Chem., 2013;4:4562-4565. DOI: 10.1039/C3PY00726J.

Wood et al., Two-stage directed self-assembly of a cyclic [3]catenane. Nat Chem. Apr. 2015;7(4):354-8. doi: 10.1038/nchem.2205.

Worrell et al., Direct evidence of a dinuclear copper intermediate in Cu(I)-catalyzed azide-alkyne cycloadditions. Science. Apr. 26, 2013;340(6131):457-60. doi: 10.1126/science.1229506. Epub Apr. 4, 2013.

Xia et al., Efficient synthesis of narrowly dispersed brush copolymers and study of their assemblies: the importance of side chain arrangement. J Am Chem Soc. Dec. 30, 2009;131(51):18525-32. doi: 10.1021/ja908379q.

Xia et al., Efficient Synthesis of Narrowly Dispersed Brush Polymers via Living Ring-Opening Metathesis Polymerization of Macromonomers. Macromolecules, 2009;42(11):3761-3766. DOI: 10.1021/ma900280c.

Xia et al., EPR study of spin labeled brush polymers in organic solvents. J Am Chem Soc. Dec. 14, 2011;133(49):19953-9. doi: 10.1021/ja2085349. Epub Nov. 21, 2011.

Xiao et al., The use of polymeric platinum(IV) prodrugs to deliver multinuclear platinum(II) drugs with reduced systemic toxicity and enhanced antitumor efficacy. Biomaterials. Nov. 2012;33(33):8657-69. doi: 10.1016/j.biomaterials.2012.08.015. Aug. 28, 2012.

Xie et al., Construction of a highly symmetric nanosphere via a one-pot reaction of a tristerpyridine ligand with Ru(II). J Am Chem Soc. Jun. 11, 2014;136(23):8165-8. doi: 10.1021/ja502962j. Epub May 22, 2014.

Xie et al., Hydrophobic-Driven, Metallomacrocyclic Assembly—Towards Quantitative Construction. Eur. J. Inorg. Chem. 2016;11:1671-7.

Xie et al., Precise Molecular Fission and Fusion: Quantitative Self-Assembly and Chemistry of a Metallo-Cuboctahedron. Angew. Chem., 2015;54:9224-9.

Xing et al., A stable metal coordination polymer gel based on a calix[4]arene and its 'uptake' of non-ionic organic molecules from the aqueous phase. Chem Commun (Camb). Feb. 21, 2002;(4):362-3.

Xing et al., Design of coordination polymer as stable catalytic systems. Chemistry. Nov. 4, 2002;8(21):5028-32.

Xing et al., Spontaneous Enrichment of Organic Molecules from Aqueous and Gas Phases into a Stable Metallogel. Langmuir. 2002;18:9654-9658.

Xu et al., Mechanism of Shear Thickening in Reversibly Cross-linked Supramolecular Polymer Networks. Macromolecules. Apr. 13, 2010;43(7):3556-3565.

Xu et al., Scaling Laws in Supramolecular Polymer Networks. Macromolecules. 2011;44(13):5465-5472.

Xu et al., Strain Hardening and Strain Softening of Reversibly Cross-linked Supramolecular Polymer Networks. Macromolecules. Sep. 27, 2011;44(18):7478-7488.

Yamazaki et al., Dynamic Viscoelasticity of Poly(butyl acrylate) Elastomers Containing Dangling Chains with Controlled Lengths. Macromolecules, 2011;44(22):8829-34. DOI: 10.1021/ma201941v.

Yan et al., Hierarchical self-assembly: well-defined supramolecular nanostructures and metallohydrogels via amphiphilic discrete organoplatinum(II) metallacycles. J Am Chem Soc. Sep. 25, 2013;135(38):14036-9. doi: 10.1021/ja406877b. Epub Aug. 8, 2013.

(56) References Cited

OTHER PUBLICATIONS

Yan et al., Particle carriers for combating multidrug-resistant cancer. ACS Nano. Nov. 26, 2013;7(11):9512-7. doi: 10.1021/nn405632s. Epub Nov. 11, 2013.
Yan et al., Responsive supramolecular polymer metallogel constructed by orthogonal coordination-driven self-assembly and host/guest interactions. J Am Chem Soc. Mar. 26, 2014;136(12):4460-3. doi: 10.1021/ja412249k. Epub Mar. 12, 2014.
Yan et al., Supramolecular polymers with tunable topologies via hierarchical coordination-driven self-assembly and hydrogen bonding interfaces. Proc Natl Acad Sci U S A. Sep. 24, 2013;110(39):15585-90. doi: 10.1073/pnas.1307472110. Epub Sep. 9, 2013.
Yang et al., Luminescent chemodosimeters for bioimaging. Chem Rev. Jan. 9, 2013;113(1):192-270. doi: 10.1021/cr2004103. Epub Jun. 18, 2012.
Yang et al., Supramolecular Polymers: Historical Development, Preparation, Characterization, and Functions. Chem Rev. Aug. 12, 2015;115(15):7196-239. doi: 10.1021/cr500633b. Epub Mar. 13, 2015.
Yoneya et al., Coordination-directed self-assembly of M12L24 nanocage: effects of kinetic trapping on the assembly process. ACS Nano. Feb. 25, 2014;8(2):1290-6. doi: 10.1021/nn404595j. Epub Jan. 31, 2014.
Yoneya et al., Simulation of metal-ligand self-assembly into spherical complex M6L8. J Am Chem Soc. Sep. 5, 2012;134(35):14401-7. doi: 10.1021/ja303542r. Epub Aug. 22, 2012.
Yoshizawa et al., Molecular architectures of multi-anthracene assemblies. Chem Soc Rev. Mar. 21, 2014;43(6):1885-98. doi: 10.1039/c3cs60315f.
You et al., Manganese displacement from Zinpyr-1 allows zinc detection by fluorescence microscopy and magnetic resonance imaging. Chem Commun (Camb). Jun. 21, 2010;46(23):4139-41. doi: 10.1039/c0cc00179a. Epub May 10, 2010.
Yount et al., Small-molecule dynamics and mechanisms underlying the macroscopic mechanical properties of coordinatively cross-linked polymer networks. J Am Chem Soc. Oct. 19, 2005;127(41):14488-96.
Yount et al., Strong means slow: dynamic contributions to the bulk mechanical properties of supramolecular networks. Angew Chem Int Ed Engl. Apr. 29, 2005;44(18):2746-8.
Yue et al., Macrocyclic and lantern complexes of palladium(II) with bis(amidopyridine) ligands: synthesis, structure, and host-guest chemistry. Inorg Chem. Nov. 29, 2004;43(24):7671-81.
Zhang et al., Active cross-linkers that lead to active gels. Angew Chem Int Ed Engl. Oct. 25, 2013;52(44):11494-8. doi: 10.1002/anie.201304437. Epub Sep. 12, 2013.
Zhang et al., Challenges and recent advances in MOF-polymer composite membranes for gas separation. Inorg. Chem. Front., 2016;3:896-909. DOI: 10.1039/C6QI00042H.
Zhang et al., Cyclodextrin-centred star polymers synthesized via a combination of thiol-ene click and ring opening polymerization. Chem Commun (Camb). Aug. 21, 2012;48(65):8063-5. doi: 10.1039/c2cc33742h. Epub Jul. 6, 2012.
Zhang et al., Dual-functional gadolinium-based copper(II) probe for selective magnetic resonance imaging and fluorescence sensing. Inorg Chem. Feb. 20, 2012;51(4):2325-31. doi: 10.1021/ic202322f. Epub Feb. 8, 2012.
Zhang et al., Metal-organic gels: From discrete metallogelators to coordination polymers. Coordination Chemistry Reviews Apr. 2013;257(7-8):1373-1408.
Zhang et al., One-pot RAFT synthesis of core cross-linked star polymers of polyPEGMA in water by sequential homogeneous and heterogeneous polymerizations. Polym. Chem., 2012;3:2656-2664. DOI: 10.1039/C2PY20442H.
Zhang et al., Polymer-Metal-Organic Frameworks (polyMOFs) as Water Tolerant Materials for Selective Carbon Dioxide Separations. J Am Chem Soc. Jan. 27, 2016;138(3):920-5. doi: 10.1021/jacs.5b11034. Epub Jan. 13, 2016.
Zhang et al., polyMOFs: A Class of Interconvertible Polymer-Metal-Organic-Framework Hybrid Materials. Angew Chem Int Ed Engl. May 18, 2015;54(21):6152-7. doi: 10.1002/anie.201502733. Epub Apr. 29, 2015.
Zhang et al., Redox-Responsive, Core Cross-Linked Polyester Micelles. ACS Macro Lett., 2013;2(1):40-44. DOI: 10.1021/mz300522n.
Zhao et al., Chiral amide directed assembly of a diastereo- and enantiopure supramolecular host and its application to enantioselective catalysis of neutral substrates. J Am Chem Soc. Dec. 18, 2013;135(50):18802-5. doi: 10.1021/ja411631v. Epub Dec. 5, 2013.
Zhao et al., Rheological Behavoir of Shear-Responsive Metallo-Supramolecular Gels. Macromolecules. 2004;37(10):3529-3531.
Zhelev et al., Imaging of superoxide generation in the dopaminergic area of the brain in Parkinson's disease, using mito-TEMPO. ACS Chem Neurosci. Nov. 20, 2013;4(11):1439-45. doi: 10.1021/cn400159h. Epub Sep. 16, 2013.
Zhelev et al., Nitroxyl radicals as low toxic spin-labels for non-invasive magnetic resonance imaging of blood-brain barrier permeability for conventional therapeutics. Chem Commun (Camb). Jan. 7, 2009;(1):53-5. doi: 10.1039/b816878d. Epub Nov. 13, 2008.
Zhelev et al., Nitroxyl radicals for labeling of conventional therapeutics and noninvasive magnetic resonance imaging of their permeability for blood-brain barrier: relationship between structure, blood clearance, and MRI signal dynamic in the brain. Mol Pharm. Mar.-Apr. 2009;6(2):504-12. doi: 10.1021/mp800175k.
Zhou et al., Counting primary loops in polymer gels. Proc Natl Acad Sci U S A. Nov. 20, 2012;109(47):19119-24. doi: 10.1073/pnas.1213169109. Epub Nov. 6, 2012.
Zhou et al., Introduction to metal-organic frameworks. Chem Rev. Feb. 8, 2012;112(2):673-4. doi: 10.1021/cr300014x. Epub Jan. 26, 2012.
Zhou et al., Photo-controlled growth of telechelic polymers and end-linked polymer gels. Angew Chem Int Ed Engl. Feb. 18, 2013;52(8):2235-8. doi: 10.1002/anie.201207966. Epub Jan. 17, 2013.
Zhukhovitskiy et al., Highly branched and loop-rich gels via formation of metal-organic cages linked by polymers. Nat Chem. Jan. 2016;8(1):33-41. doi: 10.1038/nchem.2390. Epub Nov. 16, 2015.
Zhukhovitskiy et al., Polymer Structure Dependent Hierarchy in PolyMOC Gels. Macromolecules, 2016;49(18):6896-902.
International Search Report for PCT/US2017/48641, dated Nov. 9, 2017.
Burts et al., Using EPR to Compare PEG-branch-nitroxide "Bivalent-Brush Polymers" and Traditional PEG Bottle-Brush Polymers: Branching Makes a Difference. Macromolecules 2012;45(20):8310-8. DOI: 10.1021/ma301874d.
Gestwicki et al., Influencing receptor-ligand binding mechanisms with multivalent ligand architecture. J Am Chem Soc. Dec. 18, 2002;124(50):14922-33.
PCT/US2017/055145, dated Jan. 23, 2018, International Search Report and Written Opinion.
PCT/US2017/044259, dated Nov. 8, 2017, Invitation to Pay Additional Fees.
PCT/US2017/044259, dated Jan. 9, 2018, International Search Report and Written Opinion.
U.S. Appl. No. 15/662,239, filed Jul. 27, 2017, Johnson et al.
PCT/US2017/48641, dated Nov. 9, 2017, International Search Report.
U.S. Appl. No. 14/249,254, filed Apr. 9, 2014, Johnson et al.
U.S. Appl. No. 15/190,018, filed Jun. 22, 2016, Johnson et al.
U.S. Appl. No. 16/231,166, filed Dec. 21, 2018, Johnson et al.
U.S. Appl. No. 15/616,498, filed Jun. 7, 2017, Johnson et al.
U.S. Appl. No. 16/167,412, filed Oct. 22, 2018, Johnson et al.
U.S. Appl. No. 16/080,503, filed Aug. 28, 2018, Johnson et al.
U.S. Appl. No. 16/024,665, filed Jun. 29, 2018, Johnson et al.
U.S. Appl. No. 16/024,643, filed Jun. 29, 2018, Johnson et al.
U.S. Appl. No. 16/024,662, filed Jun. 29, 2018, Johnson et al.
EP 14782253.0, dated Nov. 11, 2016, Extended European Search Report.
PCT/US2014/033554, dated Oct. 22, 2015, International Preliminary Report on Patentability.
PCT/US2014/033554, dated Aug. 29, 2014, International Search Report and Written Opinion.

(56) References Cited

OTHER PUBLICATIONS

PCT/US2015/015032, dated May 8, 2015, International Search Report and Written Opinion.
PCT/US2015/015032, dated Aug. 18, 2016, International Preliminary Report on Patentability.
PCT/US2017/036447, dated Sep. 7, 2017, International Search Report and Written Opinion.
PCT/US2017/036447, dated Dec. 20, 2018, International Preliminary Report on Patentability.
PCT/US2017/055145, dated Apr. 18, 2019, International Preliminary Report on Patentability.
PCT/US2017/064784, dated Mar. 1, 2018, International Search Report and Written Opinion.
PCT/US2017/48641, dated Mar. 7, 2019, International Preliminary Report on Patentability.
PCT/US2017/04425, dated Feb. 7, 2019, International Preliminary Report on Patentability.
PCT/US2018/040488, dated Oct. 15, 2018, International Search Report and Written Opinion.
PCT/US2018/040494, dated Oct. 10, 2018, International Search Report and Written Opinion.
PCT/US2018/040496, dated Jan. 14, 2019, International Search Report and Written Opinion.

* cited by examiner

| Sample | blank | dexamethasone | ibuprofen | ofloxacin |
|---|---|---|---|---|
| z-aver. size | 85.6 ± 0.9 | 92.2 ± 0.2 | 108.2 ± 1.2 | 113.5 ± 3.0 |
| PDI | 0.11 ± 0.05 | 0.10 ± 0.01 | 0.09 ± 0.03 | 0.16 ± 0.03 |

| Entry | Copolymer | $N_{(PLA\ 6.7K)}{}^a$ | $N_{(PEO\ 3.4K)}{}^a$ | $N_{(PNIPAM\ 8.4K)}{}^a$ | MW(kg/mol)$^b$ | $D_h$ (nm) | PDI |
|---|---|---|---|---|---|---|---|
| AB | PLA-b-PEG | 10 | 40 | 0 | 203 | 90 | 0.13 |
| CB | PNP-b-PEG | - | 40 | 10 | 220 | - | - |
| ABC | PLA-b-PEG-b-PNP | 10 | 40 | 10 | 287 | 113 | 0.11 |
| CBA | PNP-b-PEG-b-PLA | 10 | 40 | 10 | 287 | 120 | 0.14 |
| ABC-ran | PLA-co-PEG-co-PNP | 10 | 40 | 10 | 287 | - | - |
| $A_xBC$ | PLA-b-PEG-b-PNP | 14 | 40 | 10 | 314 | 174 | 0.16 |
| CBC | PNP-b-PEG-b-PNP | - | 40 | 20 | 304 | - | - |
| CB-ran | PNP-co-PEG | - | 40 | 20 | 304 | - | - |

BOTTLEBRUSH COPOLYMERS AND USES THEREOF

RELATED APPLICATIONS

This application claims priority under 35 U.S.C. § 119(e) to U.S. Provisional Patent Application, U.S. Ser. No. 62/404,098, filed Oct. 4, 2016, the entire contents of which is incorporated herein by reference.

BACKGROUND OF THE INVENTION

Bottlebrush polymers (also referred to a polymer brushes) are macromolecules comprising polymeric sidechains attached to a linear polymeric backbone. Bottlebrush polymers are types of branched or graft polymer, and have unique properties due to their highly branched structure. The high molecular weight and high sidechain grafting density typical of bottlebrush polymers can allow these macromolecules to self-assemble into well-defined structures with large domain sizes. Such properties give these polymers potential applications in, e.g., photonics, chromatography media, stimuli-responsive materials, lubricants, nanolithography, films, coatings, and drug delivery.

Bottlebrush copolymers are bottlebrush polymers comprising two or more different polymeric sidechains (i.e., two or more sidechains of different polymeric composition). These copolymers can be block copolymers, or copolymers wherein the polymeric sidechains are mixed and/or randomly dispersed. For a review on the structure, function, self-assembly, and applications of bottlebrush polymers, see, e.g., Verduzco et al. *Chem. Soc. Rev.* 2015, 44, 2405-2420, and references cite therein; the entire contents of which are incorporated herein by reference.

Extended release (also referred to as controlled release, sustained release, or time release) technologies allow for the slowed, steadied release of therapeutic agents over an extended period of time. Formulations for extended release of therapeutic agents (e.g., drugs) allow for less frequent dosing or administration, and therefore can increase patient compliance and convenience. Furthermore, implantable materials with extended release characteristics allow for the local administration of therapeutic agents for sustained release to a site of interest. For example, injectable or implantable gels with extended release properties can be administered to the eye of a subject to aid in healing after ocular surgery. As another example, injectable gels can be administered to a tumor site for localized and sustained release of chemotherapeutic agents for the treatment of cancer.

Polymers are useful materials in extended release formulations due to their ability to organize into structures capable of encapsulating, carrying, and/or delivering therapeutic agents. For instance, polymers are known to organize to form particles, micelles, and hydrogels with interesting and attractive drug delivery characteristics, including extended release properties.

Injectable hydrogels based on polymer scaffolds have been reported for non-covalent loading of cargo of various ionic drugs, proteins, and RNAs, and hydrophobic small molecules. Generally, the therapeutic cargo diffuses out of the hydrogel and enters the extracellular matrix; the rate of release is controlled by carrier density and biodegradation. The drug release profiles in vivo from the hydrogels can be tuned by altering the underlying carrier design at molecular level. Of particular interest are polymer systems that are designed to exhibit stimulus-responsive behavior and provide control over the place and duration of drug release. Examples are drug-loaded hydrogels that are modulated or degraded by ECM enzymes, pH, and body heat. In the last group, heat-induced physical crosslinking of drug-loaded micelle solutions is underexplored field and can offer innovative ways of tuning the rate of drug diffusion from carrier hydrogel. New bottlebrush polymers with tunable properties are of great interest. In particular, new bottlebrush polymers capable of forming particles and/or hydrogels have important applications in medicine (e.g., drug delivery).

SUMMARY OF THE INVENTION

Thermally-responsive nanomaterials (e.g., particles, hydrogels) that provide extended release of one or more therapeutic agents are useful platforms for drug delivery, and thermally-responsive bottlebrush copolymers are macromolecules which can be used in the formulation of such materials.

In part, the present invention relates to new triblock bottlebrush copolymers which are useful in biomedical and other applications (e.g., photonics, chromatography media, stimuli-responsive materials, lubricants, nanolithography, films, coatings). In certain embodiments, the triblock bottlebrush copolymers described herein can be used in the formulation of particles and hydrogels useful in the extended release of one or more therapeutic agents, and can be administered to a subject to provide extended release of one or more therapeutic agents to the subject. In certain embodiments, the triblock bottlebrush copolymers, particles, and hydrogels described herein are thermally-responsive and gel at physiological temperature (e.g., upon administration to a subject), providing injectable and/or implantable gels (e.g., for controlled release drug delivery).

In one aspect, the present invention provides triblock bottlebrush copolymers (e.g., ABC triblock bottlebrush copolymers). An ABC triblock bottlebrush copolymer of the present invention comprises a backbone polymer of repeating units covalently linked to polymeric sidechains; wherein Block A, Block B, and Block C of the copolymer comprise polymeric sidechains covalently linked to the repeating units of the backbone polymer; and wherein at least one of Block A, Block B, and Block C comprises polymeric sidechains that exhibit lower critical solution temperature (LCST) behavior. Lower critical solution temperature behavior is defined and described herein. In certain embodiments, at least one of Block A, Block B, and Block C comprises polymeric sidechains that exhibit an LCST around physiological temperature (approximately 37° C.).

In certain embodiments, one or more of Block A, Block B, and Block C of the triblock bottlebrush copolymer comprise polyester sidechains (e.g., polylactic acid sidechains). In certain embodiments, one or more of Block A, Block B, and Block C of the triblock bottlebrush copolymer comprise polyether sidechains (e.g., polyethylene glycol sidechains). As described herein, at least one of Block A, Block B, and Block C of the triblock bottlebrush copolymer comprises polymeric sidechains that exhibit LCST behavior (e.g., poly(N-alkylacrylamide) sidechains such as poly(N-isopropylacrylamide) sidechains).

Poly(N-isopropyl)acrylamide (PNIPAM) sidechains may be incorporated into the ABC bottlebrush copolymers described herein. In some instances, poly(N-isopropyl) acrylamide (PNIPAM) polymers form solutions that can be handled with ease at room temperature. When heated to above its lower critical solution temperature (LCST) of 32° C., PNIPAM undergoes a reversible sol-gel transition, turning into a gel. Because of their thermoresponsive behavior at biologically relevant temperatures, coupled with established biocompatibility, PNIPAM-containing polymeric structures are important thermoresponsive materials with medicinal applications.

In certain embodiments, a triblock bottlebrush copolymer of the present invention is of Formula (I):

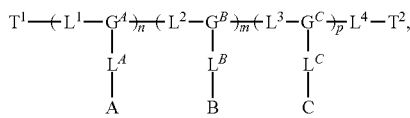

(I)

wherein $G^A$, $G^B$, $G^C$, $L^1$, $L^2$, $L^3$, $L^4$, $L^A$, $L^B$, $L^C$, $T^1$, $T^2$, n, m, and p are as defined herein;
  each of A, B, and C is independently a polymer;
  wherein all of A are the same polymer, all of B are the same polymer, and all of C are the same polymer;
  provided that A, B, and C are different polymers; and
  provided that at least one of A, B, and C is a polymer that exhibits LCST behavior.

"Same polymer," as used here, refers to the same polymer composition (i.e., composed of the same monomer subunits). Polymers that are the "same polymer" can have different polymer lengths, molecular weight, terminal groups, etc. For instance, all of A are considered to be the "same polymer" if all of A are polylactic acid (PLA) side chains, even if each A is a PLA side chain with a different length and molecular weight. "Different polymer," as used herein, refers to different polymer composition (i.e., composed of different monomer subunits). Polymers that are different are of a different polymer type and/or of a different polymer class. For instance, when each A is independently a PLA polymer and each of B is independently a polyethylene glycol (PEG) polymer, A and B are considered to be different polymer types, of different polymer classes, and different polymers.

In certain embodiments, the triblock bottlebrush copolymer of Formula (I) is a triblock bottlebrush copolymer of Formula (I-d):

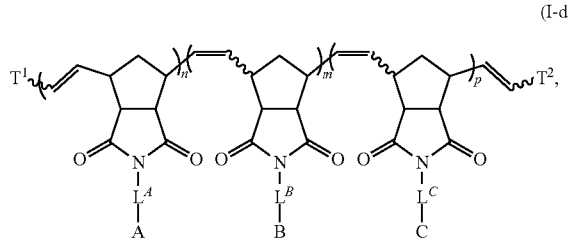

(I-d)

wherein $T^1$, $T^2$, $L^A$, $L^B$, $L^C$, A, B, C, n, m, and p are as defined herein.

In certain embodiments, one or more of group A, group B, and group C is a polyester (e.g., polylactic acid). In certain embodiments, one or more of group A, group B, and group C is a polyether (e.g., polyethylene glycol, polypropylene glycol). As described herein, at least one of group A, group B, and group C of the triblock bottlebrush copolymer is a polymer that exhibit LCST behavior (e.g., poly(N-alkylacrylamide), such as poly(N-isopropylacrylamide)).

For example, in particular embodiments, a triblock bottlebrush copolymer provided herein is of the following formula:

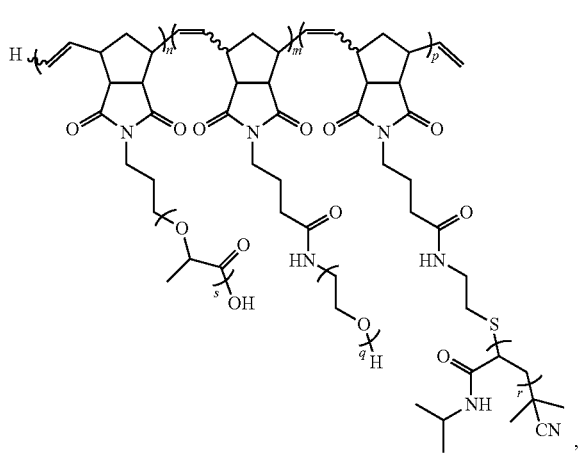

wherein n, m, p, s, r, and q are as defined herein.

As another example, in another particular embodiment, a triblock bottlebrush copolymer provided herein is of the following formula:

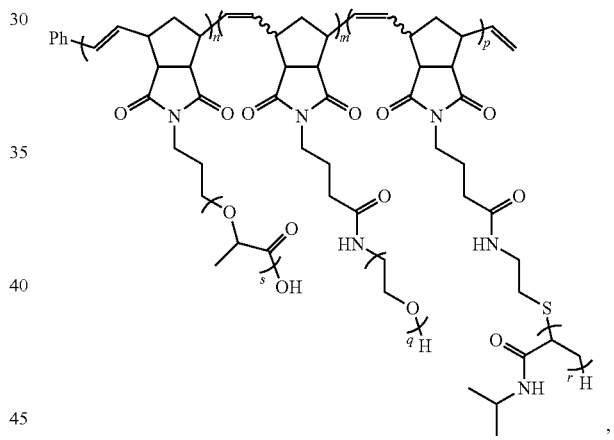

wherein n, m, p, s, r, and q are as defined herein.

The present invention also provides methods of preparing triblock bottlebrush copolymers described herein via polymerization reactions. In certain embodiments, a method for preparing a triblock bottlebrush copolymer described herein comprises polymerizing three different macromonomers using ring-opening metathesis ("ROMP") polymerization.

As described herein, a triblock bottlebrush copolymer of the present invention may self-assemble to form a structure, such as a particle (e.g., micelle, nanoparticle). Therefore, in another aspect, the present invention provides particles (e.g., micelles, nanoparticles) comprising a triblock bottlebrush copolymer described herein. A particle described herein may contain one or more therapeutic agents. In certain embodiments, the one or more therapeutic agents are small molecules (e.g., small molecule drugs). In certain embodiments, one or more of the therapeutic agents is selected from the group consisting of non-steroidal anti-inflammatory drugs (NSAIDs) (e.g., ibuprofen), steroids (e.g., corticosteroids such as dexamethasone), and antibiotics (e.g., ofloxacin).

The particles in certain embodiments comprise one or more anti-proliferative (e.g., anti-cancer) agents. Further examples of therapeutic agents and combinations thereof (e.g., three-way combinations, two-way combinations) are provided herein.

The triblock bottlebrush copolymers described herein, and the particles described herein, can self-assemble to form hydrogels. Therefore, in another aspect, the present invention provides hydrogels comprising a triblock bottlebrush copolymer described herein and/or a particle described herein. In certain embodiments, a hydrogel described herein undergoes a solution-gel ("sol-gel") phase transition in response to a change in temperature. In certain embodiments, a hydrogel described herein undergoes a sol-gel transition at or around physiological temperature (approximately 37° C.). Since in certain embodiments a hydrogel described herein can gel at a temperature near physiological temperature, hydrogels of the present invention are particularly useful in biomedical applications, including, but not limited to, implants and/or extended-release vehicles for the delivery of therapeutic agents.

In another aspect, the present invention provides formulations comprising the triblock bottlebrush copolymers, particles, and hydrogels described herein; optionally one or more therapeutic agents; and optionally a carrier or excipient. For example, in certain embodiments, a formulation provided herein comprises a triblock bottlebrush copolymer described herein, or particle or hydrogel thereof; and one or more therapeutic agents selected from NSAIDs (e.g., ibuprofen), steroids (e.g., corticosteroids such as dexamethasone), and antibiotics (e.g., ofloxacin); and a carrier (e.g., water, saline, buffered solutions). As another example, in certain embodiments, a formulation provided herein comprises a triblock bottlebrush copolymer described herein, or particle or hydrogel thereof; and one or more anti-cancer agents; and a carrier (e.g., water, saline, buffered solutions). Further examples of therapeutic agents and carriers are provided herein.

In certain embodiments, a formulation provide herein is tailored for ophthalmic use, e.g., for administration to the eye of a subject to treat an ocular condition and/or to aid in post-surgical ocular healing. In certain embodiments, a formulation provide herein is tailored for oncological use, e.g., for administration to the site of a tumor to aid in the treatment of cancer.

In yet another aspect, the present invention provides kits (e.g., pharmaceutical packs) comprising a triblock bottlebrush copolymer, particle, hydrogel, or formulation described herein; and optionally instructions for use.

The present invention provides methods for treating and/or preventing a disease or condition (e.g., ophthalmic condition, proliferative disease, diabetic condition) in a subject in need thereof, the methods comprising administering to the subject a particle, hydrogel, or formulation described herein. In certain embodiments, a particle, hydrogel, or formulation described herein constitutes an implantable material that provides extended release of one or more therapeutic agents to the subject, thereby treating and/or preventing the disease or condition. Therefore, the present invention provides methods for extended release of one or more therapeutic agents to a subject, the methods comprising administering a particle, hydrogel, or formulation described herein to a subject in need thereof.

The present invention also provides uses of triblock bottlebrush copolymers, particles, hydrogels, and/or formulations described herein for the treatment and/or prevention of a disease or condition in a subject in need thereof. For example, the invention provides uses of triblock bottlebrush copolymers, particles, hydrogels, and/or formulations described herein in the manufacture of a medicament for treating a disease or condition in a subject in need thereof.

A triblock bottlebrush copolymer described herein may be useful in biomedical applications other than drug delivery. For instance, a triblock bottlebrush copolymer, particle, or hydrogel of the present invention may be useful as a material (e.g., an injectable implant) for tissue or cartilage repair, cosmetic implantation, and lubrication/hydration of tissues or biological membranes. A triblock bottlebrush copolymer described herein may also be useful in non-biomedical applications, such as photonics (e.g., photonic crystals), functional materials, chromatography media, stimuli-responsive materials, lubricants, nanolithography, films, and coatings.

The details of certain embodiments of the invention are set forth herein. Other features, objects, and advantages of the invention will be apparent from the Detailed Description, Figures, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H., *Tables of Resolving Agents and Optical Resolutions*, p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⌇ is a single bond where the stereochemistry of the moieties immediately attached thereto is not specified, --- is absent or a single bond, and ═══ or ≡≡≡ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH$_3$ or

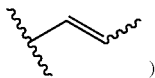 )

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl).

Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur. Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzo-thienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl. Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$), —P(R$^{cc}$)$_2$, —P(R$^{cc}$)$_3$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$alkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl), —N(C$_{1-6}$ alkyl), —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl), —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl), —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl), —C(=NH)NH(C$_{1-6}$ alkyl), —C(=NH)NH$_2$, —OC(=NH)N(C$_{1-6}$ alkyl), —OC(NH)NH(C$_{1-6}$ alkyl), —OC(NH)NH$_2$, —NHC(NH)N(C$_{1-6}$ alkyl), —NHC(=NH)NH$_2$, —NHSO$_2$(C$_{1-6}$ alkyl), —SO$_2$N(C$_{1-6}$ alkyl), —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl), C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl), —P(=O)(C$_{1-6}$ alkyl), —OP(=O)(C$_{1-6}$ alkyl), —OP(=O)(OC$_{1-6}$ alkyl), $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

In certain embodiments, carbon atom substituents include: halogen, —CN, —NO$_2$, —N$_3$, —SO$_2$H, —SO$_3$H, —OH, —OC$_{1-6}$ alkyl, —ON(C$_{1-6}$ alkyl), —N(C$_{1-6}$ alkyl), —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl), —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl), —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl), —C(=NH)NH(C$_{1-6}$ alkyl), —C(=NH)NH$_2$, —OC(=NH)N(C$_{1-6}$ alkyl), —OC(=NH)NH(C$_{1-6}$ alkyl), —OC(=NH)NH$_2$, —NHC(=NH)N(C$_{1-6}$ alkyl), —NHC(=NH)NH$_2$, —NHSO$_2$(C$_{1-6}$ alkyl), —SO$_2$N(C$_{1-6}$ alkyl), —SO$_2$NH(C$_{1-6}$ alkyl), —SO$_2$NH$_2$, —SO$_2$(C$_{1-6}$ alkyl), —SO$_2$O(C$_{1-6}$ alkyl), —OSO$_2$(C$_{1-6}$ alkyl), —SO(C$_{1-6}$ alkyl), —Si(C$_{1-6}$ alkyl), —OSi(C$_{1-6}$ alkyl)$_3$-C(=S)N(C$_{1-6}$ alkyl), C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3}$-10 carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(=O)(R$^{aa}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X$^-$ are as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{x1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

The term "silyl" refers to the group —Si(R$^{aa}$)$_3$, wherein R$^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 2-triphenylphosphonoisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3^+X^-$, $-P(OR^{cc})_2$, $-P(OR^{cc})_3^+X^-$, $-P(=O)(R^{aa})_2$, $-P(=O)(OR^{cc})_2$, and $-P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —$OC(=O)SR^{aa}$, —$OC(=O)R^{aa}$, —$OCO_2R^{aa}$, —$OC(=O)N(R^{bb})_2$, —$OC(=NR^{bb})R^{aa}$, —$OC(=NR^{bb})OR^{aa}$, —$OC(=NR^{bb})N(R^{bb})_2$, —$OS(=O)R^{aa}$, —$OSO_2R^{aa}$, —$OP(R^{cc})_2$, —$OP(R^{cc})_3$, —$OP(=O)_2R^{aa}$, —$OP(=O)(R^{aa})_2$, —$OP(=O)(OR^{cc})_2$, —$OP(=O)_2N(R^{bb})_2$, and —$OP(=O)(NR^{bb})_2$, wherein $R^{aa}$, $R^{bb}$, and $R^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

These and other exemplary substituents are described in more detail in the Detailed Description, Examples, and Claims. The invention is not intended to be limited in any manner by the above exemplary listing of substituents.

Other Definitions

The following definitions are more general terms used throughout the present application.

The term "polymer" refers to a molecule comprised of two or more (e.g., 10 or more) repeating units which are covalently bonded together. In certain embodiments, a polymer comprises 10 or more, 50 or more, 100 or more, 1000 or more, 2000 or more, or 4000 or more repeating units. In certain embodiments, a polymer comprises more than 4000 repeating units. The repeating units of a polymer are referred to as "monomers." A "homopolymer" is a polymer that consists of a single repeating monomer. A "copolymer" is a polymer that comprises two or more different monomer subunits. Copolymers include, but are not limited to, random, block, alternating, segmented, linear, branched, grafted, and tapered copolymers. Polymers may be natural (e.g., naturally occurring polypeptides), or synthetic (e.g., non-naturally occurring). A polymer may have an overall molecular weight of 50 Da or greater, 100 Da or greater, 500 Da or greater, 1000 Da or greater, 2000 Da or greater, 5000 Da or greater, 10000 Da or greater, 20000 Da or greater, or 50000 Da or greater.

"Block copolymers" are copolymers comprising homopolymer subunits (i.e., "blocks") covalently linked together. The blocks of a block copolymer are separated into distinct domains. A "diblock copolymer" is a block copolymer comprising two distinct homopolymer domains. A "triblock bottlebrush copolymer" is a block copolymer comprising three distinct homopolymer domains. Each distinct homopolymer domain of a block copolymer is of a different polymeric composition (e.g., comprising different repeating monomers). A triblock bottlebrush copolymer can be an "ABC triblock bottlebrush copolymer," defined as a copolymer comprising three blocks (Block A, Block B, and Block C), each of which is a distinct homopolymer domain with a different monomeric subunit.

The terms "bottlebrush polymer" or "polymer brush" refer to a polymer comprising a polymeric backbone of repeating units, wherein the repeating units of the polymeric backbone are covalently linked to polymeric sidechains. In certain embodiments, each repeating unit of the polymeric backbone is linked to a polymeric sidechain. In bottlebrush copolymers, the entire polymeric backbone may be composed a single repeating backbone unit, and the blocks of the copolymer are defined by the composition of the polymeric sidechains. For example, in an ABC triblock bottlebrush copolymer, the polymeric backbone may be composed of a single unit that repeats throughout the entire backbone of the polymer, and each of Block A, Block B, and Block C of the triblock bottlebrush copolymer comprise polymeric sidechains of a different polymeric composition (e.g., comprised of different monomers). In other embodiments, a bottlebrush copolymer comprises more than one monomeric subunit in its polymeric backbone. The polymeric sidechains of a bottlebrush polymer or copolymer can be homopolymers or copolymers, and can have linear or branched architectures.

As used herein, "therapeutic agent" refers to any substance used as a medicine for treatment, prevention, delay, reduction or amelioration of a disease, condition, or disorder, and refers to a substance that is useful for therapy, including prophylactic and therapeutic treatment. A biologically active agent also includes a compound that increases the effect or effectiveness of another compound, for example, by enhancing potency or reducing adverse effects of the other compound.

In certain embodiments, a therapeutic agent is an anti-cancer agent, antibiotic, anti-viral agent, anti-HIV agent, anti-parasite agent, anti-protozoal agent, anesthetic, anticoagulant, inhibitor of an enzyme, steroidal agent (e.g., corticosteroid), steroidal or non-steroidal anti-inflammatory agent (NSAID), antihistamine, immunosuppressant agent, anti-neoplastic agent, antigen, vaccine, antibody, decongestant, sedative, opioid, analgesic, anti-pyretic, birth control agent, hormone, prostaglandin, progestational agent, anti-glaucoma agent, ophthalmic agent, anti-cholinergic, analgesic, anti-depressant, anti-psychotic, neurotoxin, hypnotic, tranquilizer, anti-convulsant, muscle relaxant, anti-Parkinson agent, anti-spasmodic, muscle contractant, channel blocker, miotic agent, anti-secretory agent, anti-thrombotic agent, anticoagulant, anti-cholinergic, β-adrenergic blocking agent, diuretic, cardiovascular active agent, vasoactive agent, vasodilating agent, anti-hypertensive agent, angiogenic agent, modulators of cell-extracellular matrix interactions (e.g. cell growth inhibitors and anti-adhesion molecules); or inhibitors/intercalators of DNA, RNA, protein-protein interactions, or protein-receptor interactions.

Exemplary therapeutic agents include, but are not limited to, small molecules such as drug compounds, peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

A "protein," "peptide," or "polypeptide" comprises a polymer of amino acid residues linked together by peptide bonds. The terms refer to proteins, polypeptides, and peptides of any size, structure, or function. Typically, a protein or peptide will be at least three amino acids long. A protein may refer to an individual protein or a collection of proteins. Proteins, peptides, and polypeptides can contain natural amino acids and/or non-natural amino acids (i.e., compounds that do not occur in nature can be incorporated into a polypeptide chain). A protein or polypeptide may be a single molecule or may be a multi-molecular complex. A protein or polypeptide may be a fragment of a naturally occurring protein or peptide. A protein may be naturally occurring, recombinant, synthetic, or any combination of these.

The term "nucleic acid" (also referred to as "polynucleotides" or "oligonucleotides") refers to a series of nucleotide bases (also called "nucleotides") in DNA and RNA, and refers to any chain of two or more nucleotides. A nucleotide sequence typically carries genetic information, including the information used by cellular machinery to make proteins and enzymes. These terms include double- or single-stranded genomic and cDNA, RNA, any synthetic and genetically manipulated polynucleotides, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids. Exemplary DNAs include single-stranded DNA (ssDNA), double-stranded DNA (dsDNA), plasmid DNA (pDNA), genomic DNA (gDNA), complementary DNA (cDNA), antisense DNA, chloroplast DNA (ctDNA or cpDNA), microsatellite DNA, mitochondrial DNA (mtDNA or mDNA), kinetoplast DNA (kDNA), provirus, lysogen, repetitive DNA, satellite DNA, and viral DNA. Exemplary RNAs include single-stranded RNA (ssRNA), double-stranded RNA (dsRNA), small interfering RNA (siRNA), messenger RNA (mRNA), precursor messenger RNA (pre-mRNA), small hairpin RNA or short hairpin RNA (shRNA), microRNA (miRNA), guide RNA (gRNA), transfer RNA (tRNA), antisense RNA (asRNA), heterogeneous nuclear RNA (hnRNA), coding RNA, non-coding RNA (ncRNA), long non-coding RNA (long ncRNA or lncRNA), satellite RNA, viral satellite RNA, signal recognition particle RNA, small cytoplasmic RNA, small nuclear RNA (snRNA), ribosomal RNA (rRNA), Piwi-interacting RNA (piRNA), polyinosinic acid, ribozyme, flexizyme, small nucleolar RNA (snoRNA), spliced leader RNA, viral RNA, and viral satellite RNA.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease.

The terms "composition" and "formulation" are used interchangeably.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

The term "ocular condition" refers to any disease or condition involving the eye of a subject. Examples of ocular conditions include, accommodative dysfunction, amblyopia, astigmatism, blepharitis, cataract, chalazion, color vision deficiency, computer vision syndrome, conjunctivitis, convergence insufficiency, corneal abrasion, crossed eyes, diabetic retinopathy, dry eye, farsightedness, floaters and spots, glaucoma, hordeolum, hyperopia, keratitis, keratoconus, lazy eye, macular degeneration (e.g., age-related macular degeneration (AMD)), migraine with aura, myopia, nearsightedness, nystagmus, ocular allergies, ocular hypertension, ocular migraine visual disturbance, pinquecula, presbyopia, pterygium, ptosis, retinal detachment, retinitis pigmentosa, ocular cancers (e.g., retinoblastoma), strabismus, sty, subconjunctival hemorrhage, and uveitis.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from preexisting vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., Stedman's Medical Dictionary, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperinsulinemia, insulin resistance, and obesity.

A "diabetic condition" refers to diabetes and pre-diabetes. Diabetes refers to a group of metabolic diseases in which a person has high blood sugar, either because the body does not produce enough insulin, or because cells do not respond to the insulin that is produced. This high blood sugar produces the classical symptoms of polyuria (frequent urination), polydipsia (increased thirst) and polyphagia (increased hunger). There are several types of diabetes. Type I diabetes results from the body's failure to produce insulin, and presently requires the person to inject insulin or wear an insulin pump. Type II diabetes results from insulin resistance a condition in which cells fail to use insulin properly, sometimes combined with an absolute insulin deficiency. Gestational diabetes occurs when pregnant women without a previous diagnosis of diabetes develop a high blood glucose level. Other forms of diabetes include congenital diabetes, which is due to genetic defects of insulin secretion, cystic fibrosis-related diabetes, steroid diabetes induced by high doses of glucocorticoids, and several forms of monogenic diabetes, e.g., mature onset diabetes of the young (e.g., MODY 1, 2, 3, 4, 5, 6, 7, 8, 9, or 10). Pre-diabetes indicates a condition that occurs when a person's blood glucose levels are higher than normal but not high enough for a diagnosis of diabetes. All forms of diabetes increase the risk of long-term complications. These typically develop after many years, but may be the first symptom in those who have otherwise not received a diagnosis before that time. The major long-term complications relate to damage to blood vessels. Diabetes doubles the risk of cardiovascular disease and macrovascular diseases such as ischemic heart disease (angina, myocardial infarction), stroke, and peripheral vascular disease. Diabetes also causes microvascular complications, e.g., damage to the small blood vessels. Diabetic retinopathy, which affects blood vessel formation in the retina of the eye, can lead to visual symptoms, reduced vision, and potentially blindness. Diabetic nephropathy, the impact of diabetes on the kidneys, can lead to scarring changes in the kidney tissue, loss of small or progressively larger amounts of protein in the urine, and eventually chronic kidney disease requiring dialysis. Diabetic neuropathy is the impact of diabetes on the nervous system, most commonly causing numbness, tingling and pain in the feet and also increasing the risk of skin damage due to altered sensation. Together with vascular disease in the legs, neuropathy contributes to the risk of diabetes-related foot problems, e.g., diabetic foot ulcers, that can be difficult to treat and occasionally require amputation.

Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as particle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

BRIEF DESCRIPTION OF THE DRAWINGS

The accompanying drawings, which constitute a part of this specification, illustrate several embodiments of the invention and together with the description, serve to explain the principles of the invention.

FIG. 16A shows sustained release of three small molecule drugs using ABC bottlebrush copolymers. In particular, in vitro release of drug payload from ABC micellular network at 37° C. in PBS. The drug-loaded gel (300 µL) was incubated in 2 mL PBS solution at 37° C. The gel stays at the bottom of the vial and drug slowly diffuses out into PBS. Aliquots (100 µL) were collected every 24 h for LC-MS measurement for quantification of drug release rate. The collected volume was replaced with fresh buffer. FIG. 16B shows relative tumor volume over the sustained release period. Balb/c nude mice were inoculated subcutaneously with injection of A549 cells (10 million cells in 100 µL of PBS). Tumors were allowed to grow for 7 weeks before treatment. Mice bearing the tumors with similar volumes (~250 mm$^3$) were randomly selected for each cohort (n=4). Subsequently, the drug solution in DMSO or the ABC (at 4° C.) in PBS was intratumor injected to the tumors. Tumor size was measured every two or three days by a digital Vernier caliper across its longest (a) and shortest diameters (b), and its volume (V) was calculated according to the following formula: V=0.5×a×b$^2$.

FIG. 17A. Experimental procedure: In a nitrogen filled glovebox, to a 4-mL vial charged with a stir bar and Nb-PLA (Nor-PLA) macro-monomer (MM) (69.5 mg, 0.01 mmol) was added anhydrous THF (CAS 109-99-9) (230 µL). To this mixture then was added Grubbs III catalyst solution in THF, all at once (50.5 µL, 1 µmol) to give MM:Grubbs III ratio of 10:1. The polymerization reaction mixture was stirred at room temperature for 30 min and then a 5-µL aliquot was taken for size exclusion chromatography (SEC) analysis. A fresh 0.05-M solution of second MM, Nb-PEG (Nor-PEG), (184.1 mg, 0.04 mmol) in THF was prepared inside glovebox and added to reaction mixture all at once. The polymerization reaction was stirred at room temperature for another 3 h, after which 5-µL aliquot was taken and solution of third MM, Nb-PNIPAM (Nor-PNIPAM), (80.2 mg, 0.01 mmol). After stirring for another 8 h, 5-µL aliquot was taken and then ethyl vinyl ether (50 µL) was added to quench the reaction. The reaction mixture was diluted with 2 mL of DMSO (CAS 67-68-5) and transferred into a 20-mL scintillation vial. The forming mixture was rapidly stirred and diluted to 20 mL by dropwise addition of milli-Q water. The forming aqueous mixture was then transferred into a spin filter with MWCO 100 kDa and concentrated to 2 mL (3000 RPM), rediluted to 10 mL and concentrated again to ensure removal of DMSO and any unreacted MM. The centrifugation was stopped at 20-min intervals to homogenize centration gradient. The product was obtained by lyophilization. FIGS. 17B-17C. Dried samples of copolymers were analyzed by SEC (FIG. 17B) and $^1$H NMR (FIG. 17C) to estimate content of individual blocks and molecular weight of final copolymer.

FIG. 18 shows that properties of bottlebrush copolymers can be tuned via assembly using sequential ROMP. $^a$: $^1$H NMR estimation; $^b$: Dynamic Light Scattering (DLS).

DETAILED DESCRIPTION OF CERTAIN EMBODIMENTS

Provided herein are triblock bottlebrush copolymers; and particles, hydrogels, and formulations thereof. The particles, hydrogels, and formulations of the present invention may comprise one or more therapeutic agents, and may be administered to a subject for extended release of the one or more therapeutic agents. For example, in certain embodiments, the triblock bottlebrush copolymers, particles, and hydrogels described herein are thermally-responsive and gel at physiological temperature (e.g., upon administration to a subject), providing injectable and/or implantable gels for controlled release drug delivery. Therefore, the present invention also provides methods of using the triblock bottlebrush copolymers, particles, hydrogels, and formulations described herein (e.g., in biomedical applications such as the treatment of diseases or conditions). The present invention also provides methods of preparing triblock bottlebrush copolymers, particles, and hydrogels described herein. In yet another aspect, the present invention provides kits comprising the triblock bottlebrush copolymers, particles, hydrogels, and formulations described herein.

Triblock Bottlebrush Copolymers

Figure 1A:
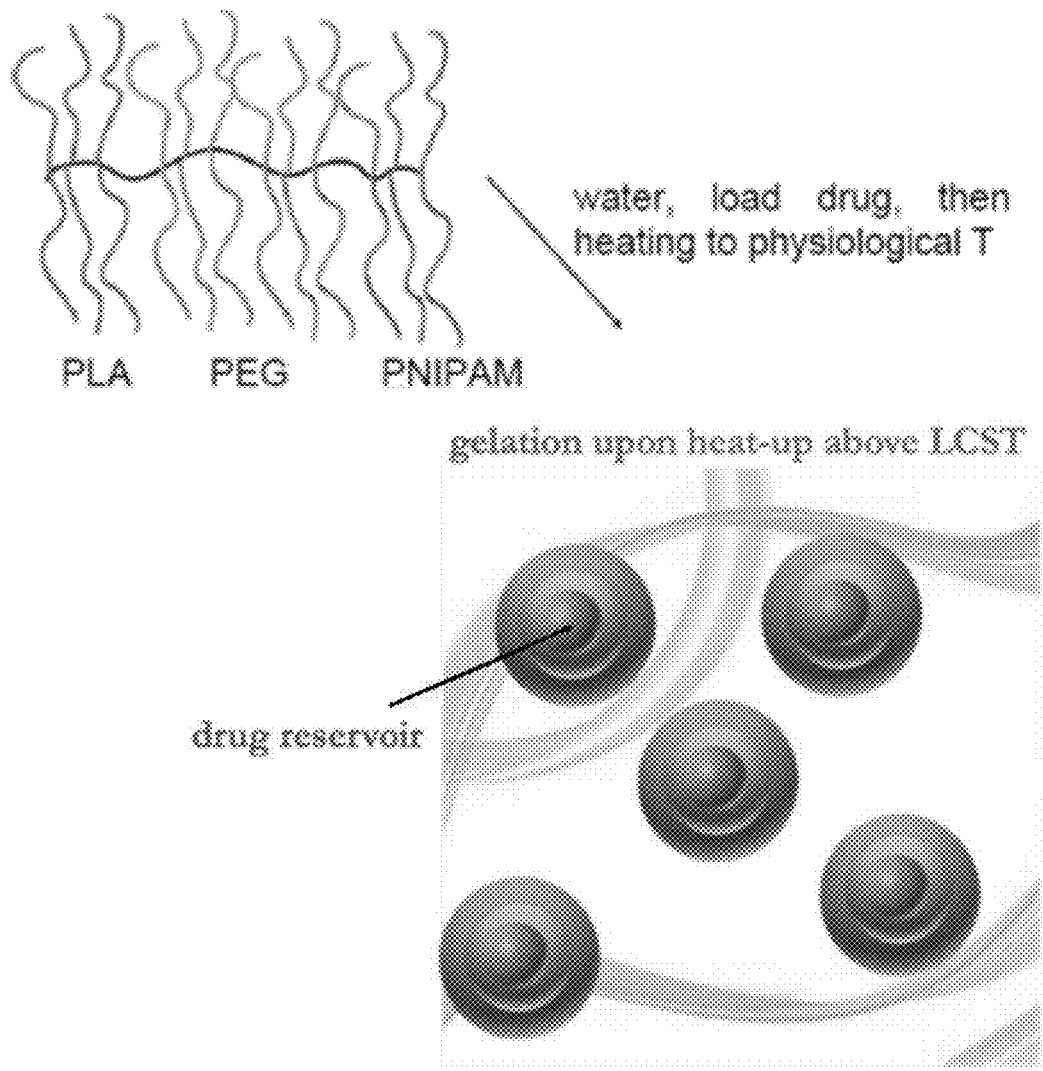
FIG. 1A shows an exemplary schematic illustration of a triblock bottlebrush hydrogel drug reservoir.
Figure 1B:
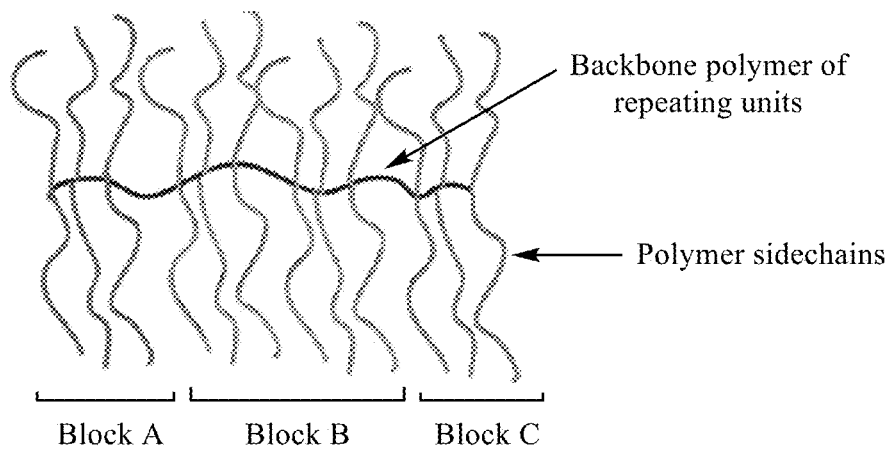
FIG. 1B shows an outline of the general architecture of the triblock bottlebrush copolymers provided herein.
Figure 1C:
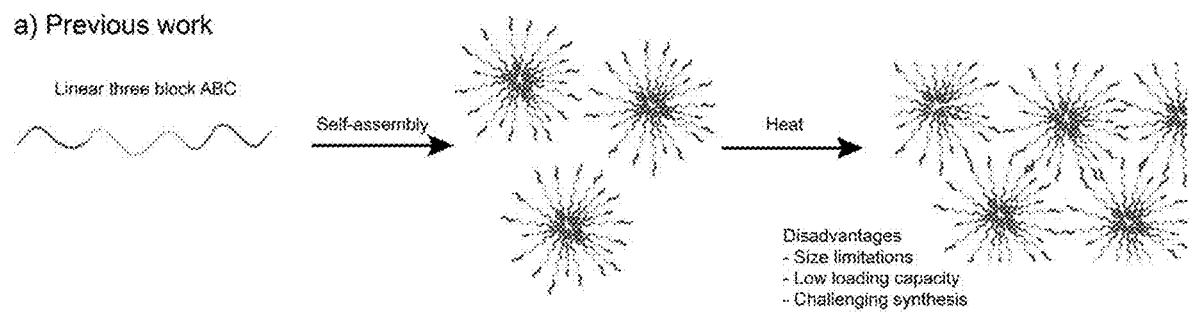
FIG. 1C shows a comparison of linear three-block ABC polymers (existing systems) with bottlebrush three-block ABC polymers (this invention). Also shown are the polymers' self-assemblies into particles and hydrogels.
Figure 1C:
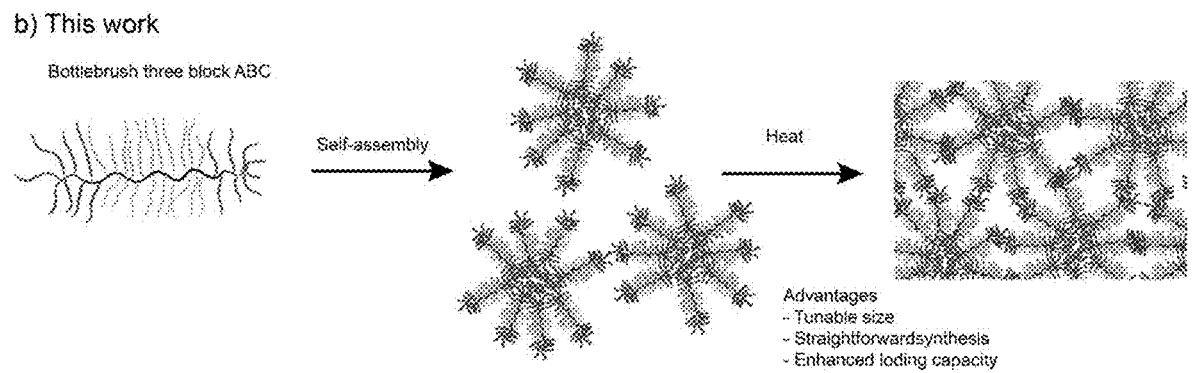

One aspect of the present invention relates to triblock bottlebrush copolymers. In certain embodiments, the polymer is an ABC triblock bottlebrush copolymer comprising a Block A polymer, a Block B polymer, and a Block C polymer. A triblock bottlebrush copolymer of the present invention comprises a backbone polymer of repeating units covalently linked to polymeric sidechains; wherein Block A, Block B, and Block C of the copolymer comprise polymeric sidechains covalently linked to the repeating units of the backbone polymer; and wherein at least one of Block A, Block B, and Block C comprises polymeric sidechains that exhibit lower critical solution temperature (LCST) behavior. As described herein, each polymeric side chain of Block A is of the same polymer type, each polymeric side chain of Block B is of the same polymer type, and each polymeric side chain of Block C is of the same polymer type. Also, as described herein, Block A, Block B, and Block C comprise polymeric side chains which are of different polymer types. As a representative example, an outline of the general architecture of a triblock bottlebrush copolymer provided herein is shown in FIGS. 1B-1C.

A triblock bottlebrush copolymer comprising polymeric sidechains that exhibit LCST behavior may be thermally-responsive and capable of undergoing a phase transition at a particular temperature. Such a polymer would be useful, for example, as a thermally-responsive drug delivery vehicle. As defined herein, "lower critical solution temperature" (LCST) is the temperature below which a polymer is miscible in a solvent. "LCST behavior" refers to a characteristic of a polymer wherein the polymer exhibits a lower critical solution temperature. For example, a polymer that exhibits LCST behavior is a polymer which is miscible in a solvent at or below a certain temperature (i.e., the polymer's LCST), and which may solidify or congeal (e.g., to form a solid or a gel) in solution at or above the certain temperature. A common polymer known to exhibit LCST behavior is poly(N-isopropylacrylamide) (PNIPAM), which has a lower critical solution temperature of around 32° C. PNIPAM is a useful in biomedical applications (e.g., in drug delivery) since it has a LCST close to physiological temperature (37° C.). Other polymers that exhibit LCST behavior include, but are not limited to, poly(N,N-diethylacrylamide) (PDEAAm) (LCST from 25 to 32° C.), poly(N-vinylcaprolactam) (PVCL) (LCST between 25 and 35° C.), poly[2-(dimethylamino)ethyl methacrylate] (PDMAEMA) (LCST around 50° C.), and polyethylene glycol) (PEG) (LCST of about 85° C.).

In certain embodiments, the LCST of the triblock bottlebrush copolymers provided herein is around physiological temperature (approximately 37° C.). In certain embodiments, the LCST of the triblock bottlebrush copolymers provided herein is around 33° C. In certain embodiments, the LCST of the triblock bottlebrush copolymers provided herein is between 30 and 40° C., inclusive.

The triblock bottlebrush copolymers provided herein are ABC triblock bottlebrush copolymers, meaning that the polymeric sidechains of Blocks A, B, and C are different polymers. For example, no two of Blocks A, B, and C have the same polymer sidechains. "Different polymer," as used herein, refers to different polymer composition (i.e., composed of different monomer subunits). In other words, the polymeric sidechains of Blocks A, B, and C each are of a different polymer class, or of a different polymer type. For instance, when each polymeric sidechain of Block A is independently a PLA polymer and each polymeric side chain of Block B is independently a polyethylene glycol (PEG) polymer, the sidechains of A and B are considered to be different polymer types, of different polymer classes, and different polymers.

It is also to be understood that each polymeric sidechain of Block A are the same polymer, each polymeric sidechain of Block B are the same polymer, and each polymeric sidechain of Block C are the same polymer (i.e., composed of the same monomer subunits, i.e., of the same polymer type/class). However, any two polymeric sidechains of Block A, of Block B, or of Block C may be of the same or different length, or of the same or different molecular weight. "Same polymer," as used here, refers to the same polymer composition (i.e., composed of the same monomers), and does not necessarily mean polymers of the same length, molecular weight, or structure. Polymers that are the "same polymer" can have different polymer lengths, molecular weight, terminal groups, etc. For instance, all of A are considered the "same polymer" if all of A are polylactic acid (PLA) side chains, even if each A is a PLA side chain has a different length and molecular weight.

The triblock bottlebrush copolymers provided herein comprise a backbone polymer of repeating units ("backbone units"). The repeating backbone units of any two of Blocks A, B, and C may be same or different. Further, any two of Blocks A, B, and C may comprise the same or a different number of repeating backbone units. In certain embodiments, each of Blocks A, B, and C independently comprise 1 to 4000 repeating backbone units, inclusive. In certain embodiments, each of Blocks A, B, and C independently comprise 2 to 4000 repeating backbone units, inclusive. In certain embodiments, each of Blocks A, B, and C independently comprise 2 to 2000 repeating backbone units, inclusive. In certain embodiments, each of Blocks A, B, and C independently comprise 2 to 1000 repeating backbone units, inclusive. In certain embodiments, each of Blocks A, B, and C independently comprise 2 to 500 repeating backbone units, inclusive. In certain embodiments, each of Blocks A, B, and C independently comprise 2 to 200 repeating backbone units, inclusive. In certain embodiments, each of Blocks A, B, and C independently comprise 2 to 100 repeating backbone units, inclusive. In certain embodiments, each of Blocks A, B, and C independently comprise 5 to 100 repeating backbone units, inclusive. In certain embodiments, each of Blocks A, B, and C independently comprise 5 to 50 repeating backbone units, inclusive. In certain embodiments, each repeating backbone unit of the triblock bottlebrush copolymer is covalently linked to a polymeric sidechain. In certain embodiments, some but not all repeating backbone units are covalently linked to polymeric sidechains.

The polymeric sidechains of Block A, Block B, and Block C of the triblock bottlebrush copolymer may comprise any polymer. Examples of classes of polymers include, but are not limited to, polyvinyl polymers (e.g., polyvinyl chloride), polyethylenes (e.g., polyethylene, polytetrafluoroethylene), polypropylenes, polyacetylenes, polyethers (e.g., polyethylene glycol, polyoxymethylene, polypropylene glycol, polytetramethylene glycol, poly(ethyl ethylene) phosphate, poly (oxazoline)), polyamines, polyesters (e.g., polyglycolic acid, polylactic acid, poly(lactic-co-glycolic acid), polycaprolactone, polyhydroxyalkanoate, polyhydroxybutyrate, polyethylene adipate, polybutylene succinate, poly(3-hydroxybutyrate-co-3-hydroxyvalerate), polysilanes, polysiloxanes (e.g., polydimethylsiloxane), polyacrylates (e.g., polymethacrylate, poly(n-butyl acrylate), poly(tert-butyl acrylate)), polystyrenes, polylactides (e.g., polylactic acid), polyamino acids, polypeptides, polyamides, polyacrylamides (e.g., polymethylacrylamide), and polysaccharides. The polymeric sidechains may be homopolymers or copolymers. The polymeric sidechains may be linear or branched. In certain embodiments, the polymeric sidechains are linear.

In certain embodiments, one or more of Block A, Block B, and Block C of the triblock bottlebrush copolymer comprise polyester sidechains. In certain embodiments, Block A of the triblock bottlebrush copolymer comprises polyester sidechains. In certain embodiments, Block B of the triblock bottlebrush copolymer comprises polyester sidechains. In certain embodiments, Block C of the triblock bottlebrush copolymer comprises polyester sidechains. Examples of polyesters include, but are not limited to, polyglycolic acid (PGA), polylactic acid (PLA), poly(lactic-co-glycolic acid) (PLGA), polycaprolactone (PCL), polyhydroxyalkanoate (PHA), polyhydroxybutyrate (PHB), polyethylene adipate (PEA), polybutylene succinate (PBS), or poly(3-hydroxybutyrate-co-3-hydroxyvalerate) (PHBV). In certain embodiments, the triblock bottlebrush copolymer comprises polylactic acid (PLA) sidechains. In certain embodiments, the triblock bottlebrush copolymer comprises polyglycolic acid (PGA) or poly(lactic-co-glycolic acid) (PLGA) sidechains. In certain embodiments, Block A of the triblock bottlebrush copolymer comprises a polylactic acid (PLA), polyglycolic acid (PGA), or poly(lactic-co-glycolic acid) (PLGA) sidechain. In certain embodiments, Block A of the triblock bottlebrush copolymer comprises PLA sidechains. In certain embodiments, Block B of the triblock bottlebrush copolymer comprises PLA sidechains. In certain embodiments, Block C of the triblock bottlebrush copolymer comprises PLA sidechains.

In certain embodiments, one or more of Block A, Block B, and Block C of the triblock bottlebrush copolymer comprise polyether sidechains. In certain embodiments, Block B of the triblock bottlebrush copolymer comprises polyether sidechains. In certain embodiments, Block A of the triblock bottlebrush copolymer comprises polyether sidechains. In certain embodiments, Block C of the triblock bottlebrush copolymer comprises polyether sidechains. Examples of polyethers include, but are not limited to, polyethylene glycol (PEG), polyoxymethylene (POM), polypropylene glycol (PPG), polytetramethylene glycol (PTMG), poly(ethyl ethylene) phosphate (PEEP), and poly (oxazoline). In certain embodiments, the triblock bottlebrush copolymer comprises polyethylene glycol (PEG) sidechains. In certain embodiments, Block B of the triblock bottlebrush copolymer comprises PEG sidechains.

As generally described herein, at least one of Block A, Block B, and Block C of the triblock bottlebrush copolymer comprises polymeric sidechains that exhibit LCST behavior. In certain embodiments, Block C comprises polymeric sidechains composed of a polymer that exhibits LCST behavior. In certain embodiments, Block A comprises polymeric sidechains composed of a polymer that exhibits LCST behavior. In certain embodiments, Block B comprises polymeric sidechains composed of a polymer that exhibits LCST behavior. In certain embodiments, the triblock bottlebrush copolymer comprises polyacrylamide sidechains. In certain embodiments, the triblock bottlebrush copolymer comprises poly(N-alkylacrylamide) sidechains. In certain embodiments, the triblock bottlebrush copolymer comprises poly (N-isopropylacrylamide) (PNIPAM) sidechains. In certain embodiments, Block C comprises poly(N-alkylacrylamide) sidechains. In certain embodiments, Block C comprises PNIPAM sidechains. In certain embodiments, Block A comprises PNIPAM sidechains. In certain embodiments, Block B comprises PNIPAM sidechains.

In certain embodiments, Block A comprises polyester sidechains, Block B comprises polyether sidechains, and Block C comprises polyacrylamide sidechains. For example, in a particular embodiment, Block A comprises PLA sidechains, Block B comprises PEG sidechains, and Block C comprises PNIPAM sidechains. In certain embodiments, Block A comprises polyacrylamide sidechains, Block B comprises polyester sidechains, and Block C comprises polyether sidechain. For instance, in another particular embodiment, Block A comprises PNIPAM sidechain, Block B comprises PLA sidechains, and Block C comprises PEG sidechains.

The polymeric sidechains of Blocks A, B, and C may be of any molecular weight. In certain embodiments, the polymeric sidechains of Blocks A, B, and C each independently have a molecular weight ranging from approximately 50 to approximately 10000 Da, approximately 100 to approximately 10000 Da, approximately 500 to approximately 10000 Da, approximately 1000 to approximately 10000 Da, or approximately 2000 to approximately 10000 Da; each range being inclusive. In certain embodiments, the polymeric sidechains of Blocks A, B, and C each independently have molecular weight greater than 10000 Da.

In certain embodiments, a triblock bottlebrush copolymer of the present invention is of Formula (I):

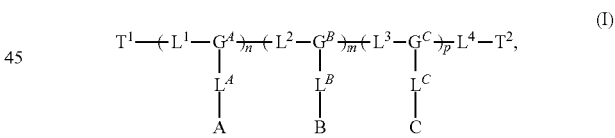

wherein:

each of $G^A$, $G^B$, and $G^C$ is independently optionally substituted alkylene, optionally substituted heteroalkylene, optionally substituted carbocyclylene, optionally substituted heterocyclylene, optionally substituted arylene, optionally substituted heteroarylene, or a combination thereof, and combination thereof;

each of $L^1$, $L^2$, $L^3$, and $L^4$ is independently a linker selected from the group consisting of optionally substituted alkylene, optionally substituted heteroalkylene, optionally substituted alkenylene, optionally substituted alkynylene, and combinations thereof;

each of $L^A$, $L^B$, and $L^C$ is independently a linker selected from the group consisting of optionally substituted alkylene, optionally substituted heteroalkylene, optionally substituted carbocyclylene, optionally substituted heterocyclylene, optionally substituted arylene, optionally substituted heteroarylene, and combinations thereof;

each of $T^1$ and $T^2$ is independently a terminal group selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thiol;

each of A, B, and C is independently a polymer, wherein all of A are the same polymer, all of B are the same polymer, and all of C are the same polymer;

provided that A, B, and C are different polymers; and each of n, m, and p is independently an integer between 1 and 4000, inclusive.

In certain embodiments, each of A, B, and C is independently a polymer, wherein all of A are the same polymer, all of B are the same polymer, and all of C are the same polymer; provided that A, B, and C are different polymers; and provided that at least one of A, B, or C is a polymer that exhibits LCST behavior. In certain embodiments, A, B, and C are independently selected from the group consisting of polyesters, polyethers, and polyacrylamides; provided that A, B, and C are different polymers. The polyester group may be any polyester described herein. Likewise, the polyether group may be any polyether described herein. Additionally, the polyacrylamide group may be any polyacrylamide described herein.

As described herein, the triblock bottlebrush copolymers provided herein are ABC triblock bottlebrush copolymers, meaning that groups A, B, and C are different polymers. "Different polymer," as used herein, refers to different polymer composition (i.e., composed of different monomer subunits). In other words, A, B, and C each are of a different polymer class, or of a different polymer type. For instance, when each of A is independently a PLA polymer and each of B is independently a polyethylene glycol (PEG) polymer, A and B are considered to be different polymer types, of different polymer classes, and therefore different polymers. However, as also described herein, each of A are the same polymer, each of B are the same polymer, and each of C are the same polymer (i.e., composed of the same monomer subunits, i.e., of the same polymer type/class). "Same polymer," as used here, refers to the same polymer composition (i.e., composed of the same monomers). Any two of A, any two of B, or any two of C may be of the same or different length, or of the same or different molecular weight. Polymers that are the "same polymer" can have different polymer lengths, molecular weight, terminal groups, etc. For instance, all of A are considered the "same polymer" if all of A are polylactic acid (PLA) side chains, even if each A is a PLA side chain has a different length and molecular weight.

As generally defined herein, group A is a polymer. As described herein, each A is the same polymer (i.e., of the same polymeric composition, i.e., composed of the same monomers). In certain embodiments, group A is a polymer that exhibits LCST behavior. In certain embodiments, group A is a polymer group selected from the group consisting of polyesters, polyethers, and polyacrylamides. In certain embodiments, group A is a polyester. In certain embodiments, group A is a polyether. In certain embodiments, group A is a polyacrylamide. In certain embodiments, group A is a polyester selected from the group consisting of polyglycolic acid (PGA), polylactic acid (PLA), poly(lactic-co-glycolic acid) (PLGA), polycaprolactone (PCL), polyhydroxyalkanoate (PHA), polyhydroxybutyrate (PHB), polyethylene adipate (PEA), polybutylene succinate (PBS), and poly(3-hydroxybutyrate-co-3-hydroxyvalerate) (PHBV). In certain embodiments, group A is polylactic acid (PLA). In certain embodiments, group A is polyglycolic acid (PGA) or poly(lactic-co-glycolic acid) (PLGA). In certain embodiments, group A is a polyether. In certain embodiments, group A is polyether selected from the group consisting of polyethylene glycol (PEG), polyoxymethylene (POM), polypropylene glycol (PPG), polytetramethylene glycol (PTMG), poly(ethyl ethylene) phosphate (PEEP), and poly(oxazoline). In certain embodiments, group A is polyethylene glycol (PEG). In certain embodiments, group A is a polyacrylamide. In certain embodiments, group A is a poly(N-alkylacrylamide). In certain embodiments, group A is poly(N-isopropylacrylamide).

As generally defined herein, group B is a polymer. As described herein, each B is the same polymer (i.e., of the same polymeric composition, i.e., composed of the same monomers). In certain embodiments, group B is a polymer that exhibits LCST behavior. In certain embodiments, group B is a polymer group selected from the group consisting of polyesters, polyethers, and polyacrylamides. In certain embodiments, group B is a polyester. In certain embodiments, group B is a polyether. In certain embodiments, group B is a polyacrylamide. In certain embodiments, group B is polyether selected from the group consisting of polyethylene glycol (PEG), polyoxymethylene (POM), polypropylene glycol (PPG), polytetramethylene glycol (PTMG), poly(ethyl ethylene) phosphate (PEEP), and poly(oxazoline). In certain embodiments, group B is polyethylene glycol (PEG). In certain embodiments, group B is a polyester. In certain embodiments, group B is a polyester selected from the group consisting of polyglycolic acid (PGA), polylactic acid (PLA), poly(lactic-co-glycolic acid) (PLGA), polycaprolactone (PCL), polyhydroxyalkanoate (PHA), polyhydroxybutyrate (PHB), polyethylene adipate (PEA), polybutylene succinate (PBS), and poly(3-hydroxybutyrate-co-3-hydroxyvalerate) (PHBV). In certain embodiments, group B is polylactic acid (PLA). In certain embodiments, group B is polyglycolic acid (PGA) or poly(lactic-co-glycolic acid) (PLGA). In certain embodiments, group B is a polyacrylamide. In certain embodiments, group B is a poly(N-alkylacrylamide). In certain embodiments, group B is poly(N-isopropylacrylamide).

As generally defined herein, group C is a polymer. As described herein, each B is the same polymer (i.e., of the same polymeric composition, i.e., composed of the same monomers). In certain embodiments, group C is a polymer that exhibits LCST behavior. In certain embodiments, group C is a polymer group selected from the group consisting of polyesters, polyethers, and polyacrylamides. In certain embodiments, group C is a polyacrylamide. In certain embodiments, group C is a poly(N-alkylacrylamide). In certain embodiments, group C is poly(N-isopropylacrylamide). In certain embodiments, group C is a polyether. In certain embodiments, group C is polyether selected from the group consisting of polyethylene glycol (PEG), polyoxymethylene (POM), polypropylene glycol (PPG), polytetramethylene glycol (PTMG), poly(ethyl ethylene) phosphate (PEEP), and poly(oxazoline). In certain embodiments, group C is polyethylene glycol (PEG). In certain embodiments, group C is a polyester. In certain embodiments, group C is a polyester selected from the group consisting of polyglycolic acid (PGA), polylactic acid (PLA), poly(lactic-co-glycolic acid) (PLGA), polycaprolactone (PCL), polyhydroxyalkanoate (PHA), polyhydroxybutyrate (PHB), polyethylene adipate (PEA), polybutylene succinate (PBS), and poly(3-hydroxybutyrate-co-3-hydroxyvalerate) (PHBV). In certain embodiments, group C is polylactic acid (PLA). In certain embodiments, group C is polyglycolic acid (PGA) or poly(lactic-co-glycolic acid) (PLGA).

In certain embodiments, each of A, each of B, or each of C is a polyester group of the following formula:

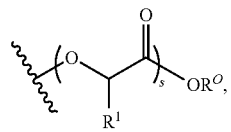

wherein:

$R^1$ is hydrogen, optionally substituted alkyl, optionally substituted alkenyl, optionally substituted alkynyl, optionally substituted aryl, optionally substituted heteroaryl, optionally substituted carbocyclyl, optionally substituted heterocyclyl, or optionally substituted acyl;

$R^O$ is hydrogen, optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted acyl, or an oxygen protecting group; and s is an integer between 5 and 2000, inclusive.

As generally defined herein, $R^1$ is hydrogen, optionally substituted alkyl, optionally substituted alkenyl, optionally substituted alkynyl, optionally substituted aryl, optionally substituted heteroaryl, optionally substituted carbocyclyl, optionally substituted heterocyclyl, or optionally substituted acyl. In certain embodiments, $R^1$ is hydrogen. In certain embodiments, $R^1$ is optionally substituted alkyl. In certain embodiments, $R^1$ is optionally substituted alkenyl. In certain embodiments, $R^1$ is optionally substituted alkynyl. In certain embodiments, $R^1$ is optionally substituted aryl. In certain embodiments, $R^1$ is optionally substituted heteroaryl In certain embodiments, $R^1$ is optionally substituted carbocyclyl. In certain embodiments, $R^1$ is optionally substituted heterocyclyl. In certain embodiments, $R^1$ is optionally substituted acyl. In certain embodiments, $R^1$ is optionally substituted $C_{1-6}$ alkyl. In certain embodiments, $R^1$ is unsubstituted $C_{1-6}$ alkyl. In certain embodiments, $R^1$ is optionally substituted $C_{1-3}$ alkyl. In certain embodiments, $R^1$ is unsubstituted $C_{1-3}$ alkyl. In certain embodiments, $R^1$ is selected from the group consisting of methyl, ethyl, n-propyl, iso-propyl, n-butyl, sec-butyl, iso-butyl, and tert-butyl. In certain embodiments, $R^1$ is methyl.

In certain embodiments, each of A, each of B, or each of C is a polyester group of the following formula:

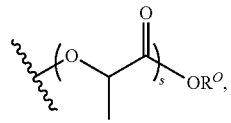

wherein:

$R^O$ is hydrogen, optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted acyl, or an oxygen protecting group; and s is an integer between 5 and 2000, inclusive.

As generally defined herein, $R^O$ hydrogen, optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted acyl, or an oxygen protecting group. In certain embodiments, $R^O$ is hydrogen. In certain embodiments, $R^O$ is optionally substituted alkyl. In certain embodiments, $R^O$ is optionally substituted $C_{1-6}$ alkyl. In certain embodiments, $R^O$ is unsubstituted $C_{1-6}$ alkyl. In certain embodiments, $R^O$ is selected from the group consisting of methyl, ethyl, n-propyl, iso-propyl, n-butyl, sec-butyl, iso-butyl, and tert-butyl. In certain embodiments, $R^O$ is optionally substituted alkenyl. In certain embodiments, $R^O$ is optionally substituted alkynyl. In certain embodiments, $R^O$ is optionally substituted aryl. In certain embodiments, $R^O$ is optionally substituted heteroaryl. In certain embodiments, $R^O$ is optionally substituted carbocyclyl. In certain embodiments, $R^O$ is optionally substituted heterocyclyl. In certain embodiments, $R^O$ is optionally substituted acyl. In certain embodiments, $R^O$ is an oxygen protecting group.

As generally defined herein, s is an integer between 5 and 2000, inclusive. In certain embodiments, s is an integer between 5 and 1000, inclusive. In certain embodiments, s is an integer between 5 and 1000, inclusive. In certain embodiments, s is an integer between 5 and 500, inclusive. In certain embodiments, s is an integer between 5 and 200, inclusive. In certain embodiments, s is an integer between 5 and 100, inclusive. In certain embodiments, s is an integer between 50 and 2000, inclusive. In certain embodiments, s is an integer between 100 and 2000, inclusive. In certain embodiments, s is an integer between 200 and 2000, inclusive. In certain embodiments, s is an integer between 500 and 2000, inclusive. In certain embodiments, s is an integer between 1000 and 2000, inclusive.

In certain embodiments, each of A, each of B, or each of C is a polyether group of the following formula:

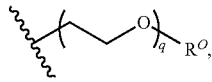

wherein:

$R^O$ is hydrogen, optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted acyl, or an oxygen protecting group; and q is an integer between 5 and 2000, inclusive.

As generally defined herein, q is an integer between 5 and 2000, inclusive. In certain embodiments, q is an integer between 5 and 1000, inclusive. In certain embodiments, q is an integer between 5 and 1000, inclusive. In certain embodiments, q is an integer between 5 and 500, inclusive. In certain embodiments, q is an integer between 5 and 200, inclusive. In certain embodiments, q is an integer between 5 and 100, inclusive. In certain embodiments, q is an integer between 50 and 2000, inclusive. In certain embodiments, q is an integer between 100 and 2000, inclusive. In certain embodiments, q is an integer between 200 and 2000, inclusive. In certain embodiments, q is an integer between 500 and 2000, inclusive. In certain embodiments, q is an integer between 1000 and 2000, inclusive.

In certain embodiments, each of A, each of B, or each of C is a polyacrylamide group of the following formula:

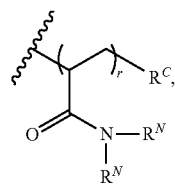

wherein:

each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^N$ on the same nitrogen atom are taken together with the intervening atoms to form optionally substituted heterocyclyl or optionally substituted heteroaryl;

$R^C$ is hydrogen, halogen, —CN, optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted acyl, optionally substituted amino, optionally substituted hydroxyl, or optionally substituted thiol; and r is an integer between 5 and 2000, inclusive.

As generally defined herein, each instance of $R^N$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two $R^N$ on the same nitrogen atom are taken together with the intervening atoms to form optionally substituted heterocyclyl or optionally substituted heteroaryl. In certain embodiments, $R^N$ is hydrogen. In certain embodiments, $R^N$ is optionally substituted alkyl. In certain embodiments, $R^N$ is optionally substituted alkenyl. In certain embodiments, $R^N$ is optionally substituted alkynyl. In certain embodiments, $R^N$ is optionally substituted carbocyclyl. In certain embodiments, $R^N$ is optionally substituted heterocyclyl. In certain embodiments, $R^N$ is optionally substituted aryl. In certain embodiments, $R^N$ is optionally substituted heteroaryl. In certain embodiments, $R^N$ is or a nitrogen protecting group. In certain embodiments, $R^N$ on the same nitrogen atom are taken together with the intervening atoms to form optionally substituted heterocyclyl or optionally substituted heteroaryl. In certain embodiments, $R^N$ is optionally substituted $C_{1-6}$ alkyl. In certain embodiments, $R^N$ is unsubstituted $C_{1-6}$ alkyl. In certain embodiments, $R^N$ is optionally substituted $C_{1-3}$ alkyl. In certain embodiments, $R^N$ is unsubstituted $C_{1-3}$ alkyl. In certain embodiments, $R^N$ is selected from the group consisting of methyl, ethyl, n-propyl, iso-propyl, n-butyl, sec-butyl, iso-butyl, and tert-butyl. In certain embodiments, $R^N$ is iso-propyl.

In certain embodiments, each of A, each of B, or each of C is a polyacrylamide group of the following formula:

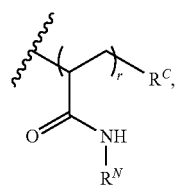

Wherein $R^C$, $R^N$, and r are as defined herein.

In certain embodiments, each of A, each of B, or each of C is a polyacrylamide group of the following formula:

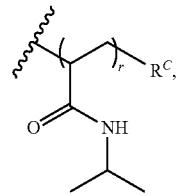

wherein:

$R^C$ is hydrogen, halogen, —CN, optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted acyl, optionally substituted amino, optionally substituted hydroxyl, or optionally substituted thiol; and r is an integer between 5 and 2000, inclusive.

As generally defined herein, $R^C$ is hydrogen, halogen, —CN, optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted acyl, optionally substituted amino, optionally substituted hydroxyl, or optionally substituted thiol. In certain embodiments, $R^C$ is hydrogen. In certain embodiments, $R^C$ is halogen. In certain embodiments, $R^C$ is —CN. In certain embodiments, $R^C$ is optionally substituted alkyl. In certain embodiments, $R^C$ is optionally substituted alkenyl. In certain embodiments, $R^C$ is optionally substituted alkynyl. In certain embodiments, $R^C$ is optionally substituted aryl. In certain embodiments, $R^C$ is optionally substituted heteroaryl. In certain embodiments, $R^C$ is optionally substituted carbocyclyl. In certain embodiments, $R^C$ is optionally substituted heterocyclyl. In certain embodiments, $R^C$ is optionally substituted acyl. In certain embodiments, $R^C$ is optionally substituted amino. In certain embodiments, $R^C$ is optionally substituted hydroxyl. In certain embodiments, $R^C$ is optionally substituted thiol. In certain embodiments, $R^C$ is optionally substituted $C_{1-6}$ alkyl. In certain embodiments, $R^C$ is substituted $C_{1-6}$ alkyl. In certain embodiments, $R^C$ is optionally substituted $C_{1-3}$ alkyl. In certain embodiments, $R^C$ is substituted $C_{1-3}$ alkyl. In certain embodiments, $R^C$ is of the formula:

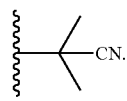

As generally defined herein, r is an integer between 5 and 2000, inclusive. In certain embodiments, r is an integer between 5 and 1000, inclusive. In certain embodiments, r is an integer between 5 and 1000, inclusive. In certain embodiments, r is an integer between 5 and 500, inclusive. In certain embodiments, r is an integer between 5 and 200, inclusive. In certain embodiments, r is an integer between 5 and 100, inclusive. In certain embodiments, r is an integer between 50 and 2000, inclusive. In certain embodiments, r is an integer between 100 and 2000, inclusive. In certain embodiments, r is an integer between 200 and 2000, inclusive. In certain embodiments, r is an integer between 500 and 2000, inclusive. In certain embodiments, r is an integer between 1000 and 2000, inclusive.

As generally defined herein, each of $L^1$, $L^2$, $L^3$, and $L^4$ is independently a linker selected from the group consisting of optionally substituted alkylene, optionally substituted heteroalkylene, optionally substituted alkenylene, optionally substituted alkynylene, and combinations thereof. In certain embodiments, each of $L^1$, $L^2$, $L^3$, and $L^4$ is optionally substituted alkylene. In certain embodiments, each of $L^1$, $L^2$, $L^3$, and $L^4$ is optionally substituted heteroalkylene. In certain embodiments, each of $L^1$, $L^2$, $L^3$, and $L^4$ is optionally substituted alkynylene. In certain embodiments, each of $L^1$, $L^2$, $L^3$, and $L^4$ is optionally substituted alkenylene. In certain embodiments, each of $L^1$, $L^2$, $L^3$, and $L^4$ is substituted alkenylene. In certain embodiments, each of $L^1$, $L^2$, $L^3$, and $L^4$ is unsubstituted alkenylene. In certain embodiments, each of $L^1$, $L^2$, $L^3$, and $L^4$ is of the formula:

In certain embodiments, each of $L^1$, $L^2$, $L^3$, and $L^4$ is of the formula:

In certain embodiments, each of $L^1$, $L^2$, $L^3$, and $L^4$ is of the formula:

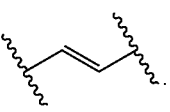

In certain embodiments, $L^1$ is optionally substituted alkylene. In certain embodiments, $L^1$ is optionally substituted heteroalkylene. In certain embodiments, $L^1$ is optionally substituted alkynylene. In certain embodiments, $L^1$ is optionally substituted alkenylene. In certain embodiments, $L^1$ substituted alkenylene. In certain embodiments, $L^1$ is unsubstituted alkenylene. In certain embodiments, $L^1$ is of the formula:

In certain embodiments, $L^1$ is of the formula:

In certain embodiments, $L^1$ is of the formula:

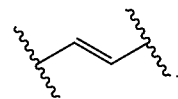

In certain embodiments, $L^2$ is optionally substituted alkylene. In certain embodiments, $L^2$ is optionally substituted heteroalkylene. In certain embodiments, $L^2$ is optionally substituted alkynylene. In certain embodiments, $L^2$ is optionally substituted alkenylene. In certain embodiments, $L^2$ substituted alkenylene. In certain embodiments, $L^2$ is unsubstituted alkenylene. In certain embodiments, $L^2$ is of the formula:

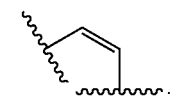 [SMILES: */C=C\*]

In certain embodiments, $L^2$ is of the formula:

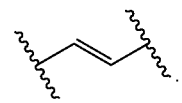

In certain embodiments, $L^2$ is of the formula:

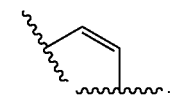 [SMILES: */C=C\*]

In certain embodiments, $L^3$ is optionally substituted alkylene. In certain embodiments, $L^3$ is optionally substituted heteroalkylene. In certain embodiments, $L^3$ is optionally substituted alkynylene. In certain embodiments, $L^3$ is optionally substituted alkenylene. In certain embodiments, $L^3$ substituted alkenylene. In certain embodiments, $L^3$ is unsubstituted alkenylene. In certain embodiments, $L^3$ is of the formula:

In certain embodiments, $L^3$ is of the formula:

In certain embodiments, $L^3$ is of the formula:

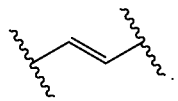

In certain embodiments, $L^4$ is optionally substituted alkylene. In certain embodiments, $L^4$ is optionally substituted heteroalkylene. In certain embodiments, $L^4$ is optionally substituted alkynylene. In certain embodiments, $L^4$ is optionally substituted alkenylene. In certain embodiments, $L^4$ substituted alkenylene. In certain embodiments, $L^4$ is unsubstituted alkenylene. In certain embodiments, $L^4$ is of the formula:

In certain embodiments, $L^4$ is of the formula:

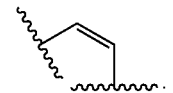 [SMILES: */C=C\*]

In certain embodiments, $L^4$ is of the formula:

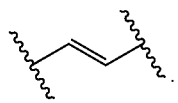

In certain embodiments, the triblock bottlebrush copolymer of Formula (I) is of Formula (I-a):

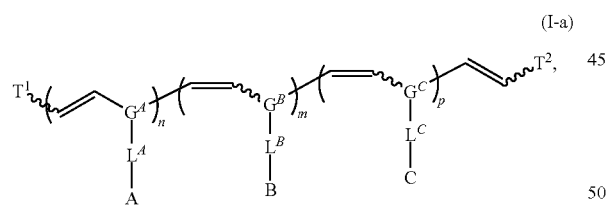

(I-a)

wherein $T^1$, $T^2$, $G^A$, $G^B$, $G^C$, $L^A$, $L^B$, $L^C$, A, B, C, n, m, and p are as described herein.

As generally defined herein, each of $G^A$, $G^B$, and $G^C$ is independently optionally substituted alkylene, optionally substituted heteroalkylene, optionally substituted carbocyclylene, optionally substituted heterocyclylene, optionally substituted arylene, optionally substituted heteroarylene, or a combination thereof. In certain embodiments, each of $G^A$, $G^B$, and $G^C$ are independently optionally substituted carbocyclylene, optionally substituted heterocyclylene, or a combination thereof. In certain embodiments, each of $G^A$, $G^B$, and $G^C$ is optionally substituted carbocyclylene. In certain embodiments, each of $G^A$, $G^B$, and $G^C$ is optionally substituted heterocyclylene. In certain embodiments, each of $G^A$, $G^B$, and $G^C$ comprises optionally substituted 5-membered carbocyclylene or 5-membered heterocyclylene. In certain embodiments, each of $G^A$, $G^B$, and $G^C$ comprises optionally substituted cyclopentylene, cyclohexylene, tetrahydrofuranylene, tetrahydrothiophenylene, or pyrrolidinylene. In certain embodiments, each of $G^A$, $G^B$, and $G^C$ is independently optionally substituted bicyclic heterocyclylene. In certain embodiments, each of $G^A$, $G^B$, and $G^C$ are substituted bicyclic heterocyclylene. In certain embodiments, each of $G^A$, $G^B$, and $G^C$ are of the following formula:

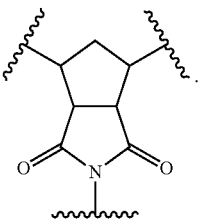 [SMILES: *C1CC(*)C2C(=O)N(*)C(=O)C12 ; "."]

In other embodiments, each of $G^A$, $G^B$, and $G^C$ may independently be of any of the following formulae:

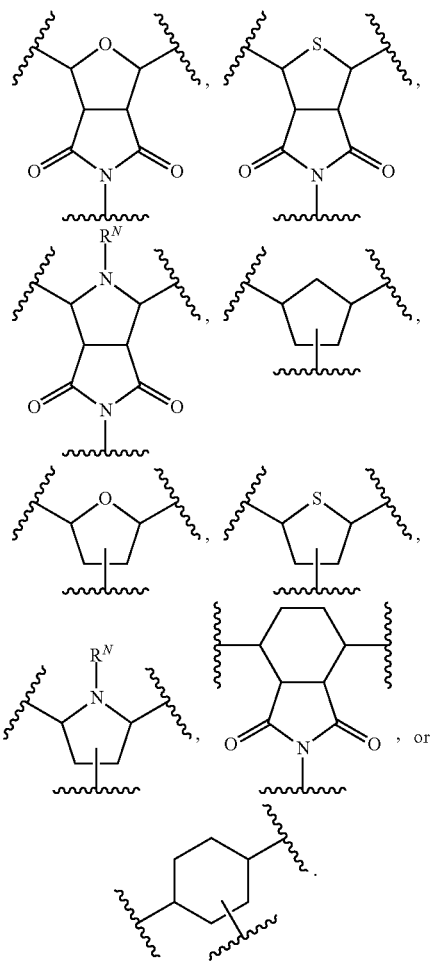

As generally defined herein, $G^A$ is optionally substituted carbocyclylene, optionally substituted heterocyclylene, or a combination thereof. In certain embodiments, $G^A$ is optionally substituted carbocyclylene. In certain embodiments, $G^A$ is optionally substituted heterocyclylene. In certain embodiments, $G^A$ comprises optionally substituted 5-membered carbocyclylene or 5-membered heterocyclylene. In certain embodiments, $G^A$ comprises optionally substituted cyclopentylene, cyclohexylene, tetrahydrofuranylene, tetrahydrothiophenylene, or pyrrolidinylene. In certain embodiments, $G^A$ is optionally substituted bicyclic heterocyclylene. In certain embodiments, $G^A$ is substituted bicyclic heterocyclylene. In certain embodiments, $G^A$ is of the following formula:

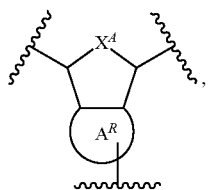

wherein $X^A$ and $A^R$ are as defined herein. In certain embodiments, $G^A$ is of the following formula:

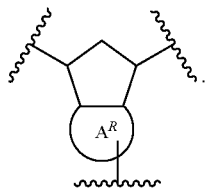

In certain embodiments, $G^A$ is of the following formula:

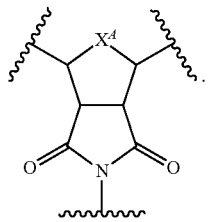

In certain embodiments, $G^A$ is of the following formula:

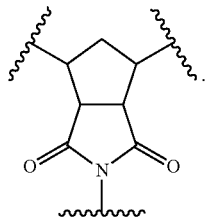 [SMILES: *C1CC(*)C2C(=O)N(*)C(=O)C12 ; "."]

As generally defined herein, $G^B$ is optionally substituted carbocyclylene, optionally substituted heterocyclylene, or a combination thereof. In certain embodiments, $G^B$ is optionally substituted carbocyclylene. In certain embodiments, $G^B$ is optionally substituted heterocyclylene. In certain embodiments, $G^B$ is optionally substituted bicyclic heterocyclylene. In certain embodiments, $G^B$ comprises optionally substituted 5-membered carbocyclylene or 5-membered heterocyclylene. In certain embodiments, $G^B$ comprises optionally substituted cyclopentylene, cyclohexylene, tetrahydrofuranylene, tetrahydrothiophenylene, or pyrrolidinylene. In certain embodiments, $G^B$ is substituted bicyclic heterocyclylene. In certain embodiments, $G^B$ is of the following formula:

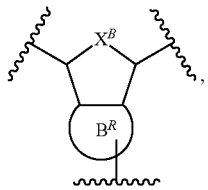

wherein $X^B$ and $B^R$ are as defined herein. In certain embodiments, $G^B$ is of the following formula:

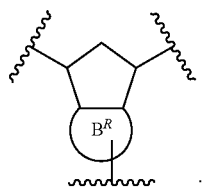

In certain embodiments, $G^B$ is of the following formula:

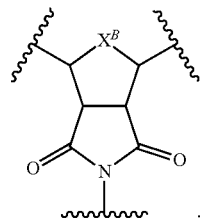

In certain embodiments, $G^B$ is of the following formula:

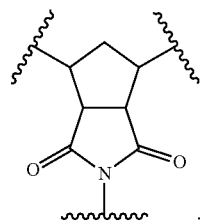 [SMILES: *C1CC(*)C2C(=O)N(*)C(=O)C12]

As generally defined herein, $G^C$ is optionally substituted carbocyclylene, optionally substituted heterocyclylene, or a combination thereof. In certain embodiments, $G^C$ is optionally substituted carbocyclylene. In certain embodiments, $G^C$ is optionally substituted heterocyclylene. In certain embodiments, $G^C$ is optionally substituted bicyclic heterocyclylene. In certain embodiments, $G^C$ comprises optionally substituted 5-membered carbocyclylene or 5-membered heterocyclylene. In certain embodiments, $G^C$ comprises optionally substituted cyclopentylene, cyclohexylene, tetrahydrofuranylene, tetrahydrothiophenylene, or pyrrolidinylene. In certain embodiments, $G^C$ is substituted bicyclic heterocyclylene. In certain embodiments, $G^C$ is of the following formula:

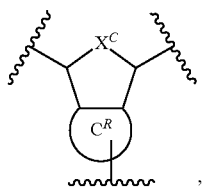

wherein $X^C$ and $C^R$ are as defined herein. In certain embodiments, $G^C$ is of the following formula:

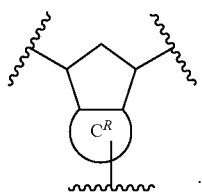

In certain embodiments, $G^C$ is of the following formula:

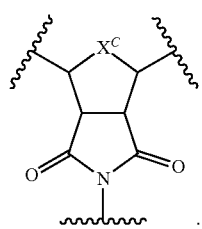

In certain embodiments, $G^C$ is of the following formula:

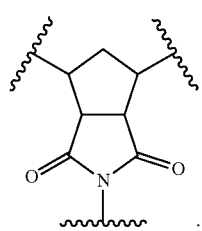 [SMILES: *C1CC(*)C2C(=O)N(*)C(=O)C12]

In certain embodiments, the triblock bottlebrush copolymer of Formula (I) is of Formula (I-b):

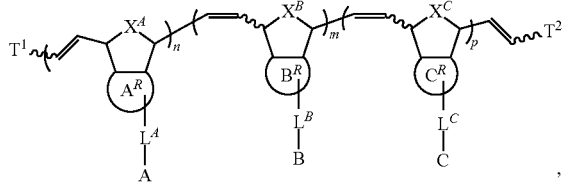

(I-b)

wherein:

each of $X^A$, $X^B$, and $X^C$ is independently selected from the group consisting of —CH$_2$—, —CH$_2$CH$_2$—, —O—, and —S—; and each of $A^R$, $B^R$, and $C^R$ is independently optionally substituted carbocyclyl or optionally substituted heterocyclyl.

As generally defined herein, each of $X^A$, $X^B$, and $X^C$ is independently selected from the group consisting of —CH$_2$—, —CH$_2$CH$_2$—, —O—, and —S—. In certain embodiments, each of $X^A$, $X^B$, and $X^C$ is —CH$_2$—. In certain embodiments, each of $X^A$, $X^B$, and $X^C$ is —CH$_2$CH$_2$—. In certain embodiments, each of $X^A$, $X^B$, and $X^C$ is —O—. In certain embodiments, each of $X^A$, $X^B$, and $X^C$ is —S—. In certain embodiments, $X^A$ is —CH$_2$—. In certain embodiments, $X^A$ is —CH$_2$CH$_2$—. In certain embodiments, $X^A$—O—. In certain embodiments, $X^A$ is —S—. In certain embodiments, $X^B$ is —CH$_2$—. In certain embodiments, $X^B$ is —CH$_2$CH$_2$—. In certain embodiments, $X^B$—O—. In certain embodiments, $X^B$ is —S—. In certain embodiments, $X^C$ is —CH$_2$—. In certain embodiments, $X^C$ is —CH$_2$CH$_2$—. In certain embodiments, $X^C$—O—. In certain embodiments, $X^C$ is —S—.

In certain embodiments, the triblock bottlebrush copolymer of Formula (I) is of Formula (I-c):

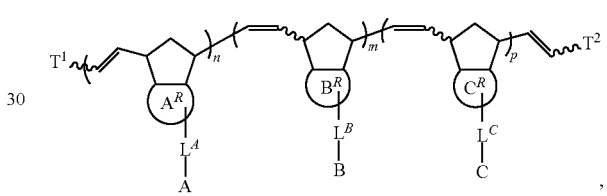

(I-c)

wherein $T^1$, $T^2$, $A^R$, $B^R$, $C^R$, $L^A$, $L^B$, $L^C$, A, B, C, n, m, and p are as defined herein.

As generally defined herein, each of $A^R$, $B^R$, and $C^R$ is independently optionally substituted carbocyclyl or optionally substituted heterocyclyl. In certain embodiments, each of $A^R$, $B^R$, and $C^R$ is optionally substituted carbocyclyl. In certain embodiments, each of $A^R$, $B^R$, and $C^R$ is optionally substituted heterocyclyl. In certain embodiments, each of $A^R$, $B^R$, and $C^R$ is optionally substituted five-membered heterocyclyl. In certain embodiments, each of $A^R$, $B^R$, and $C^R$ is a succinimide ring. In certain embodiments, $A^R$ is optionally substituted carbocyclyl. In certain embodiments, $A^R$ is optionally substituted heterocyclyl. In certain embodiments, $A^R$ is optionally substituted five-membered heterocyclyl. In certain embodiments, $A^R$ is a succinimide ring. In certain embodiments, $A^R$ is optionally substituted carbocyclyl. In certain embodiments, $B^R$ is optionally substituted heterocyclyl. In certain embodiments, $B^R$ is optionally substituted five-membered heterocyclyl. In certain embodiments, $B^R$ is a succinimide ring. In certain embodiments, $C^R$ is optionally substituted carbocyclyl. In certain embodiments, $C^R$ is optionally substituted heterocyclyl. In certain embodiments, $C^R$ is optionally substituted five-membered heterocyclyl. In certain embodiments, $C^R$ is a succinimide ring.

In certain embodiments, the triblock bottlebrush copolymer of Formula (I) is a triblock bottlebrush copolymer of Formula (I-d):

(I-d)

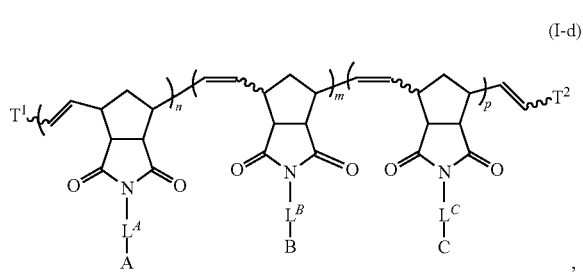

wherein $T^1$, $T^2$, $L^A$, $L^B$, $L^C$, A, B, C, n, m, and p are as defined herein.

As generally defined herein, each of $T^1$ and $T^2$ is independently a terminal group selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thiol. In certain embodiments, $T^1$ is hydrogen. In certain embodiments, $T^1$ is halogen. In certain embodiments, $T^1$ is optionally substituted alkyl. In certain embodiments, $T^1$ is optionally substituted alkenyl. In certain embodiments, $T^1$ is optionally substituted alkynyl. In certain embodiments, $T^1$ is optionally substituted carbocyclyl. In certain embodiments, $T^1$ is optionally substituted heterocyclyl. In certain embodiments, $T^1$ is optionally substituted aryl. In certain embodiments, $T^1$ is optionally substituted phenyl. In certain embodiments, $T^1$ is unsubstituted phenyl (-Ph). In certain embodiments, $T^1$ is optionally substituted heteroaryl. In certain embodiments, $T^1$ is optionally substituted acyl. In certain embodiments, $T^1$ is optionally substituted hydroxyl. In certain embodiments, $T^1$ is optionally substituted amino. In certain embodiments, $T^1$ is optionally substituted thiol. In certain embodiments, $T^2$ is hydrogen. In certain embodiments, $T^2$ is halogen. In certain embodiments, $T^2$ is optionally substituted alkyl. In certain embodiments, $T^2$ is optionally substituted alkenyl. In certain embodiments, $T^2$ is optionally substituted alkynyl. In certain embodiments, $T^2$ is optionally substituted carbocyclyl. In certain embodiments, $T^2$ is optionally substituted heterocyclyl. In certain embodiments, $T^2$ is optionally substituted aryl. In certain embodiments, $T^2$ is optionally substituted phenyl. In certain embodiments, $T^2$ is unsubstituted phenyl (-Ph). In certain embodiments, $T^2$ is optionally substituted heteroaryl. In certain embodiments, $T^2$ is optionally substituted acyl. In certain embodiments, $T^2$ is optionally substituted hydroxyl. In certain embodiments, $T^2$ is optionally substituted amino. In certain embodiments, $T^2$ is optionally substituted thiol. In certain embodiments, both $T^1$ and $T^2$ are hydrogen.

In certain embodiments, the copolymer of Formula (I) is of Formula (I-e):

(I-e)

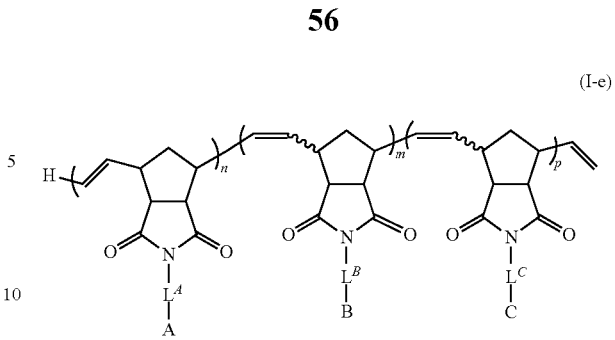

In certain embodiments, the copolymer of Formula (I) is of the following formula:

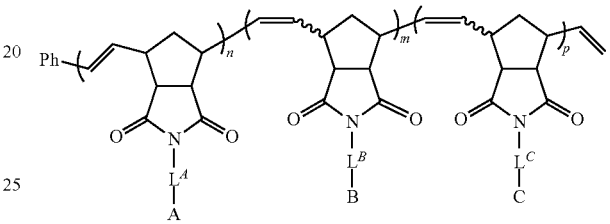

As generally defined herein, each of $L^A$, $L^B$, and $L^C$ is independently a linker selected from the group consisting of optionally substituted alkylene, optionally substituted heteroalkylene, optionally substituted carbocyclylene, optionally substituted heterocyclylene, optionally substituted arylene, optionally substituted heteroarylene, and combinations thereof. In certain embodiments, at least one of $L^A$, $L^B$, and $L^C$ comprises optionally substituted alkylene. In certain embodiments, at least one of $L^A$, $L^B$, and $L^C$ is optionally substituted $C_{1-20}$ alkylene. In certain embodiments, at least one of $L^A$, $L^B$, and $L^C$ is optionally substituted $C_{1-6}$ alkylene. In certain embodiments, at least one of $L^A$, $L^B$, and $L^C$ is unsubstituted $C_{1-6}$ alkylene. For example, in certain embodiments, at least one of $L^A$, $L^B$, and $L^C$ is of the formula:

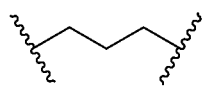

In certain embodiments, at least one of $L^A$, $L^B$, and $L^C$ comprises optionally substituted heteroalkylene. In certain embodiments, at least one of $L^A$, $L^B$, and $L^C$ is optionally substituted $C_1$-20 heteroalkylene. In certain embodiments, at least one of $L^A$, $L^B$, and $L^C$ is optionally substituted $C_{1-6}$ heteroalkylene. In certain embodiments, at least one of $L^A$, $L^B$, and $L^C$ is substituted $C_{1-6}$ heteroalkylene. For example, in certain embodiments, at least one of $L^A$, $L^B$, and $L^C$ is of the formula:

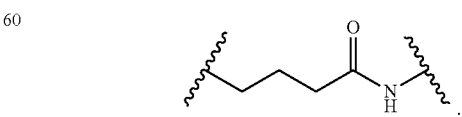

As a further example, in certain embodiments, at least one of $L^A$, $L^B$, and $L^C$ is of the formula:

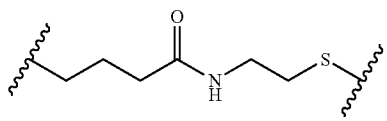

In certain embodiments, at least one of $L^A$, $L^B$, and $L^C$ comprises optionally substituted carbocyclylene. In certain embodiments, at least one of $L^A$, $L^B$, and $L^C$ comprises optionally substituted heterocyclylene. In certain embodiments, at least one of $L^A$, $L^B$, and $L^C$ comprises optionally substituted arylene. In certain embodiments, at least one of $L^A$, $L^B$, and $L^C$ comprises optionally substituted heteroarylene.

In certain embodiments, $L^A$ comprises optionally substituted alkylene. In certain embodiments, $L^A$ is optionally substituted $C_{1-20}$ alkylene. In certain embodiments, $L^A$ is optionally substituted $C_{1-6}$ alkylene. In certain embodiments, $L^A$ is unsubstituted $C_{1-6}$ alkylene. For example, in certain embodiments, $L^A$ is of the formula:

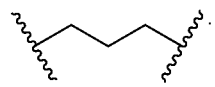

In certain embodiments, $L^A$ comprises optionally substituted heteroalkylene. In certain embodiments, $L^A$ is optionally substituted $C_{1-20}$ heteroalkylene. In certain embodiments, $L^A$ is optionally substituted $C_{1-6}$ heteroalkylene. In certain embodiments, $L^A$ is substituted $C_{1-6}$ heteroalkylene. For example, in certain embodiments, $L^A$ is of the formula:

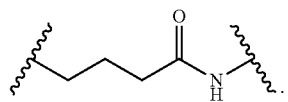 [SMILES: *CCCC(=O)N*]

As a further example, in certain embodiments, $L^A$ is of the formula:

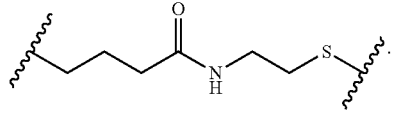 [SMILES: *CCCC(=O)NCCS*]

In certain embodiments, $L^A$ comprises optionally substituted carbocyclylene. In certain embodiments, $L^A$ comprises optionally substituted heterocyclylene. In certain embodiments, $L^A$ comprises optionally substituted arylene. In certain embodiments, $L^A$ comprises optionally substituted heteroarylene.

In certain embodiments, $L^B$ comprises optionally substituted alkylene. In certain embodiments, $L^B$ is optionally substituted $C_{1-20}$ alkylene. In certain embodiments, $L^B$ is optionally substituted $C_{1-6}$ alkylene. In certain embodiments, $L^B$ is unsubstituted $C_{1-6}$ alkylene. For example, in certain embodiments, $L^B$ is of the formula:

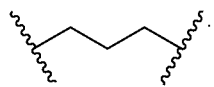 [SMILES: *CCC*]

In certain embodiments, $L^B$ comprises optionally substituted heteroalkylene. In certain embodiments, $L^B$ is optionally substituted $C_1$-20 heteroalkylene. In certain embodiments, $L^B$ is optionally substituted $C_{1-6}$ heteroalkylene. In certain embodiments, $L^B$ is substituted $C_{1-6}$ heteroalkylene. For example, in certain embodiments, $L^B$ is of the formula:

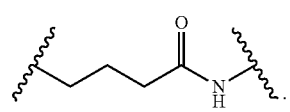

As a further example, in certain embodiments, $L^B$ is of the formula:

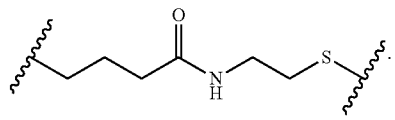

In certain embodiments, $L^B$ comprises optionally substituted carbocyclylene. In certain embodiments, $L^B$ comprises optionally substituted heterocyclylene. In certain embodiments, $L^B$ comprises optionally substituted arylene. In certain embodiments, $L^B$ comprises optionally substituted heteroarylene.

In certain embodiments, $L^C$ comprises optionally substituted alkylene. In certain embodiments, $L^C$ is optionally substituted $C_{1-20}$ alkylene. In certain embodiments, $L^C$ is optionally substituted $C_{1-6}$ alkylene. In certain embodiments, $L^C$ is unsubstituted $C_{1-6}$ alkylene. For example, in certain embodiments, $L^C$ is of the formula:

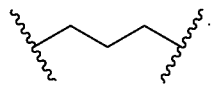 [SMILES: *CCC*]

In certain embodiments, $L^C$ comprises optionally substituted heteroalkylene. In certain embodiments, $L^C$ is optionally substituted $C_{1-20}$ heteroalkylene. In certain embodiments, $L^C$ is optionally substituted $C_{1-6}$ heteroalkylene. In certain embodiments, $L^C$ is substituted $C_{1-6}$ heteroalkylene. For example, in certain embodiments, $L^C$ is of the formula:

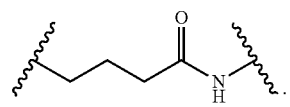

As a further example, in certain embodiments, $L^C$ is of the formula:

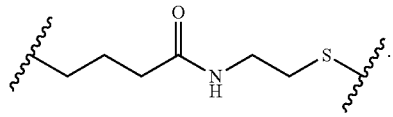 [SMILES: *CCCC(=O)NCCS*]

In certain embodiments, $L^C$ comprises optionally substituted carbocyclylene. In certain embodiments, $L^C$ comprises optionally substituted heterocyclylene. In certain embodiments, $L^C$ comprises optionally substituted arylene. In certain embodiments, $L^C$ comprises optionally substituted heteroarylene.

In certain embodiments of the invention, a triblock bottlebrush copolymer of Formula (I) is of Formula (I-d):

(I-d)

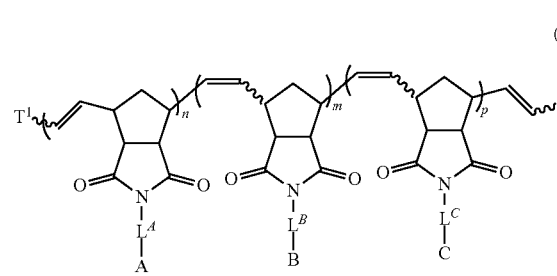

wherein all of A are of one of the following formulae:

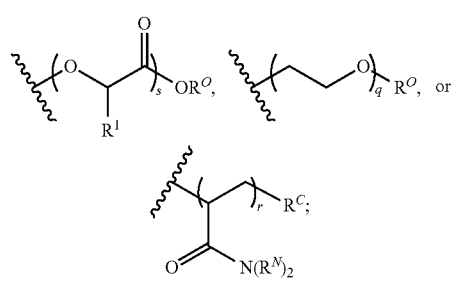

all of B are of one of the following formulae:

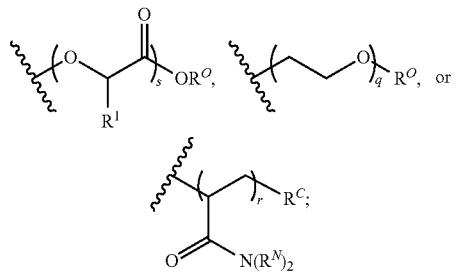

and
all of C are of one of the following formulae:

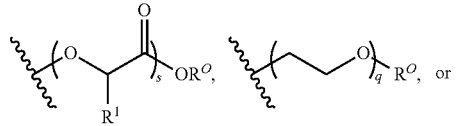

provided that A, B, and C are of different formula.

In certain embodiments of the invention, a triblock bottlebrush copolymer of Formula (I) is of Formula (I-e):

(I-e)

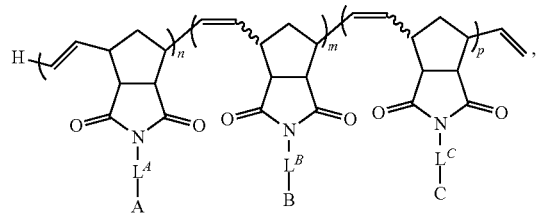

wherein all of $-L^A$-A are of one of the following formulae:

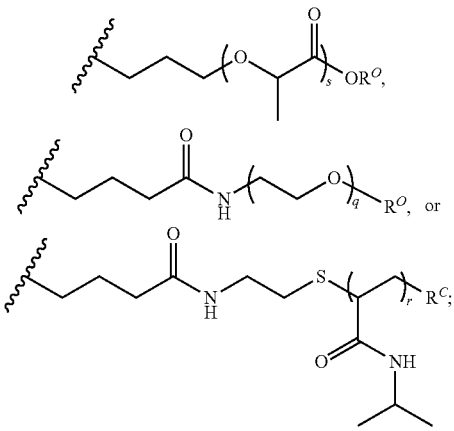

all of $-L^B$-B are of one of the following formulae:

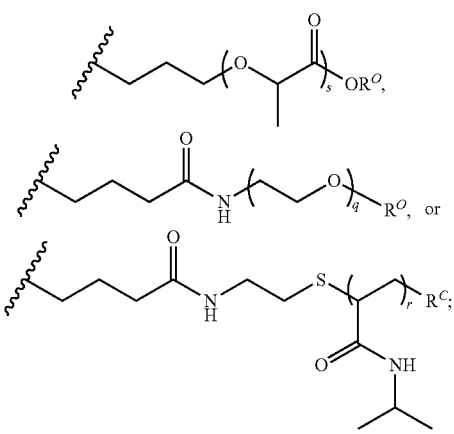

and
all of -L$^C$-C is are one of the following formulae:

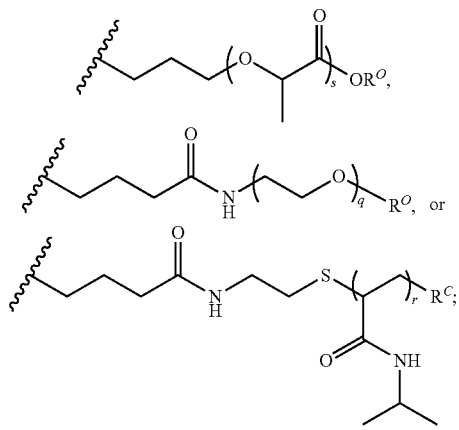

provided that -L$^A$-A, -L$^B$-B, and -L$^C$-C are of different formula.

In certain embodiments of the invention, a triblock bottlebrush copolymer of Formula (I) is of the formula:

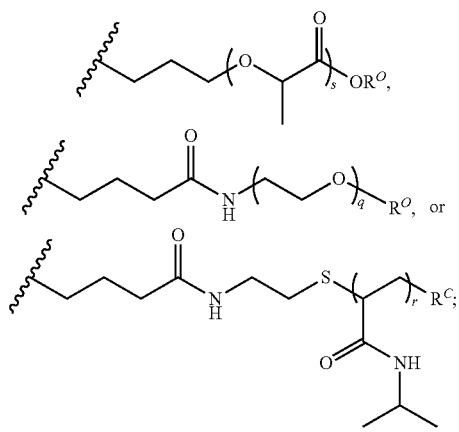

wherein all of -L$^A$-A are of one of the following formulae:

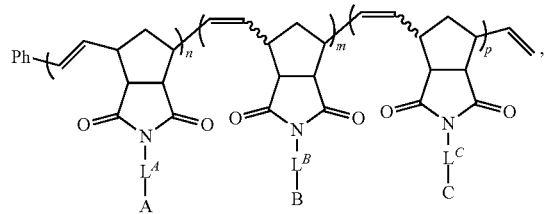

all of -L$^B$-B are of one of the following formulae:

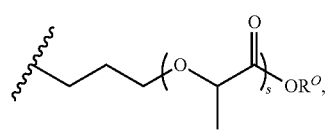

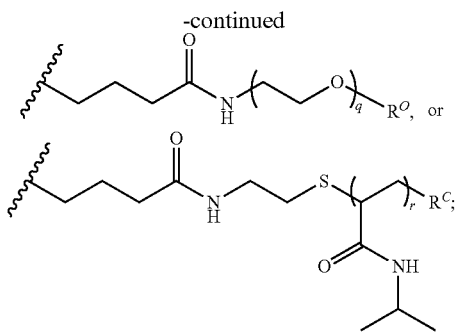

and
all of -L$^C$-C are of one of the following formulae:

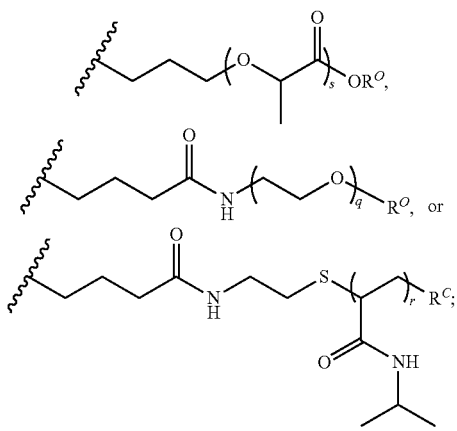

provided that -L$^A$-A, -L$^B$-B, and -L$^C$-C are of different formula.

In certain embodiments, group A is a polyester group, group B is a polyether group, and group C is a polyacrylamide group. For instance, in certain embodiments, group A is PLA, group B is PEG, and group C is PNIPAM. In certain embodiments, group A is a polyacrylamide group, group B is a polyester group, and group C is a polyether group. For example, in certain embodiments, group A is PNIPAM, group B is PLA, and group C is PEG. In certain embodiments of the triblock bottlebrush copolymers described herein, one of group A, B, or C is replaced by a different polymer group.

In certain embodiments, each of group A is PLA; each of group B is PEG; and each of group C is PNIPAM; and the triblock bottlebrush copolymer of Formula (I) is of Formula (II):

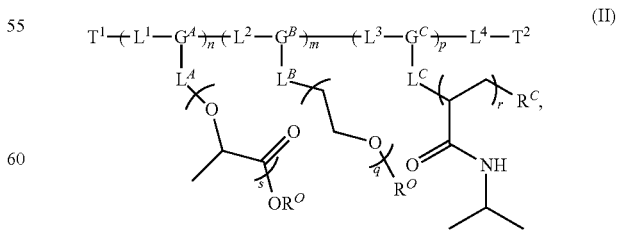

wherein $T^1$, $T^2$, $L^1$, $L^2$, $L^3$, $L^4$, $L^A$, $L^B$, $L^C$, $G^A$, $G^B$, $G^C$, $R^O$, $R^C$, n, m, p, s, r, and q are as defined herein.

In certain embodiments, the triblock bottlebrush copolymer of Formula (II) is of Formula (II-a):

(II-a)

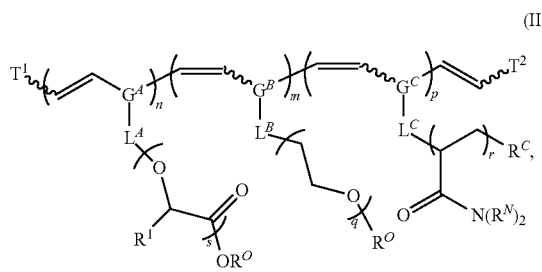

wherein $T^1$, $T^2$, $L^A$, $L^B$, $L^C$, $G^A$, $G^B$, $G^C$, $R^O$, $R^C$, n, m, p, s, r, and q are as defined herein.

In certain embodiments, the triblock bottlebrush copolymer of Formula (II) is of Formula (II-b):

(II-b)

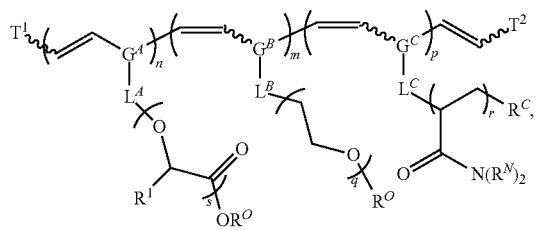

wherein $T^1$, $T^2$, $L^A$, $L^B$, $L^C$, $G^A$, $G^B$, $G^C$, $R^O$, $R^C$, n, m, p, s, r, and q are as defined herein.

In certain embodiments, the triblock bottlebrush copolymer of Formula (II) is of Formula (II-c):

(II-c)

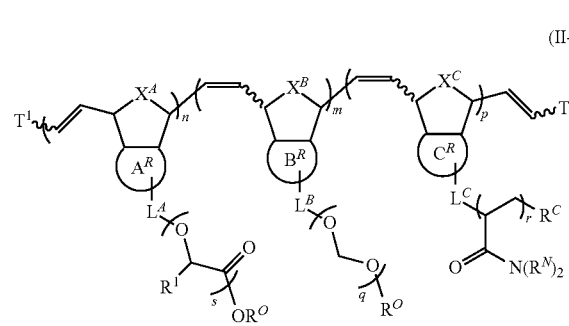

wherein $T^1$, $T^2$, $L^A$, $L^B$, $L^C$, $X^A$, $X^B$, $X^C$, $A^R$, $B^R$, $C^R$, $R^O$, $R^C$, n, m, p, s, r, and q are as defined herein.

In certain embodiments, the triblock bottlebrush copolymer of Formula (II) is of Formula (II-d):

(II-d)

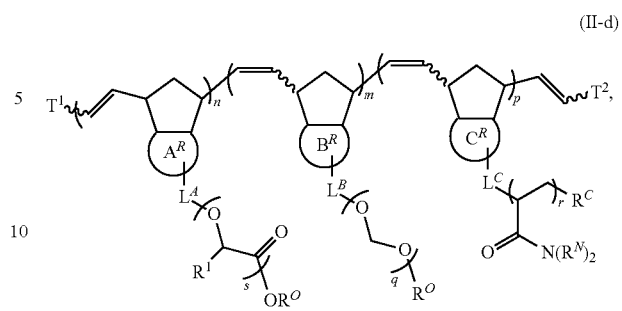

wherein $T^1$, $T^2$, $L^A$, $L^B$, $L^C$, $A^R$, $B^R$, $C^R$, $R^O$, $R^C$, n, m, p, s, r, and q are as defined herein.

In certain embodiments, the triblock bottlebrush copolymer of Formula (II) is of Formula (II-e):

(II-e)

wherein $T^1$, $T^2$, $L^A$, $L^B$, $L^C$, $A^R$, $B^R$, $C^R$, $R^O$, $R^C$, n, m, p, s, r, and q are as defined herein.

In certain embodiments, the triblock bottlebrush copolymer of Formula (II) is of Formula (II-f):

(II-f)

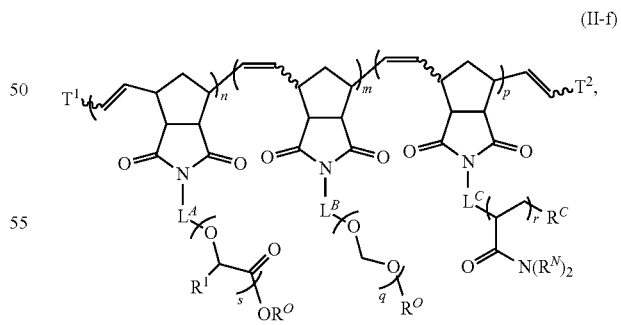

wherein $T^1$, $T^2$, $L^A$, $L^B$, $L^C$, $R^O$, $R^C$, n, m, p, s, r, and q are as defined herein.

In certain embodiments, the triblock bottlebrush copolymer of Formula (II) is of Formula (II-g):

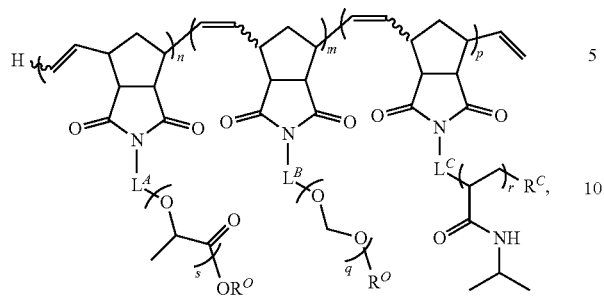

(II-g)

wherein $L^A$, $L^B$, $L^C$, $R^O$, $R^C$, n, m, p, s, r, and q are as defined herein.

In certain embodiments, the triblock bottlebrush copolymer of Formula (II) is of the following formula:

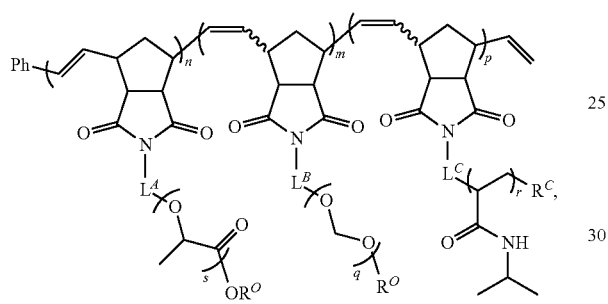

wherein $L^A$, $L^B$, $L^C$, $R^O$, $R^C$, n, m, p, s, r, and q are as defined herein.

For example, in certain embodiments, a triblock bottlebrush copolymer is of the following formula:

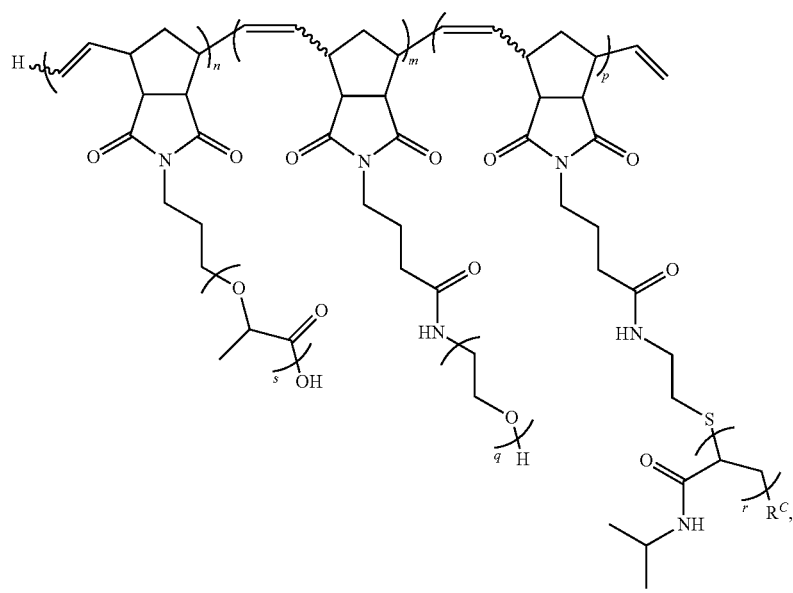

wherein n, m, p, s, r, and q are as defined herein.

For example, in certain embodiments, a triblock bottlebrush copolymer is of the following formula:

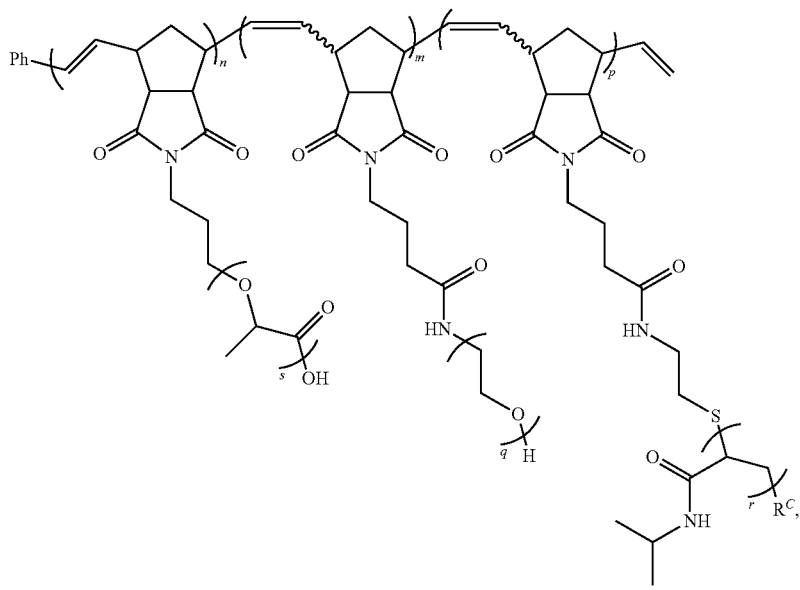
wherein n, m, p, s, r, and q are as defined herein.
For example, in certain embodiments, a triblock bottle-brush copolymer is of the following formula:
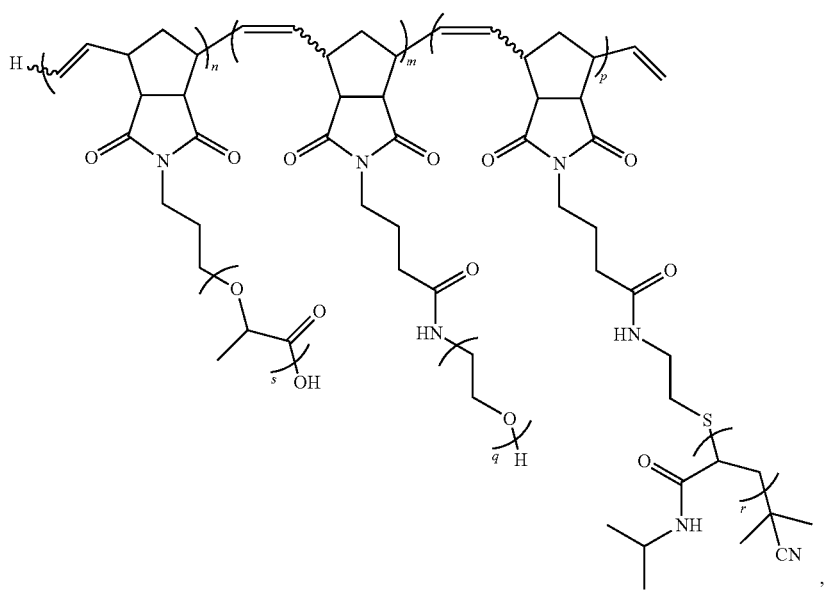
wherein n, m, p, s, r, and q are as defined herein.
For example, in certain embodiments, a triblock bottle-brush copolymer is of the following formula:

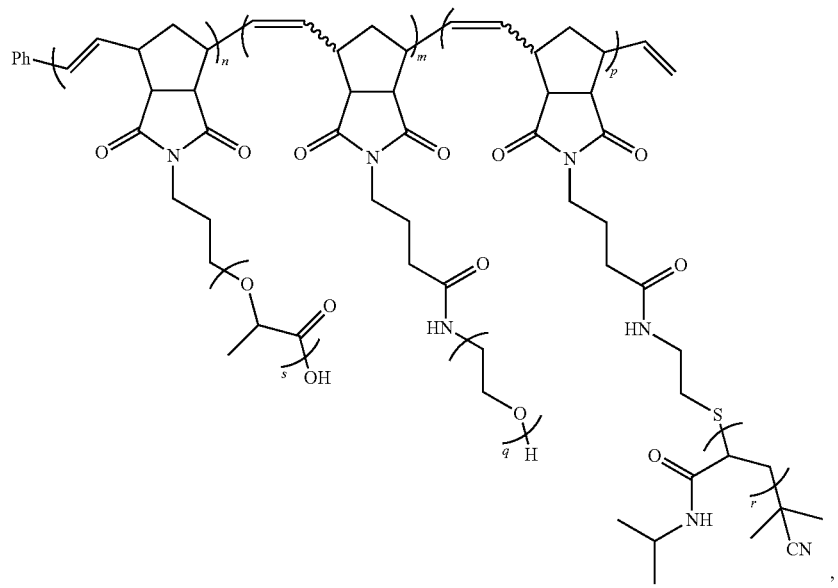
wherein n, m, p, s, r, and q are as defined herein.
For example, in certain embodiments, a triblock bottle-brush copolymer is of the following formula:
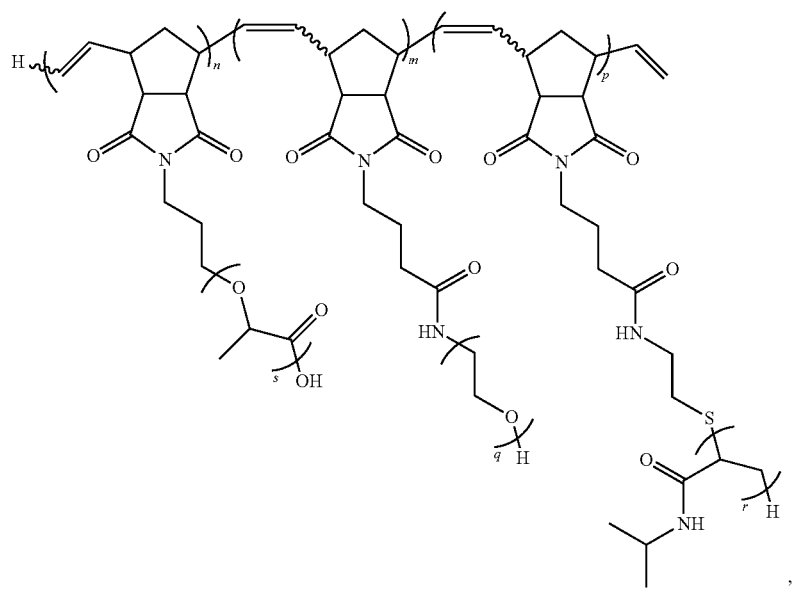
wherein n, m, p, s, r, and q are as defined herein.
For example, in certain embodiments, a triblock bottle-brush copolymer is of the following formula:

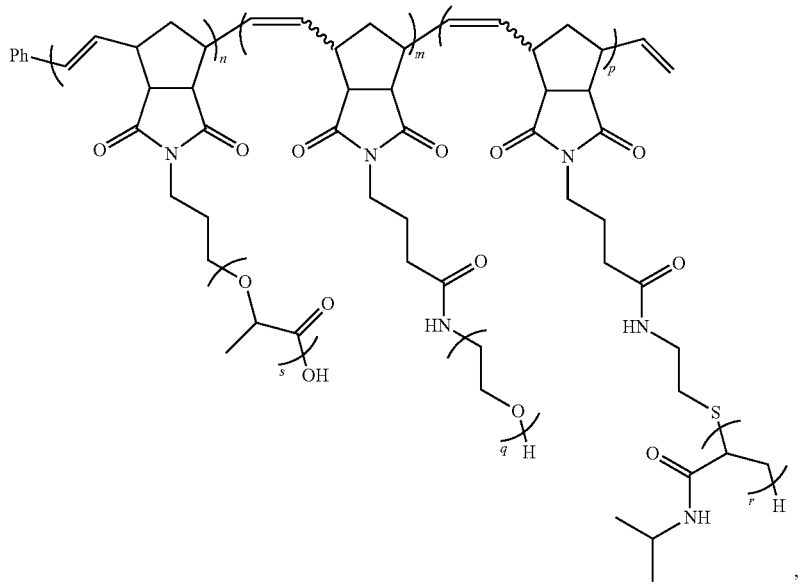

wherein n, m, p, s, r, and q are as defined herein.

As generally defined herein, n is an integer between 1 and 4000, inclusive. In certain embodiments, n is an integer between 5 and 4000, inclusive. In certain embodiments, n is an integer is between 50 and 4000, inclusive. In certain embodiments, n is an integer between 100 and 4000, inclusive. In certain embodiments, n is an integer between 1000 and 4000, inclusive. In certain embodiments, n is an integer between 2000 and 4000, inclusive. In certain embodiments, n is an integer between 2 and 4000, inclusive. In certain embodiments, n is an integer between 2 and 2000, inclusive. In certain embodiments, n is an integer between 2 and 1000, inclusive. In certain embodiments, n is an integer between 2 and 100, inclusive. In certain embodiments, n is an integer between 2 and 50, inclusive. In certain embodiments, n is an integer between 5 and 20, inclusive. In certain embodiments, n is about 10.

As generally defined herein, m is an integer between 1 and 4000, inclusive. In certain embodiments, m is an integer between 5 and 4000, inclusive. In certain embodiments, m is an integer is between 50 and 4000, inclusive. In certain embodiments, m is an integer between 100 and 4000, inclusive. In certain embodiments, m is an integer between 1000 and 4000, inclusive. In certain embodiments, m is an integer between 2000 and 4000, inclusive. In certain embodiments, m is an integer between 2 and 4000, inclusive. In certain embodiments, m is an integer between 2 and 2000, inclusive. In certain embodiments, m is an integer between 2 and 1000, inclusive. In certain embodiments, m is an integer between 2 and 100, inclusive. In certain embodiments, m is an integer between 2 and 60, inclusive. In certain embodiments, m is an integer between 20 and 60, inclusive. In certain embodiments, m is about 40.

As generally defined herein, p is an integer between 1 and 4000, inclusive. In certain embodiments, p is an integer between 5 and 4000, inclusive. In certain embodiments, p is an integer is between 50 and 4000, inclusive. In certain embodiments, p is an integer between 100 and 4000, inclusive. In certain embodiments, p is an integer between 1000 and 4000, inclusive. In certain embodiments, p is an integer between 2000 and 4000, inclusive. In certain embodiments, p is an integer between 2 and 4000, inclusive. In certain embodiments, p is an integer between 2 and 2000, inclusive. In certain embodiments, p is an integer between 2 and 1000, inclusive. In certain embodiments, p is an integer between 2 and 100, inclusive. In certain embodiments, p is an integer between 2 and 50, inclusive. In certain embodiments, p is an integer between 5 and 20, inclusive. In certain embodiments, p is about 10.

The properties of a triblock bottlebrush copolymer described herein may be dependent upon the ratio of Block A to Block B to Block C in the copolymer. In certain embodiments, the ratio of Block A to Block B to Block C repeating backbone units in the triblock bottlebrush copolymer is (5 to 20):(30 to 60):(5 to 20). In certain embodiments, the ratio of Block A to Block B to Block C repeating backbone units in the triblock bottlebrush copolymer is (5 to 15):(30 to 50):(5 to 15). For example, in certain embodiments, the ratio of Block A to Block B to Block C repeating backbone units in the triblock bottlebrush copolymer is about 10:40:10. In certain embodiments, the ratio of polyester to polyether to polyacrylamide (by molecular weight) in the triblock bottlebrush copolymer is (5 to 20):(30 to 60):(5 to 20). In certain embodiments, the ratio of polyester to polyether to polyacrylamide (by molecular weight) in the triblock bottlebrush copolymer is (5 to 15):(30 to 50):(5 to 15). For example, in certain embodiments, the ratio of polyester to polyether to polyacrylamide (by molecular weight) in the triblock bottlebrush copolymer is about 10:40:10.

As described herein, in certain embodiments, a triblock bottlebrush copolymer of the present invention has a bottlebrush, comb, or graft-copolymer structure. In certain embodiments, the copolymer has a bottlebrush structure. In certain embodiments, the copolymer has a comb structure. In certain embodiments, the copolymer has a graft-copolymer structure. A triblock bottlebrush copolymer described herein may self-assemble to form any type of polymer network or nanostructure. In certain embodiments, a triblock bottlebrush copolymer described herein self-assembles to form particles or micelles. In certain embodiments, a triblock bottlebrush copolymer described herein self-assembles to form a spherical, lamellar, cylindrical, ellipsoidal, polyhedral, or gyroid shape.

Triblock bottlebrush copolymers described herein may comprise one or more additional blocks (e.g., to forma tetrablock bottlebrush copolymer in the case of one additional block).

Methods for Preparing Triblock Bottlebrush Copolymers

In one aspect, the present invention provides methods for preparing the triblock bottlebrush copolymers described herein. The methods comprise forming the triblock bottlebrush copolymer via a polymerization reaction or series of subsequent polymerization reactions, and any polymerization reactions known in the art may be employed. Examples of polymerization reactions include, but are not limited to, free-radical polymerization, cationic polymerization, anionic polymerization, and olefin metathesis polymerization (e.g., ring-opening metathesis polymerization (abbreviated "ROMP")).

A method of preparing a triblock bottlebrush copolymer described herein may comprise two or more sequential polymerization steps. For instance, a first macromonomer may be polymerized to form a homopolymer. Then, the homopolymer can be polymerized with a second macromonomer to form a diblock copolymer. Then, the diblock polymer can be polymerized with a third macromonomer to form an ABC triblock bottlebrush copolymer.

Provided herein is a method of producing a triblock bottlebrush copolymer described herein, the method comprising the steps of:

(a) providing a first macromonomer comprising a first polymer and one or more reactive moieties;

(b) providing a second macromonomer comprising a second polymer and one or more reactive moieties;

(c) providing a third macromonomer comprising a third polymer and one or more reactive moieties;

(d) reacting the macromonomer provided in step (a) under conditions suitable to effect a polymerization reaction and yield a homopolymer;

(e) reacting the homopolymer in step (d) with the macromonomer provided in step (b) under conditions suitable to effect a polymerization reaction and yield a diblock copolymer;

(f) reacting the diblock copolymer in step (e) with the macromonomer provided in step (c) under conditions suitable to effect a polymerization reaction and yield a triblock copolymer.

In certain embodiments, the method of preparing a triblock bottlebrush copolymer described herein comprises one or more olefin metathesis polymerization steps (e.g., steps (d), (e), and/or (f)). In certain embodiments, the method of preparing a triblock bottlebrush copolymer described herein comprises one or more ROMP steps (e.g., steps (d), (e), and/or (f)). Ring-opening metathesis polymerization (ROMP) is a olefin metathesis strategy for chain-growth polymerization that utilizes ring strain of cyclic olefins (e.g., norbornene or cyclopentane; or heterocyclic analogs thereof) to drive the polymerization reaction. For olefin metathesis polymerization, the one or more reactive moieties on the macromonomers are olefins. For ROMP reactions, the one or more reactive moieties are cyclic olefins (e.g., norbornene or cyclopentane; or heterocyclic analogs thereof).

Therefore, in certain embodiments, the method of producing a triblock bottlebrush copolymer described herein comprises steps of:

(a) providing a first macromonomer comprising a first polymer (e.g., a polymeric sidechain described herein) and one or more olefins (e.g., a cyclic olefin);

(b) providing a second macromonomer comprising a second polymer (e.g., a polymeric sidechain described herein) and one or more olefins (e.g., a cyclic olefin);

(c) providing a third macromonomer comprising a third polymer (e.g., a polymeric sidechain described herein) and one or more olefins (e.g., a cyclic olefin);

(d) reacting the macromonomer provided in step (a) under conditions suitable to effect a polymerization reaction and yield a homopolymer;

(e) reacting the homopolymer in step (d) with the macromonomer provided in step (b) under conditions suitable to effect a polymerization reaction and yield a diblock copolymer;

(f) reacting the diblock copolymer in step (e) with the macromonomer provided in step (c) under conditions suitable to effect a polymerization reaction and yield a triblock copolymer.

A "macromonomer" is a monomer comprising a polymer group (e.g., a polymeric sidechain described herein) and a reactive moiety (e.g., an olefin such as a cyclic olefin). In general, a macromonomer is a polymer comprising a reactive group that allows it to act as a monomer in a polymerization reaction. The reactive group may be anywhere on the polymer and may be at the end/terminus of the polymer chain. Macromonomers function as monomers in polymerization reactions and, after polymerization, are the repeating units in the larger triblock bottlebrush copolymer.

For example, in certain embodiments, macromonomers of the present invention are of the following formulae:

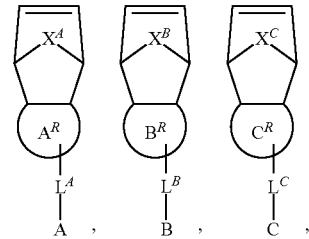

or salts thereof; wherein $X^A$, $X^B$, $X^C$, $A^R$, $B^R$, $C^R$, $L^A$, $L^B$, $L^C$, A, B, and C are as defined herein. In the exemplary macromonomers shown above, the cyclic olefins represent reactive moieties and A, B, and C represent polymer groups.

In certain embodiments, the reactive moieties are cyclic olefins such as norbornene (or variants thereof). For example, in certain embodiments, macromonomers of the present invention are of the following formulae:

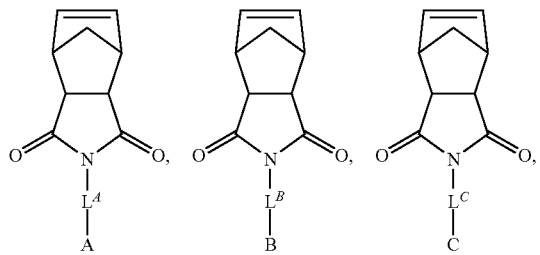

or salts thereof, wherein $L^A$, $L^B$, $L^C$, A, B, and C are as defined herein. Further examples of macromonomers of the present invention are provided in the Examples below.

In order to effect a polymerization reaction to form a triblock bottlebrush copolymer described herein, macromonomers are reacted in the presence of a polymerization initiator. In certain embodiments, when polymerization reaction is an olefin metathesis polymerization reaction (e.g., ROMP), the polymerization initiator is a catalyst or promoter of olefin metathesis. In certain embodiments, a ROMP polymerization involves reacting macromonomers in the presence of a ruthenium complex. In certain embodiments, the ruthenium complex is what is known in the art as a Grubbs or Grubbs-Hoveyda catalyst. Examples of commercially available ruthenium complexes useful in the polymerization reactions described herein can be found on the internet (See, e.g., www.sigmaaldrich.com/chemistry/chemical-synthesis/technology-spotlights/metathesis.html).

In certain embodiments, a ruthenium complex useful in a ROMP reaction described herein is of the following formula:

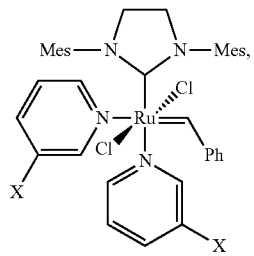

wherein X is a halogen (e.g., Br) or hydrogen.

For examples of olefin metathesis reagents, catalysts, and reaction conditions useful in the present methods, see, e.g., Schrodi, Y.; Pederson, R. L. *Aldrichimica Acta* 2007, 40, 45; *Adv. Synth. Catal.* 2007, 349, 1-268; Grubbs, R. H. *Tetrahedron* 2004, 60, 7117; *Handbook of Metathesis*; Grubbs, R. H., Ed.; Wiley-VCH: Weinheim, 2003; Vols. 1-3; Trnka, T. M.; Grubbs, R. H. *Acc. Chem. Res.* 2001, 34, 18; Fürstner, A. *Angew. Chem., Int. Ed.* 2000, 39, 3012; Schuster, M.; Blechert, S. *Angew. Chem., Int. Ed.* 1997, 36, 2036; Ritter, T. et al. *Organometallics* 2006, 25, 5740; Chatterjee, A. K. et al. *J. Am. Chem. Soc.* 2000, 122, 3783; Chatterjee, A. K.; Grubbs, R. H. *Org. Lett.* 1999, 1, 1751; Murelli, R. P.; Snapper, M. L. *Org. Lett.* 2007, 9, 1749; Stewart, I. C. et al. *Org. Lett.* 2007, 9, 1589; Ung, T. et al. *Organometallics* 2004, 23, 5399; Benitez, D.; Goddard, W. A., III. *J. Am. Chem. Soc.* 2005, 127, 12218; Love, J. A. et al. *Angew. Chem., Int. Ed.* 2002, 41, 4035; Sanford, M. S. et al. *Organometallics* 2001, 20, 5314; Choi, T.-L.; Grubbs, R. H. *Angew. Chem.* 2003, 115, 1785; Ritter, T. et al. *Organometallics* 2006, 25, 5740; and references cited therein; each of which is incorporated herein by reference.

Particles and Hydrogels

As described herein, triblock bottlebrush copolymers of the present invention may self-assemble to form particles (e.g., micelles, nanoparticles, microparticles, particles, liposomes). Therefore, another aspect of the present invention relates to particles comprising a triblock bottlebrush copolymer described herein. In certain embodiments, the particle comprising a triblock bottlebrush copolymer described herein is a nanoparticle. The term "nanoparticle" refers to a particle having an average (e.g., mean) dimension (e.g., diameter) of between about 1 nanometer (nm) and about 1 micrometer (μm). For example, a nanoparticle may have a diameter from 1 nm to 500 nm, from 1 nm to 400 nm, from 1 nm to 300 nm, from 1 nm to 100 nm, from 1 nm to 30 nm, from 1 nm to about 10 nm, or from 1 nm to 3 nm; each range being inclusive. In certain embodiments, the nanoparticle has a diameter from 50 nm to 150 nm, inclusive. In certain embodiments, the nanoparticle has a diameter from 70 nm to 130 nm, inclusive. Combinations of these ranges are also within the scope of this invention.

A particle of the present invention comprises a triblock bottlebrush copolymer described herein, and may further comprise one or more additional components including, but not limited to, lipids (e.g., cationic lipids, non-cationic lipids, phospholipids, steroids (e.g., cholesterol)), surfactants, solvents, other polymers (e.g., PEG-containing polymers), small molecules, and fatty acids. In certain embodiments, the additional materials are approved by a regulatory agency, such as the U.S. FDA, for human and/or veterinary use.

A particle described herein may be prepared using any suitable method known in the art, such as precipitation, milling, spray drying, single and double emulsion solvent evaporation, solvent extraction, phase separation, and simple and complex coacervation. In certain embodiments, methods of preparing the particles are the double emulsion process and spray drying. The conditions used in preparing the particles may be altered to yield particles of a desired size or property (e.g., hydrophobicity, hydrophilicity, external morphology, "stickiness", shape, and polydispersity). The method of preparing the particles and the conditions (e.g., solvent, temperature, concentration, and air flow rate) used may also depend on the therapeutic agent being complexed, encapsulated, or mixed, and/or the composition of the matrix.

Methods developed for making particles for delivery of agents that are included in the particles are described in the literature. See, e.g., Doubrow, M., Ed., "Microcapsules and Nanoparticles in Medicine and Pharmacy," CRC Press, Boca Raton, 1992; Mathiowitz and Langer, *J. Controlled Release* 5:13-22, 1987; Mathiowitz et al., *Reactive Polymers* 6:275-283, 1987; Mathiowitz et al., *J. Appl. Polymer Sci.* 35:755-774, 1988. If the particles prepared by any of the methods described herein have a size range outside of the desired range, the particles can be sized, for example, using a sieve, or by centrifugation. Particles described herein may also be a micelle, liposome, or lipoplex.

Particles are useful tools in drug delivery as they can encapsulate agents (e.g., therapeutic agents, drugs), and often confer properties such as improved solubility, improved stability, targeted delivery, or extended release of the agent. Therefore, a particle described herein may contain one or more therapeutic agents. In certain embodiments, a particle described herein encapsulates one or more therapeutic agents. In certain embodiments, a triblock bottlebrush copolymer provided herein is conjugated to one or more therapeutic agents to form a complex, and the complex forms a particle described herein.

As described herein, examples therapeutic agents include, but are not limited to, small molecules, peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. Several other examples of therapeutic agents are provided herein. In certain embodiments, one or more of the therapeutic agents is a small molecule. In certain embodiments, one or more of the therapeutic agents is a hydrophobic small molecule. In certain embodiments, one or more of the therapeutic agents is a small molecule drug. In certain embodiments, one or more of the therapeutic agents is a hydrophobic small molecule drug. In certain embodiments, one or more of the therapeutic agents is selected from the group consisting of non-steroidal anti-inflammatory drugs (NSAIDs), steroids (e.g., corticosteroids), and antibiotics. In certain embodiments, one or more of the therapeutic agents is selected from anti-proliferative agents (e.g., anti-cancer agents, chemotherapeutic agents). In certain embodiments, the particle comprises (e.g., encapsulates) a therapeutically effective amount of one or more therapeutic agents.

In certain embodiments, one or more of the therapeutic agents is an antibiotic. Examples of antibiotics include, but are not limited to, aminoglycosides (e.g., amikacin, gentamicin, kanamycin, neomycin, netilmicin, tobramycin, paromomycin, streptomycin), ansamycins (e.g., geldanamycin, herbimycin, rifaximin), carbapenems (e.g., loracarbef, ertapenem, doripenem, imipenem/cilastatin, meropenem), cephalosporins (e.g., cefadroxil, cefazolin, cefalotin or cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole), glycopeptides (e.g., teicoplanin, vancomycin, telavancin, dalbavancin, oritavancin), lincosamides (e.g., clindamycin, lincomycin), lipopeptide (e.g., daptomycin), macrolides (e.g., azithromycin, clarithromycin, dirithromycin, erythromycin, roxithromycin, troleandomycin, telithromycin, spiramycin), monobactams (e.g., aztreonam), nitrofurans (e.g., furazolidone, nitrofurantoin), oxazolidinones (e.g., linezolid, posizolid, radezolid, torezolid), penicillins (e.g., amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, temocillin, ticarcillin), polypeptides (e.g., bacitracin, colistin, polymyxin b), quinolones/fluoroquinolone (e.g., ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin), sulfonamides (e.g., mafenide, sulfacetamide, sulfadiazine, silver sulfadiazine, sulfadimethoxine, sulfamethizole, sulfamethoxazole, sulfanilimide, sulfasalazine, sulfisoxazole, trimethoprim-sulfamethoxazole, sulfonamidochrysoidine), tetracyclines (e.g., demeclocycline, doxycycline, minocycline, oxytetracycline, tetracycline), drugs against mycobacteria (e.g., clofazimine, dapsone, capreomycin, cycloserine, ethambutol, ethionamide, isoniazid, pyrazinamide, rifampicin, rifabutin, rifapentine, streptomycin), arsphenamine, chloramphenicol, fosfomycin, fusidic acid, metronidazole, mupirocin, platensimycin, quinupristin/dalfopristin, thiamphenicol, tigecycline, tinidazole, trimethoprim, and teixobactin.

In certain embodiments, one or more of the therapeutic agents is a non-steroidal anti-inflammatory drug. Examples of non-steroidal anti-inflammatory drugs (NSAIDs) include, but are not limited to, salicylates (e.g., aspirin (acetylsalicylic acid), diflunisal (dolobid), salicylic acid, salsalate (disalcid), propionic acid derivatives (e.g., ibuprofen, dexibuprofen, naproxen, fenoprofen, ketoprofen, dexketoprofen, flurbiprofen, oxaprozin, loxoprofen), acetic acid derivatives (e.g., indomethacin, tolmetin, sulindac, etodolac, ketorolac, diclofenac, aceclofenac, nabumetone), enolic acid (oxicam) derivatives (e.g., piroxicam, meloxicam, tenoxicam, droxicam, lornoxicam, isoxicam, phenylbutazone), anthranilic acid derivatives (fenamates) (e.g., mefenamic acid, meclofenamic acid, flufenamic acid, tolfenamic acid, selective cox-2 inhibitors (coxibs) (e.g., celecoxib, rofecoxib, valdecoxib, parecoxib, lumiracoxib, etoricoxib, firocoxib, sulfonanilides, nimesulide), clonixin, and licofelone.

In certain embodiments, one or more of the therapeutic agents is a steroid. In certain embodiments, one or more of the therapeutic agents is a corticosteroid. Examples of corticosteroids include, but are not limited to, hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide, prednicarbate, flunisolide, fluticasone furoate, fluticasone propionate, triamcinolone acetonide, beclomethasone dipropionate, and budesonide.

In certain embodiments, the particle comprises an antibiotic. In certain embodiments, the particle comprises ofloxacin. In certain embodiments, the particle comprises an NSAID. In certain embodiments, the particle comprises ibuprofen. In certain embodiments, the particle comprises a corticosteroid. In certain embodiments, the particle comprises dexamethasone. In certain embodiments, the particle comprises two or more therapeutic agents. In certain embodiments, the particle comprises three or more therapeutic agents. In certain embodiments, the particle comprises a steroid, an antibiotic, and an NSAID. In a particular embodiment, the particle comprises dexamethasone, ofloxacin, and ibuprofen. In certain embodiments, one or more therapeutic agents are covalently linked to a triblock bottlebrush copolymer described herein.

In certain embodiments, one or more of the therapeutic agents is an anti-proliferative agent. In certain embodiments, one or more of the therapeutic agents is an anti-cancer agent. In certain embodiments, one or more of the therapeutic agents is a chemotherapeutic agent. Examples of anti-proliferative (e.g., anti-cancer, chemotherapeutic agents) are provided herein.

The triblock bottlebrush copolymers described herein, and the particles described herein, can self-assemble to form hydrogels. Therefore, in another aspect, the present invention provides hydrogels comprising a triblock bottlebrush copolymer described herein. The present invention also provides hydrogels comprising particles described herein (e.g., drug-loaded particles discussed above). The term "hydrogel" refers to a three-dimensional, hydrophilic polymer network which can absorb water or other fluids. A three-dimensional network forms in a hydrogel via the cross-linking of polymer chains through one or more interactions selected from ionic bonding, covalent bonding, hydrogen bonding, and van der Waals interactions. The porous structure of hydrogels can be tuned by controlling crosslinking density. Due to the hydrophilicity of hydrogels, they are highly absorbent and are capable of containing over 90% water. Hydrogels can be responsive to external stimuli (e.g., pH, temperature, or concentration of an analyte) and can undergo reversible solution-gel phase transitions (i.e., change phase) or volume phase transitions (i.e., change in volume or shape) in response to such stimuli.

In certain embodiments, a hydrogel described herein is "thermally responsive," meaning the hydrogel undergoes a phase transition in response to change in temperature. In certain embodiments, a hydrogel described herein undergoes a solution-gel ("sol-gel") phase transition in response to a change in temperature. A "sol-gel phase transition" is an event wherein the hydrogel goes from solution phase (i.e., dissolved in a solvent) to solid phase (i.e., forms a gel, or "gelates"). In certain embodiments, a hydrogel described herein undergoes a sol-gel transition at or around physiological temperature (37° C.). In certain embodiments, a hydrogel described herein undergoes a sol-gel transition between 30° C. and 40° C. For example, a hydrogel described herein may be in solution phase at a temperature below 30° C., but a gel at a temperature above 40° C. In a particular embodiment, a hydrogel described herein may be in solution phase at a temperature below approximately 37° C., but a gel at a temperature above approximately 37° C. Since a hydrogel described herein can gel at a temperature near physiological temperature, hydrogels of the present invention are particularly useful in biomedical applications, including, but not limited to, implants and/or extended-release vehicles for the delivery of therapeutic agents.

As described herein, hydrogels of the present invention can be used as drug delivery systems for the delivery of one or more therapeutic agents. Therefore, a hydrogel provided herein may comprise one or more therapeutic agents. In certain embodiments, a hydrogel described herein comprises one or more therapeutic agents dispersed throughout the hydrogel. In certain embodiments, a triblock bottlebrush copolymer provided herein is conjugated to one or more therapeutic agents to form a complex, and the complex forms a hydrogel described herein.

In certain embodiments, a hydrogel described herein provides extended release of the one or more therapeutic agents. Therefore, a hydrogel of the present invention may comprise one or more therapeutic agents. The therapeutic agents can be any therapeutic agents described herein. For example, in certain embodiments, one or more of the therapeutic agents is selected from the group consisting of antibiotics (e.g., ofloxacin), steroids (e.g., corticosteroids such as dexamethasone), and NSAIDs (e.g., ibuprofen). In certain embodiments, the hydrogel comprises an antibiotic. In certain embodiments, the hydrogel comprises ofloxacin. In certain embodiments, the hydrogel comprises an NSAID. In certain embodiments, the hydrogel comprises ibuprofen. In certain embodiments, the hydrogel comprises a corticosteroid. In certain embodiments, the hydrogel comprises dexamethasone. In certain embodiments, the hydrogel comprises two or more therapeutic agents. In certain embodiments, the hydrogel comprises three or more therapeutic agents. In certain embodiments, the hydrogel comprises a steroid, an antibiotic, and an NSAID. In a particular embodiment, the hydrogel comprises dexamethasone, ofloxacin, and ibuprofen.

A hydrogel of the present invention is useful for the delivery (e.g., extended release delivery) of three or more therapeutic agents to a subject. For example, in a particular embodiment, a hydrogel of the present invention is useful for the delivery (e.g., extended release delivery) of an antibiotic (e.g., ofloxacin), a steroid (e.g., corticosteroids such as dexamethasone), and an NSAIDs (e.g., ibuprofen).

In a particular embodiment, a hydrogel provided herein is a thermally-responsive hydrogel (e.g., gels at or around physiological temperature) comprised of particles described herein, wherein the particles comprise a triblock bottlebrush copolymer described herein, and wherein the particles further comprise (e.g., encapsulate) one or more therapeutic agents (e.g., three or more therapeutic agents). The hydrogel may be comprised of particles encapsulating more than one therapeutic agent per particle; or alternatively, the hydrogel may comprise a mixture of particles encapsulating different therapeutic agents. For example, a hydrogel of the present invention may comprise particles encapsulating an antibiotic (e.g., ofloxacin), particles encapsulating an NSAID (e.g., ibuprofen), and particles encapsulating a steroid (e.g., dexamethasone).

Formulations, Kits, and Administration

In another aspect, the present invention provides formulations comprising the triblock bottlebrush copolymers, particles, and hydrogels described herein. Provided herein are formulations comprising a triblock bottlebrush copolymer described herein, one or more therapeutic agents, and optionally a carrier or excipient. Also provided herein are formulations comprising particles described herein, one or more therapeutic agents, and optionally a carrier or excipient. In another aspect, the present invention provides formulations comprising a hydrogel described herein, one or more therapeutic agents, and optionally a carrier or excipient.

In certain embodiments, the formulation comprises about 1 wt % to about 99% wt % of the triblock bottlebrush copolymer. In certain embodiments, the formulation comprises about 5 wt % to about 90% wt % of the triblock bottlebrush copolymer. In certain embodiments, the formulation comprises about 10 wt % to about 90% wt % of the triblock bottlebrush copolymer. In certain embodiments, the formulation comprises about 20 wt % to about 90% wt % of the triblock bottlebrush copolymer. In certain embodiments, the formulation comprises about 30 wt % to about 90% wt % of the triblock bottlebrush copolymer. In certain embodiments, the formulation comprises about 40 wt % to about 90% wt % of the triblock bottlebrush copolymer. In certain embodiments, the formulation comprises about 50 wt % to about 90% wt % of the triblock bottlebrush copolymer. In certain embodiments, the formulation comprises about 60 wt % to about 90% wt % of the triblock bottlebrush copolymer. In certain embodiments, the formulation comprises about 70 wt % to about 90% wt % of the polymer.

In a particular embodiment, provided herein is a formulation comprising a hydrogel described herein, wherein the hydrogel comprises particles described herein, wherein the particle comprises a triblock bottlebrush copolymer described herein, and wherein the particle comprises (e.g., encapsulates) one or more therapeutic agents. In certain embodiments, the formulation comprises one or more excipients or carries. In certain embodiments, the formulation comprises water.

Formulations described herein can be prepared by any method known in the art of pharmacology or polymer science. In general, such preparatory methods include bringing a triblock bottlebrush copolymer described herein into association with one or more therapeutic agents and a carrier or excipient (e.g., water, DMSO), and/or one or more other accessory ingredients. In certain embodiments, preparation of a formulation described herein comprises a nanoprecipitation step. For example, preparation of a formulation described herein may comprise dissolving one or more therapeutic agents in a solvent (e.g., DMSO, phosphate-buffered saline solution (PBS)), followed by mixing with triblock bottlebrush copolymer dissolved in a solvent (e.g., DMSO), followed by nanoprecipitation. Solvents and excess therapeutic agent can optionally be removed by centrifugal filtration.

The ratio of the amount of a triblock bottlebrush copolymer described herein to the amount of one or more therapeutic agents to be delivered in a described formulation may be adjusted so that the agent may be more efficiently delivered to a subject, tissue, or cell and/or the toxicity of the composition is decreased. In certain embodiments, the ratio of the polymer to the agent(s) is at least about 1:1, at least about 2:1, at least about 5:1, at least about 10:1, at least about 20:1, at least about 50:1, at least about 100:1, at least about 200:1, or at least about 500:1 mol/mol. In certain embodiments, the ratio of the polymer to the agent(s) is less than about 500:1, less than about 200:1, less than about 100:1, less than about 50:1, less than about 20:1, less than about 10:1, less than about 5:1, less than about 2:1, or less than about 1:1 mol/mol. Combinations of the above ranges (e.g., at least about 10:1 and less than about 100:1) are also within the scope of the disclosure.

In certain embodiments, the formulation comprises one therapeutic agent. In certain embodiments, the formulation comprises two or more therapeutic agents. In certain embodiments, the formulation comprises three or more therapeutic agents. The therapeutic agent may be any therapeutic agent known in the art or described herein. For example, a formulation may comprise one or more therapeutic agents selected from antibiotics, steroids, and NSAIDs. In certain embodiments, the formulation comprises an antibiotic, a steroid, and an NSAID. In certain embodiments, the formulation comprises an antibiotic. In certain embodiments, the formulation comprises ofloxacin. In certain embodiments, the formulation comprises an NSAID. In certain embodiments, the formulation comprises ibuprofen. In certain embodiments, the formulation comprises a corticosteroid. In certain embodiments, the formulation comprises dexamethasone. In certain embodiments, the formulation comprises ofloxacin, dexamethasone, and ibuprofen. In certain embodiments, the one or more therapeutic agents are present in the formulation in a therapeutically effective amount. In certain embodiments, the one or more therapeutic agents are present in the formulation in prophylactically effective amounts.

A particle, hydrogel, or formulation described herein comprising one or more therapeutic agents may provide extended release of the one or more therapeutic agents to a subject. In certain embodiments, a particle, hydrogel, or formulation described herein provides extended release of one or more therapeutic agents at physiological temperature. For example, in certain embodiments, a hydrogel or formulation described herein gels upon administration to a subject (e.g., forms a solid or gel) and provides extended release of one or more therapeutic agents to said subject. The extended release of the one or more therapeutic agents may span any time frame. In certain embodiments, the one or more therapeutic agents are released over 1 to 10 days. In certain embodiments, the one or more therapeutic agents are released over more than 10 days. In certain embodiments, the one or more therapeutic agents are released over 1 to 20 days. In certain embodiments, the one or more therapeutic agents are released over more than 20 days. In certain embodiments, the one or more therapeutic agents are released over 1 to 4 months. In certain embodiments, the one or more therapeutic agents are released over 3 to 4 months. In certain embodiments, the one or more therapeutic agents are released over more than 4 months. In certain embodiments, the one or more therapeutic agents are released over more than 6 months. In certain embodiments, the one or more therapeutic agents are released over more than one year.

Particles, hydrogels, and formulations provided herein can be administered by any route, including enteral (e.g., oral), ophthalmic, parenteral, intravenous, intravascular intramuscular, intra-arterial, intramedullary, intrathecal, subcutaneous, intraventricular, transdermal, intradermal, rectal, intravaginal, intraperitoneal, topical (e.g., as ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are ophthalmic administration, oral administration, intravascular administration, intramuscular administration, subcutaneous administration, and/or direct administration to an affected site. In certain embodiments, the formulation described herein is suitable for administration to the eye of a subject.

Pharmaceutically acceptable excipients or carriers used in the formulations include inert solvents, diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the formulations. In certain embodiments, an excipient or carrier is water. In certain embodiments, an excipient or carrier is buffered water. In certain embodiments, an excipient or carrier is saline. In certain embodiments, an excipient or carrier is buffered saline. In certain embodiments, an excipient or carrier is phosphate buffered saline (PBS). In certain embodiments, the excipient or carrier is DMSO.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof. In certain embodiments, phosphate buffered saline (PBS) is used in a formulation described herein.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid forms for oral and parenteral administration include pharmaceutically acceptable solvents, emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In certain embodiments, an acceptable vehicle is phosphate-buffered saline (PBS). In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Suitable devices for use in delivering formulations described herein intradermally include short needle devices. Intradermal formulations can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

A formulation can be prepared, packaged, and/or sold in bulk, as a single unit dose, and/or as a plurality of single unit doses. A "unit dose" is a discrete amount of the formulation comprising a predetermined amount of therapeutic agent(s). The amount of the therapeutic agent is generally equal to the dosage of the therapeutic agent which would be administered to a subject and/or a convenient fraction of such a dosage, such as one-half or one-third of such a dosage.

Relative amounts of the triblock bottlebrush copolymer, the particles, the hydrogels, the one or more therapeutic agents, the excipients or carriers, and/or any additional ingredients in a formulation described herein will vary, depending upon the identity, size, and/or condition of the subject treated and further depending upon the route by which the composition is to be administered.

Solid dosage forms for oral administration include capsules, tablets, pills, powders, and granules. In such solid dosage forms, the particle or hydrogel is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A formulation described herein can be prepared, packaged, and/or sold in a formulation suitable for pulmonary administration via the buccal cavity. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. The propellant may further comprise additional ingredients such as a liquid non-ionic and/or solid anionic surfactant and/or a solid diluent.

Formulations described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the particle or hydrogel, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate.

Formulations described herein as being useful for pulmonary delivery are useful for intranasal delivery. Such a formulation is administered by rapid inhalation through the nasal passage from a container held close to the nares. A formulation described herein can be prepared, packaged, and/or sold in a formulation for buccal administration.

A formulation described herein can be prepared, packaged, and/or sold in a formulation for ophthalmic administration. Such formulations may, for example, be in the form of eye drops including, for example, a solution and/or suspension of the particle or hydrogel; optionally in an aqueous or oily liquid carrier or excipient. Such drops may further comprise buffering agents, salts, and/or one or more other of the additional ingredients described herein. A formulation for ophthalmic administration may also be in the form of a liquid or gel or injection and/or implantation into the eye. Ear drops are also contemplated as being within the scope of this disclosure.

Although the descriptions of the formulations provided herein are principally directed to pharmaceutical compositions which are suitable for administration to humans, it will be understood by the skilled artisan that such compositions are generally suitable for administration to animals of all sorts. Modification of formulations suitable for administration to humans in order to render the compositions suitable for administration to various animals is well understood, and the ordinarily skilled veterinary pharmacologist can design and/or perform such modification with ordinary experimentation.

Formulations provided herein are typically formulated for ease of administration and uniformity of dosage. It will be understood, however, that the total usage of the formulations described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of a therapeutic agent required to achieve an effective amount will vary from subject to subject, depending, for example, on species, age, and general condition of a subject, severity of the side effects or disorder, identity of the particular compound, mode of administration, and the like. An effective amount may be included in a single dose or multiple doses. In certain embodiments, when multiple doses are administered to a subject or applied to a tissue or cell, any two doses of the multiple doses include different or substantially the same amounts of a therapeutic agent described herein. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a therapeutic agent described herein. In certain embodiments, a dose described herein includes independently between 1 mg and 3 mg, inclusive, of a therapeutic agent described herein. In certain embodiments, a dose described herein includes independently between 3 mg and 10 mg, inclusive, of a therapeutic agent described herein. In certain embodiments, a dose described herein includes independently between 10 mg and 30 mg, inclusive, of a therapeutic agent described herein. In certain embodiments, a dose described herein includes independently between 30 mg and 100 mg, inclusive, of a therapeutic agent described herein.

Dose ranges as described herein provide guidance for the administration of a provided formulation to an adult. The amount to be administered to, for example, a child or an adolescent can be determined by a medical practitioner or person skilled in the art and can be lower or the same as that administered to an adult.

A formulation, as described herein, can be administered in combination with one or more additional pharmaceutical agents (e.g., therapeutically and/or prophylactically active agents). The formulations can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The formulation can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the formulation described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

Also encompassed by the disclosure are kits (e.g., pharmaceutical packs). The kits provided may comprise a triblock bottlebrush copolymer, particle, hydrogel, or formulation described herein, and a container (e.g., a vial, ampule, bottle, syringe, and/or dispenser package, or other suitable container). In certain embodiments, the kit comprises one or more therapeutic agents described herein. In some embodiments, provided kits may optionally further include a second container comprising a pharmaceutical excipient for dilution or suspension of a triblock bottlebrush copolymer, particle, hydrogel, or formulation described herein. In certain embodiments, the kits are useful for treating a disease or condition (e.g., ocular condition, diabetic condition, proliferative disease such as cancer) in a subject in need thereof. In certain embodiments, the kits are useful for preventing a disease or condition in a subject in need thereof.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease or condition (e.g., ocular condition, diabetic condition, proliferative disease such as cancer) in a subject in need thereof. In certain embodiments, the kits and instructions provide for preventing a disease or condition in a subject in need thereof. A kit described herein may include one or more additional pharmaceutical agents described herein as a separate composition or formulation.

Methods of Treatment and Use

The present invention provides methods for treating and/or preventing a disease or condition in a subject in need thereof. The methods of treatment and/or prevention described herein comprise administering to the subject a particle, hydrogel, or formulation described herein. In certain embodiments, the disease or conditions is an ophthalmic condition, genetic disease, proliferative disease (e.g., cancer), a disease associated with angiogenesis, a neoplasm, inflammatory disease, autoimmune disease, liver disease, spleen disease, pulmonary disease, hematological disease, neurological disease, painful condition, psychiatric disorder, or metabolic disorder (e.g., diabetic condition).

In certain embodiments, the disease is an ocular condition. Examples of ocular conditions include, but are not limited to, glaucoma, ocular cancer (e.g., retinoblastoma), age-related macular degeneration (AMD), cataracts, diabetic eye disease, dry eye, or a condition associated with ocular surgery. A formulation described herein may be administered to a subject to aid in post-surgical healing after ocular surgery.

Provided herein is a method of treating an ocular condition in a subject in need thereof, the method comprising administering to the subject a formulation described herein to the eye of the subject. In certain embodiments, the formulation comprises one or more therapeutic agents (e.g., steroids (e.g., corticosteroid such as dexamethasone), antibiotics (e.g., ofloxacin), NSAIDs (e.g., ibuprofen)) for extended release to the eye of the subject. In certain embodiments, a formulation comprising a steroid (e.g., dexamethasone), an antibiotic (e.g., ofloxacin), and an NSAID (e.g., ibuprofen) is administered to the eye of a subject to achieve extended release of the three therapeutic agents to the eye of a subject.

In certain embodiments, the disease is a proliferative disease (e.g., cancer). In certain embodiments, the disease is cancer. In certain embodiments, a formulation described herein comprises one or more anti-proliferative (e.g., anti-cancer) agents and is administered to a subject for extended release of said anti-proliferative agents to the subject. Examples of anti-proliferative agents are described herein. Certain anti-cancer agents include, but are not limited to, paclitaxel, gemcitabine, SN-38, and resiquimod. In certain embodiments, local and/or extended release of certain therapeutic agents may reduce inflammation in a subject relative to traditional modes of administration.

In certain embodiments, the disease is a metabolic disease (e.g., a diabetic condition). In certain embodiments, the disease is a diabetic condition. In certain embodiments, the disease is a diabetes (e.g., Type I or Type II diabetes). In certain embodiments, a formulation described herein comprises insulin and is administered to a subject in need thereof for extended release of the insulin. The insulin may be native (e.g., wild-type) insulin or a variant thereof.

The present invention provides methods for extended release of one or more therapeutic agents, the methods comprising administering a particle, hydrogel, or formulation described herein to a subject in need thereof. Extended release of one or more therapeutic agents may confer improved therapeutic efficacy or patient compliance when compared with instant release (e.g., non-extended release) dosing methods for the same therapeutic agents. The extended release formulations described herein may reduce the number of periodic administration events. For example, an injectable formulation with extended release properties described herein may reduce the number of periodic injections necessary to fully treat a disease or condition in a subject (e.g., reduce to one). In certain embodiments, administration of an extended release formulation described herein eliminates the need for surgery. The extended release of the one or more therapeutic agents by a particle, hydrogel, or formulation described herein may span any time frame. In certain embodiments, the one or more therapeutic agents are released over 1 to 10 days. In certain embodiments, the one or more therapeutic agents are released over more than 10 days. In certain embodiments, the one or more therapeutic agents are released over 1 to 20 days. In certain embodiments, the one or more therapeutic agents are released over more than 20 days. In certain embodiments, the one or more therapeutic agents are released over 1 to 4 months. In certain embodiments, the one or more therapeutic agents are released over 3 to 4 months. In certain embodiments, the one or more therapeutic agents are released over more than 4 months. In certain embodiments, the one or more therapeutic agents are released over more than 6 months. In certain embodiments, the one or more therapeutic agents are released over more than one year.

Also provided herein are uses of triblock bottlebrush copolymers, particles, hydrogels, and/or formulations described herein for the treatment and/or prevention of a disease or condition in a subject in need thereof. For example, the invention provides uses of triblock bottlebrush copolymers, particles, hydrogels, and/or formulations described herein in the manufacture of a medicament for treating a disease or condition in a subject in need thereof.

In certain embodiments, the methods described herein comprise administering to a subject a formulation comprising a therapeutically effective amount of one or more therapeutic agents. A "therapeutically effective amount" of a therapeutic agent described herein is an amount sufficient to provide a therapeutic benefit in the treatment of a condition or to delay or minimize one or more symptoms associated with the condition. A therapeutically effective amount means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, for example, a therapeutically effective amount is an amount sufficient for treating an ocular condition.

In certain embodiments, the methods described herein comprise administering to a subject a formulation comprising a prophylactically effective amount of one or more therapeutic agents. A "prophylactically effective amount" of a therapeutic agent described herein is an amount sufficient to prevent a condition, or one or more symptoms associated with the condition or prevent its recurrence. A prophylactically effective amount means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, for example, a prophylactically effective amount is an amount sufficient for preventing a condition after ocular surgery (e.g., infection).

In certain embodiments, a subject described herein is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

A triblock bottlebrush copolymer described herein may be useful in biomedical applications other than drug delivery. For instance, a triblock bottlebrush copolymer, particle, or hydrogel of the present invention may be useful as a material (e.g., an injectable implant) for tissue or cartilage repair, cosmetic implantation, and lubrication or hydration of tissues or biological membranes. A triblock bottlebrush copolymer, particle, or hydrogel described herein may also be useful in non-biomedical applications such as photonics (e.g., photonic crystals), functional materials, chromatography media, stimuli-responsive materials, lubricants, nanolithography, films, and coatings.

EXAMPLES

These and other aspects of the present invention will be further appreciated upon consideration of the following Examples, which are intended to illustrate certain particular embodiments of the invention but are not intended to limit its scope, as defined by the claims.

Thermoresponsive ABC Bottlebrush Copolymer Amphiphiles

Figure 2:
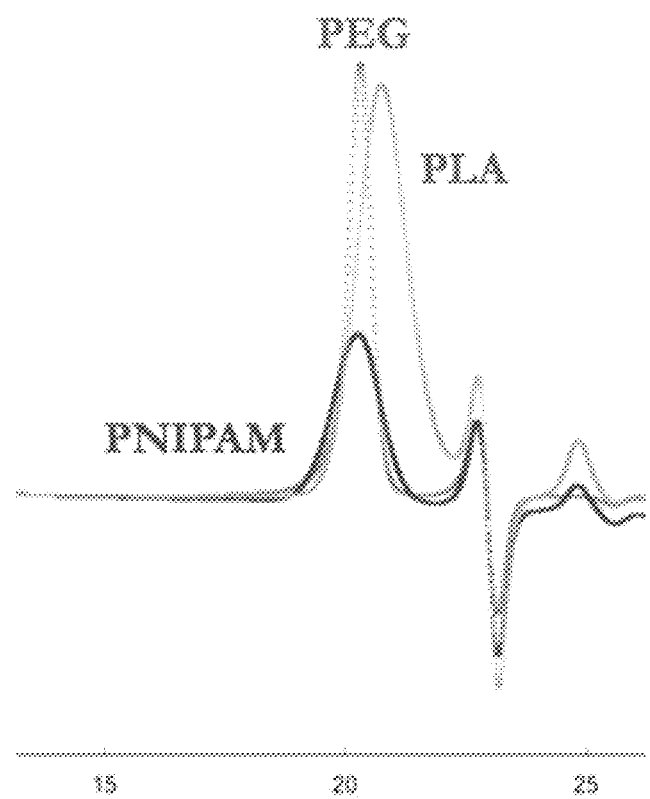
FIG. 2 shows gel permeation chromatography (GPC) characterization of norbornene macromonomers.
Figure 3:
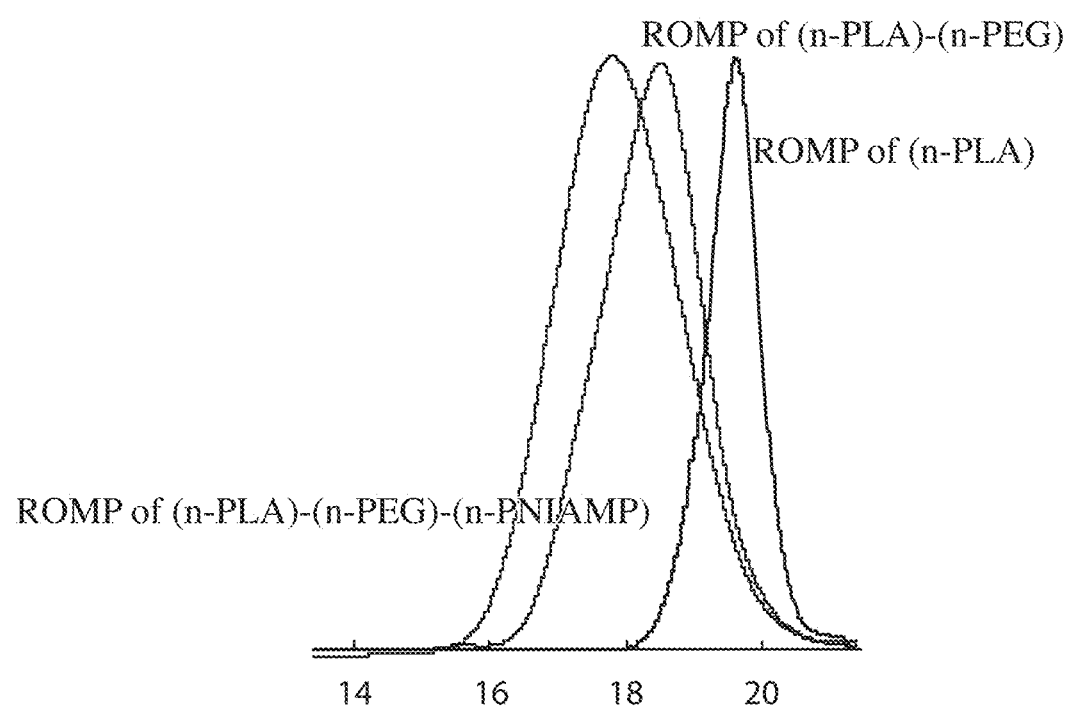
FIG. 3 shows sequential ring-opening metathesis polymerization (ROMP) of PLA macromonomers (DP=10) and PEG macromonomers (DP=40) and PNIPAM macromonomers (DP=10).

The ABC bottlebrush copolymers exemplified are amphiphiles constructed from a hydrophobic segment of polylactic acid, PLA, and hydrophilic segment made of polyethylene oxide, PEG, followed by PNIPAM. At ambient temperature, the bottlebrush copolymers self-assemble into well-controlled micelles. It is documented that backbone rigidity of the bottle-brush amphiphiles allows for imperfect space filling in hydrophobic PLA microdomain. The micelles formed from such amphiphiles can therefore make encapsulation of hydrophobic molecules (i.e., drugs) more favorable thus increasing loading capacity and improving the thermodynamic stability of the micelles at the same time. See, e.g., FIGS. 1-3.

Furthermore, the bottlebrush architecture is uniquely positioned for realizing thermoresponsive amphiphiles because bottlebrush copolymers adapt into a fully extended conformation due to their high grafting density. Introduction of a PNIPAM segment at the periphery of amphiphiles promotes aggregation among micelles upon heating of the medium above lower critical solution temperature (LCST). The rigid backbone of bottlebrushes prevent PNIPAM segment from internal collapse thus promoting efficient formation of PNIPAM microdomains that act as physical crosslinks. The physical crosslinking leads to formation of a micellular networks—a hydrogel.

Lastly, bottlebrush amphiphiles offer yet another important advantage over commonly used linear counterparts. Linear multiblock copolymers are difficult to synthesize. Thanks to advent of ring opening metathesis polymerization (ROMP) (see, e.g., FIGS. 17A-17C, as well as the synthetic procedures below) it is now possible to synthesize elaborate multiblock bottle-brush copolymers. Living nature of ROMP allows for sequential introduction of monomers. By tuning the monomer feed ratios, the size of each block can be controlled to confer desired properties of resulting micelles such as morphology, size, and drug loading drug loading capacity.

Synthesis of Triblock Bottlebrush Copolymers

General Methods and Instruments

All reagents and solvents were purchased from Sigma Aldrich or VWR and used as supplied unless otherwise noted. Analytical high-performance liquid chromatography mass spectrometry (LC/MS) data were obtained using an Agilent 1260 series HPLC system equipped with a variable wavelength ultraviolet-visible (UV-Vis) detector and an Agilent 6130 single quadrupole mass spectrometer. Separation was achieved using an Agilent Zorbox SB-C18 rapid resolution HT column with mobile phase gradients of 0.1% acetic acid in water and acetonitrile. Experiments were performed at room temperature with a flow rate of 1.0 mL/min. Gel permeation chromatography (GPC) was performed using two Shodex KD-806M GPC columns connected in series with a DAWN EOS 18 angle laser light scattering (MALLS) detector (Wyatt Technology) and a T-rEX refractive index detector (Wyatt Technology). Experiments were performed at 60° C. using 0.2 M LiBr in N,N-dimethylformamide (DMF) eluent at a flow rate of 1 mL/min. Nuclear magnetic resonance (NMR) experiments were performed on Bruker AVANCE-400 NMR spectrometer. MestReNova NMR 8.1.2-11880 software was used to analyze the NMR spectra.

Synthesis of Norbornene-N-Hydroxysuccinimidyl (NHS)-Ester

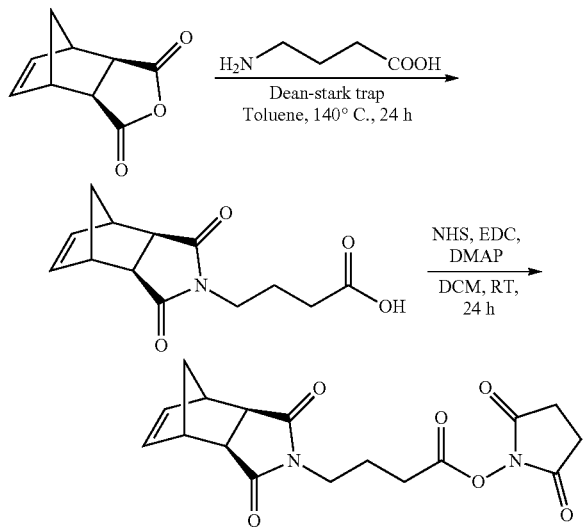

An anhydrous toluene solution (60 ml) containing aminobutyric acid (2.0 g, 12.2 mmol) and cis-5-norbornene-exo-2,3-dicarboxylic anhydride (1,320 mg, 12.8 mmol) was prepared in 100 ml round-bottom flask (attached with a Dean-Stark trap). Following 24 h reaction at 140° C. under oil bath, the reaction solution was transferred for purification by sequential extraction with 1 M HCl and brine. Note that the organic phase was collected and further subjected magnesium sulfate dehydration and filtration. The ultimate product of norbornene-butyric acid was obtained as a faint white solid by rotary evaporation.

Furthermore, the product of norbornene-butyric acid together with N-(3-dimethylaminopropyl)-N'-ethylcarbodiimide hydrochloride (EDC, 1.86 g, 9.0 mmol), 4-(dimethylamino)pyridine (DMAP, 72 mg, 0.6 mmol) was dissolved in anhydrous dichloromethane (100 ml). The reaction solution was kept stirring for 30 min, followed by addition of anhydrous dichloromethane (DCM) solution (10 ml) containing N-hydroxysuccinimide (1.03 g, 9 mmol) for 24 h reaction at room temperature. The product of norbornene-N-hydroxysuccinimidyl (NHS)-ester was purified by silica gel column chromatography ($V_{EtOAc}:V_{hexanes}=1:1$) (780 mg, 38%) as a white-solid.

Synthesis of Norbornene-PEG Macromonomer (Nor-PEG)

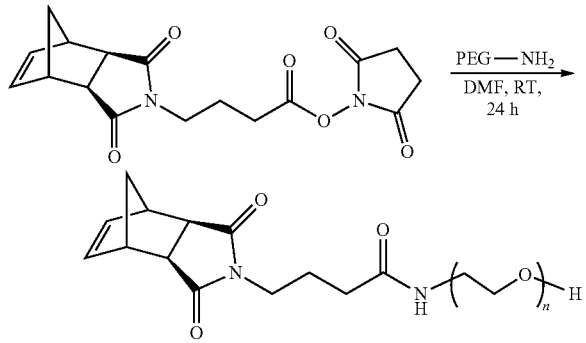

The norbornene-PEG was prepared through coupling reaction of N-Hydroxysuccinimide and amine between amine-terminal functionalized PEG ($M_w$ 3 kDa) and norbornene-N-hydroxysuccinimidyl-ester. Herein, O-(2-aminoethyl)poly(ethylene glycol) (500 mg, 0.17 mmol) and norbornene-N-hydroxysuccinimidyl-ester (60.55 mg, 0.18 mmol) were dissolved in anhydrous (dimethylformamide) DMF (50 mL), followed by overnight reaction under stirring at room temperature. The reaction product was purified by diethyl ether precipitation for 5 times. Ultimately, the product was collected by benzene freeze-drying (350 mg, 65%) and obtained as a white powder.

Synthesis of Norbornene-PNIPAM Macromonomer (Nor-PNIPAM)

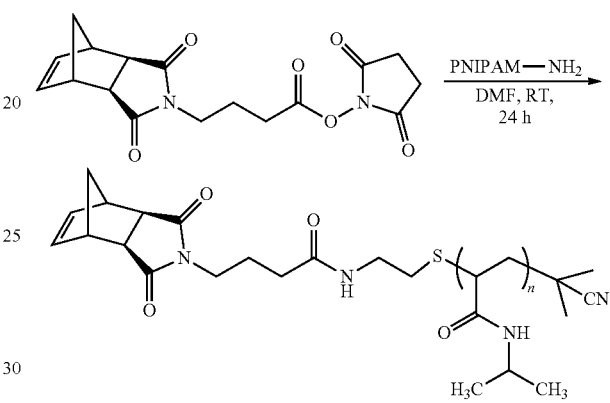

Similar to the synthetic procedure of norbornene-PEG, the norbornene-[poly(N-isopropylacrylamide)] (PNIPAM) was prepared through coupling reaction of N-Hydroxysuccinimide and amine between amine-terminal functionalized PNIPAM (5.5 kDa) and norbornene-N-hydroxysuccinimidyl-ester. Herein, PNIPAM-NH$_2$ (900 mg, 0.16 mmol) and norbornene-N-hydroxysuccinimidyl-ester (60.55 mg, 0.18 mmol) were dissolved in anhydrous DMF (50 mL), followed by overnight reaction under stirring at room temperature. The reaction product was purified by diethyl ether precipitation for 5 times. Ultimately, the product was collected by benzene freeze-drying (590 mg, 65%) and obtained as a white powder.

Synthesis of Norbornene-Propanol

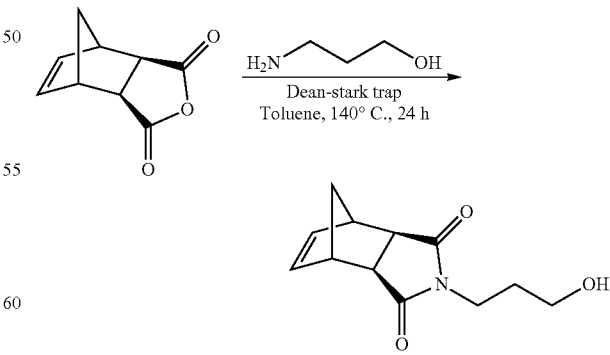

An anhydrous toluene solution (60 ml) containing 3-amino-1-propanol (0.915 g, 0.9 mL, 12.2 mmol) and cis-5-norbornene-exo-2,3-dicarboxylic anhydride (1,320 mg, 12.8 mmol) was prepared in 100 ml round-bottom flask (attached with a Dean-Stark trap). Following 24 h reaction at 140° C. under oil bath, the reaction solution was concentrated by rotary evaporator for silica gel column chromatography ($V_{EtOAc}$:$V_{hexanes}$=1:1) (810 mg, 41%) as a white-solid.

Synthesis of Norbornene-PLA Macromonomer (Nor-PLA)

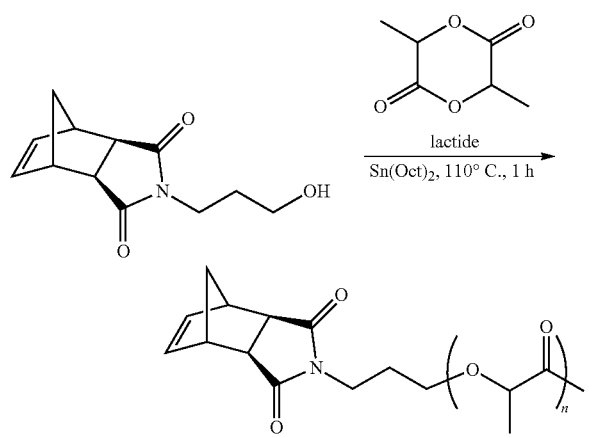

A microwave vial containing anhydrous norbornene-propanol (205 mg, 1 mmol), lactide (5.76 g, 40 mmol) was vacuum dry for 3 h prior to reaction. After refill with nitrogen gas, the microwave vial was transferred for heating and stirred in a microwave reactor (incubation temperature starting from room temperature to 90° C.). By observing the melting into liquid phase, catalyst of Tin(II) 2-ethylhexanoate [$Sn(Oct)_2$] was injected into the reaction mixture under protection of nitrogen. Following 1 h reaction, the reaction was quenched in ice bath. The product was dissolved in DCM (15 ml). The ultimate product was purified by methanol precipitation for 3 times.

Ring-Opening Metathesis (ROMP) Polymerization

In a glovebox, MM of n-PLA was dissolved in THF (0.05 M) in a vial with stir bar. A Grubbs III solution in THF (0.05 M) was prepared in a separate vial. Aliquot of catalyst solution was added into n-PLA solution. The ROMP was allowed to proceed for 1 h. The second MM of n-PEG was placed in a separate vial. The entire reaction solution of first romp was added to second MM. Following another 1 h reaction, the reaction solution was then added to the third MM of n-PNIPAM for 1 h reaction. One drop of ethyl vinyl ether was added to quench each polymerization. The solvent was removed in vacuo, followed by dissolving in DMSO. The solution was dropwise added into $dH_2O$ under vigorous stirring at 4° C. The entire solution was transferred to centrifugal filtration with MWCO 100 kDa under 2,000 RPM for 20 min. The purification process was repeated for 5 times. The ultimate product was obtained by lyophilization.

Figure 17A:
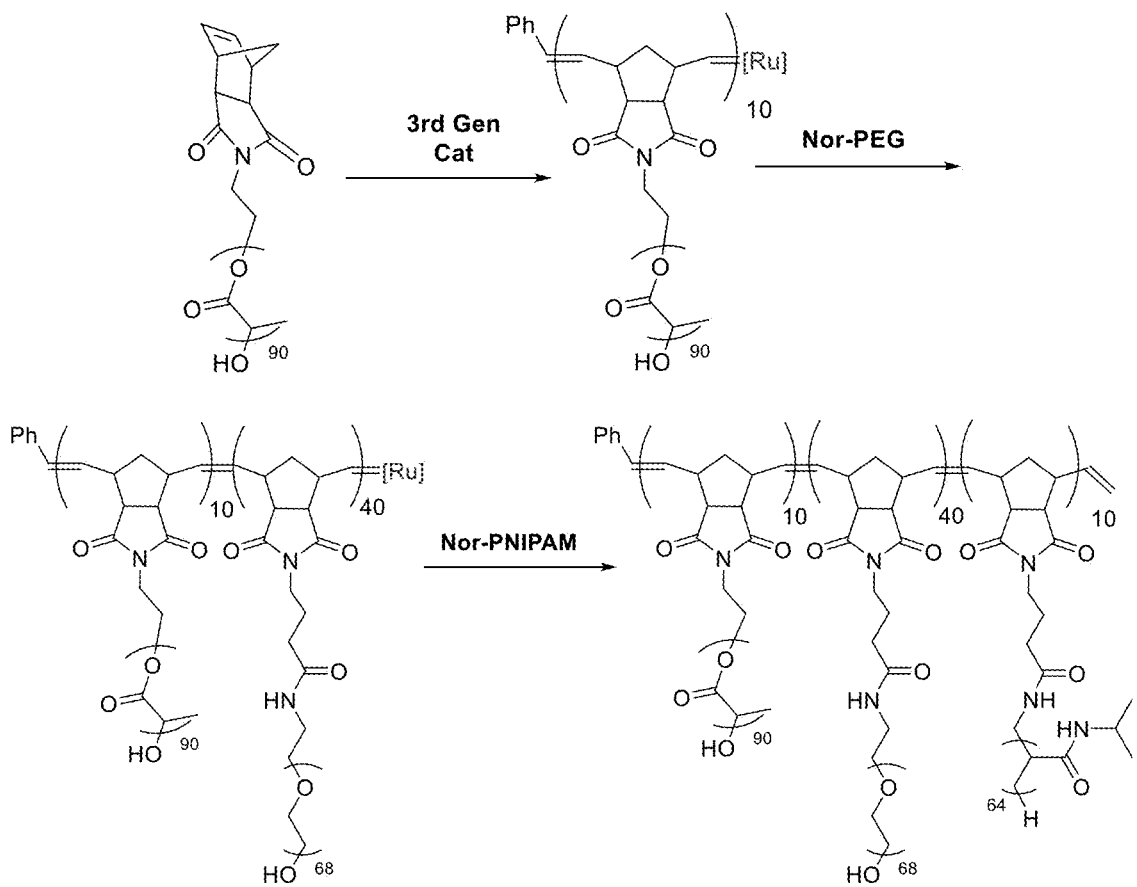
FIGS. 17A-17C show synthesis of bottlebrush ABC copolymers via sequential ring-opening metathesis polymerization (ROMP).
Figure 17B:
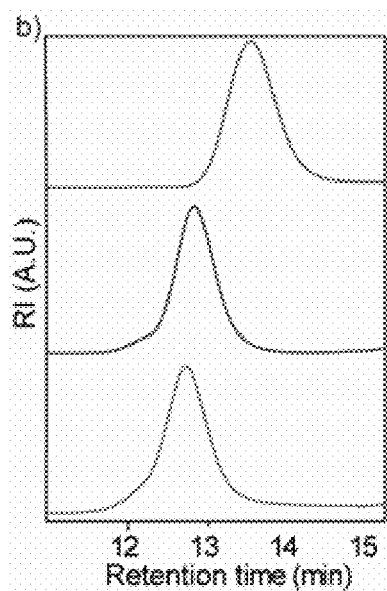
Figure 17C:
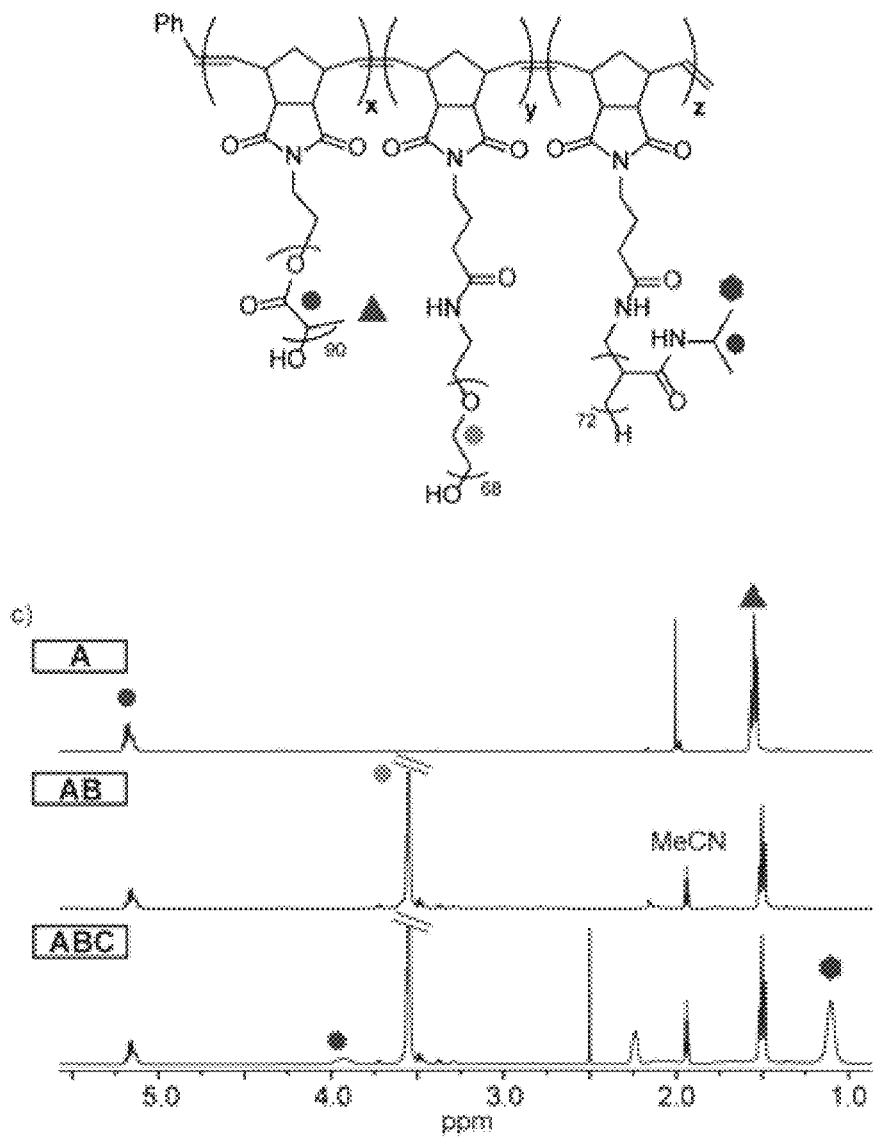
Figure 19A:
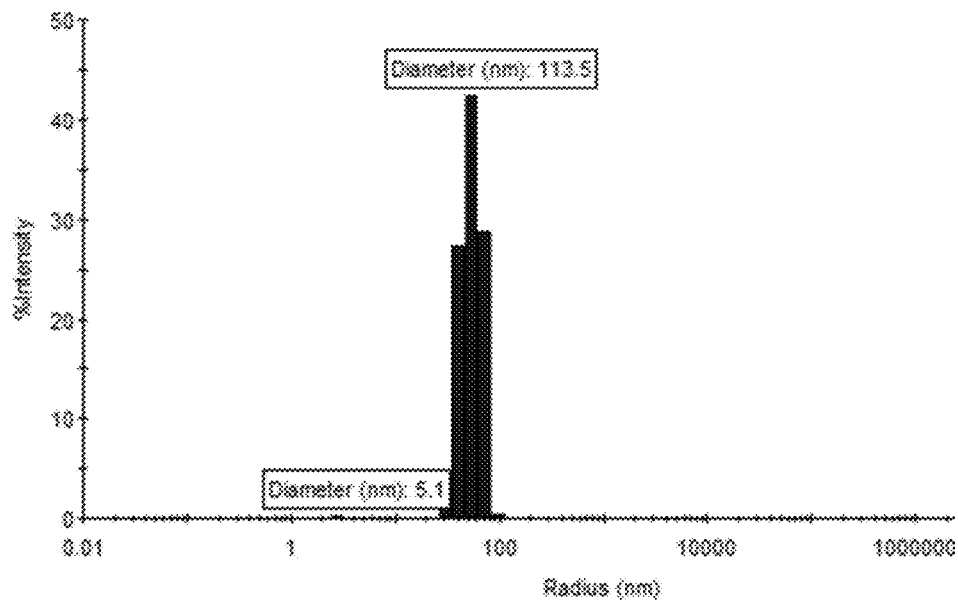
FIG. 19A-19B show that giant amphiphiles assemble into giant micelles. DLS measurement were performed using Wyatt Technology Mobius DLS instrument on 1 mg/mL solutions of bottle-brush copolymers in milli-Q water or PBS. Solutions of samples were filtered through a 0.45 µm Nalgene filter (nylon membrane) into disposable polystyrene cuvettes, which were pre-cleaned with compressed air. Measurements were made in sets of 20 acquisitions, and the average hydrodynamic diameters were calculated using the DLS correlation function via a regularization fitting method (Dynamics 7.4.0.72 software package from Wyatt Technology).
Figure 19B:
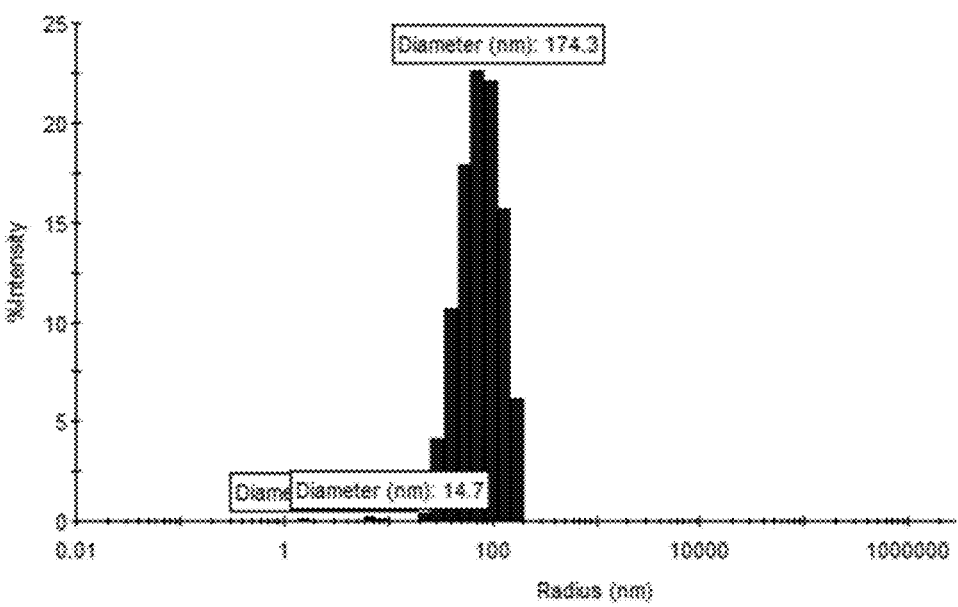
Figure 20:
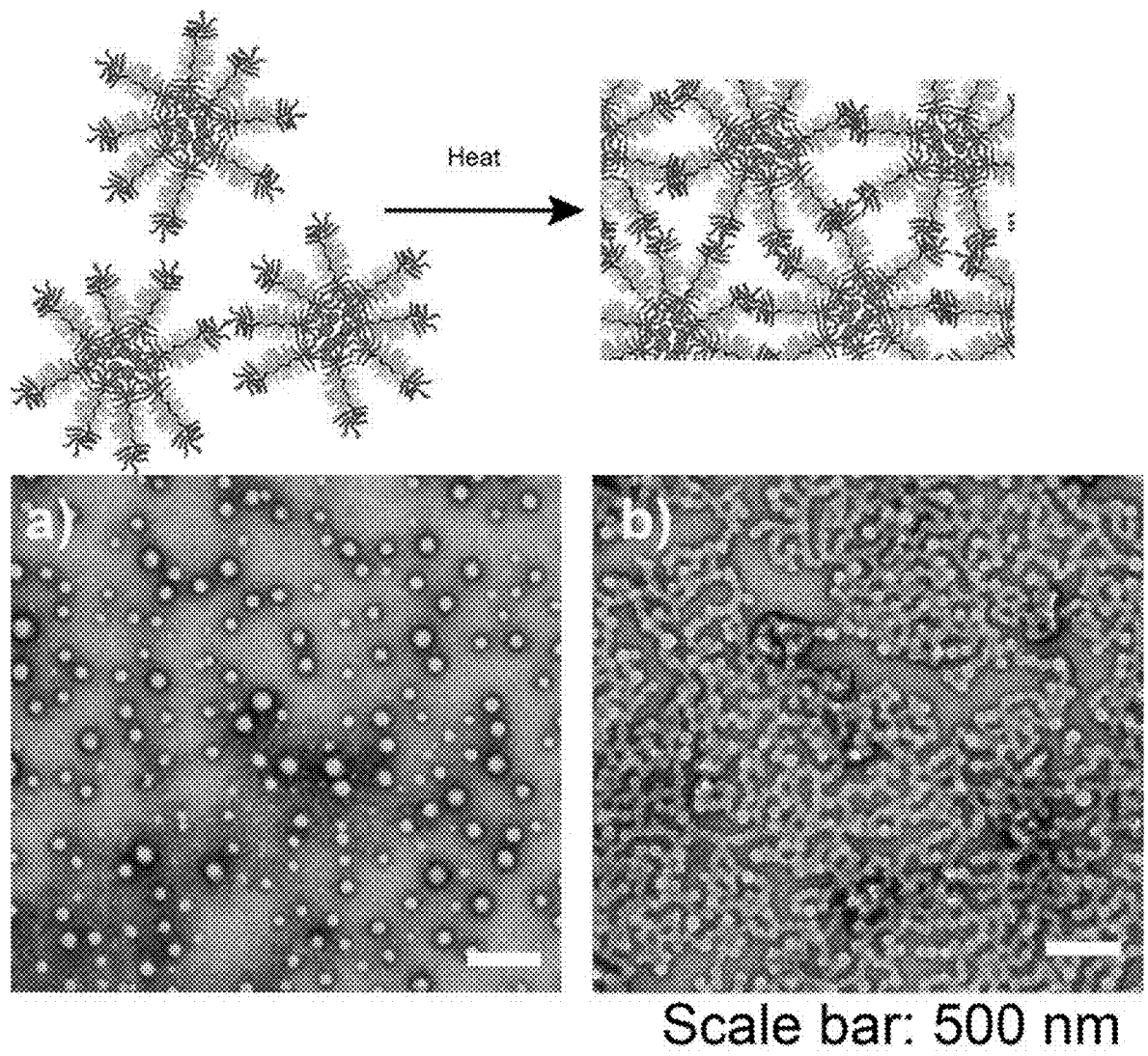
FIG. 20 shows heat-induced physical cross-links at PNIPAM corona. Upon heating a micellular network forms and solution turns into a gel. The solution of ABC copolymer was placed onto TEM grid, subjected to air-dry either at 25° C. or 37° C., then negatively stained with uranyl acetate (4%, Electronic Microscopy Sciences), excess stain was wicked away from the grid and the sample was let to air-dry at appropriate temperature before imaging. TEM images were acquired using a FEI Tecnai Multipurpose TEM (G2 Spirit TWIN, 120 kV).
Figure 21A:
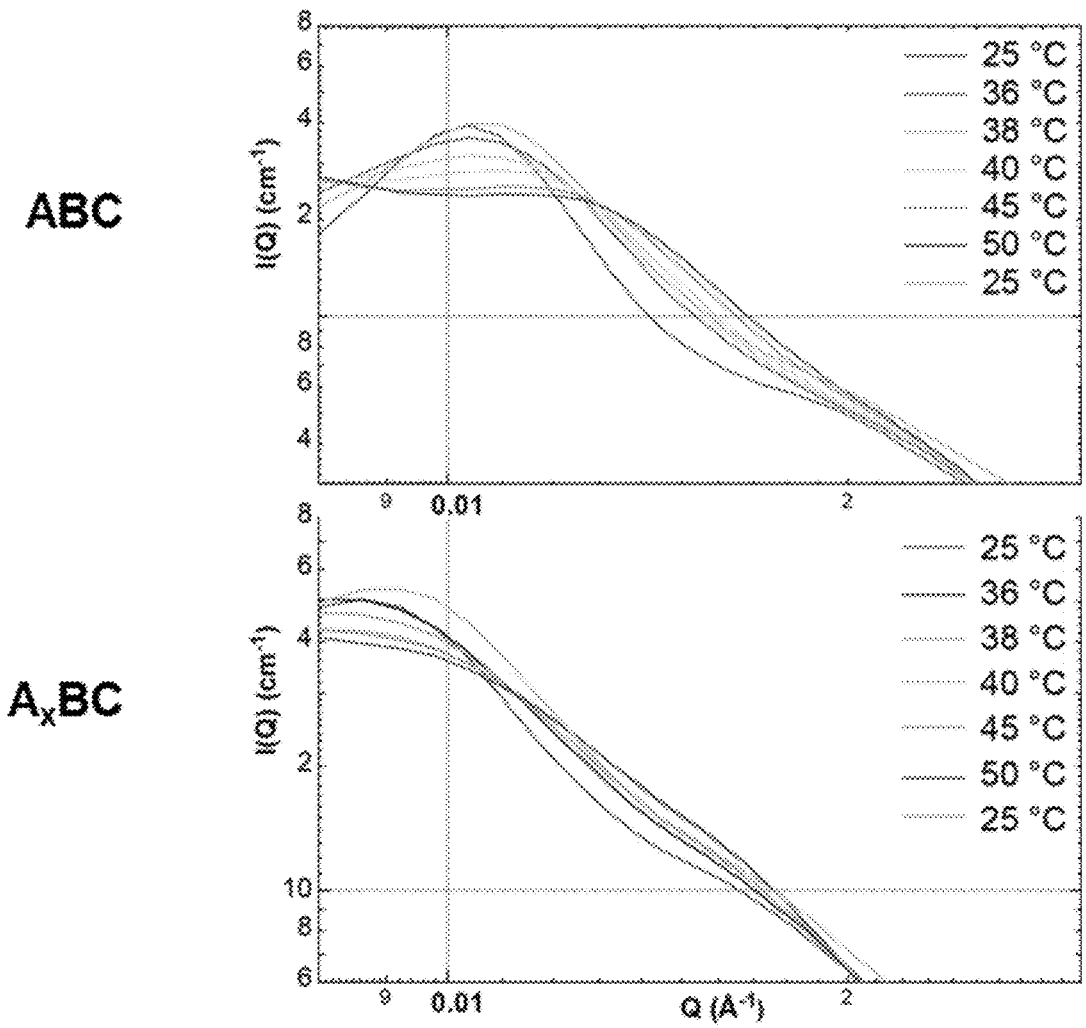
FIG. 21A. Thermoresponsive micelle aggregation—varied temperature Small Angle X-ray Scattering (SAXS). ABC Core-shell model fitting: r(core) ~13 nm; r(shell) ~43 nm. Transmission SAXS was conducted at the 12-ID-B beamline at the Advanced Photon Source of Argonne National Lab. The beamline detector was calibrated with silver behenate. Solution of copolymer (100 mg/mL for ABC and 80 mg/mL for A$_x$BC) was placed into circular washer and Kapton tape was used to seal both sides of the sample. The washer was placed onto a temperature controlled holder. Sample was allowed to equilibrate for 3 min at every temperature point before acquisition.
Figure 21B:
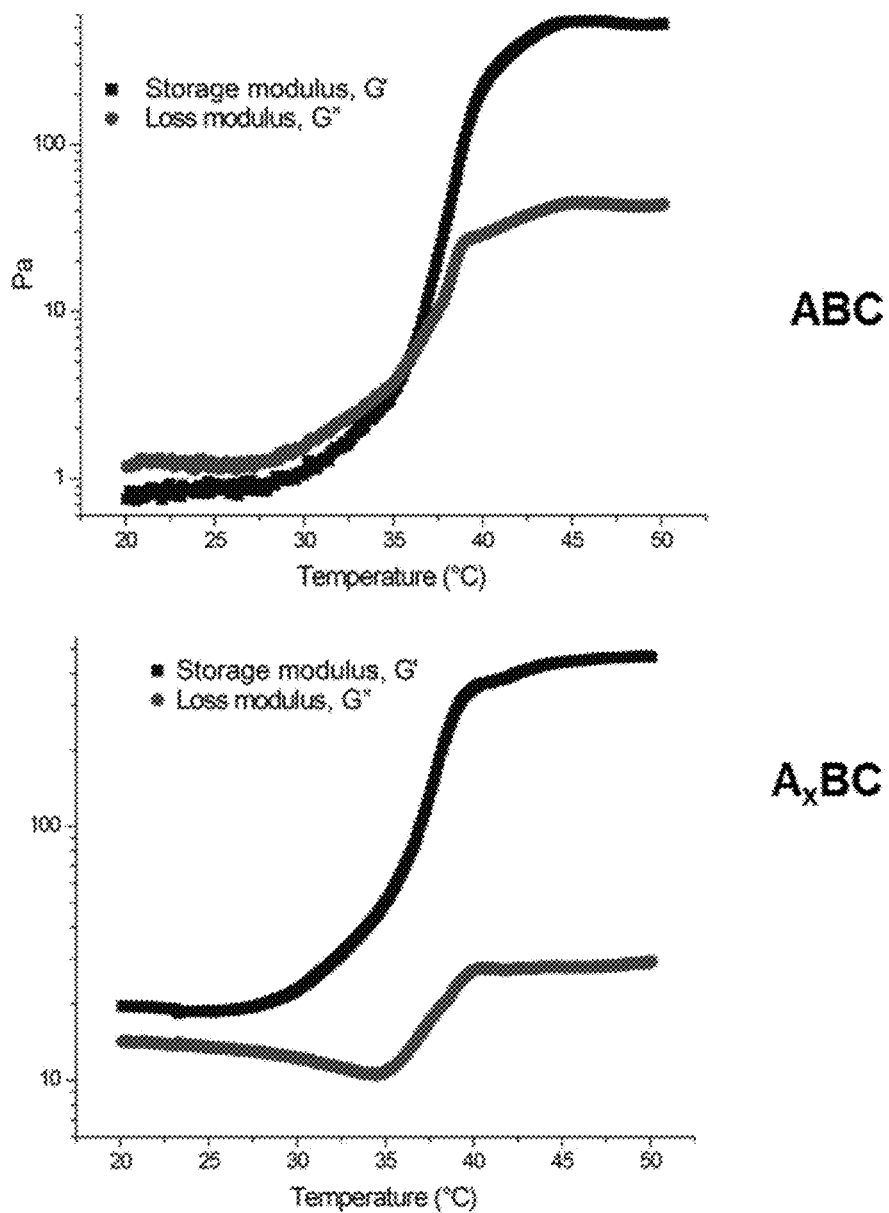
FIG. 21B. Thermoresponsive micelle aggregation—varied temperature dynamic mechanical analysis. Varied temperature rheology experiments were performed on a TA Instruments Discovery Hybrid Rheometer HR-2 rheometer outfitted with an Active Temperature Control (ATC) and environmental enclosure for temperature control. A parallel-plate geometry (radius=20 mm) was used and coupled with a bottom plate, the gap between the two plates containing copolymer solution (100 mg/mL for ABC and 80 mg/mL for A$_x$BC) was set to 800 mm. The temperature sweep experiments were performed at 1 rad/s, 0.5% strain, and at 1° C./min FIG. 22. SAXS data fitted with a core-shell model (Igor Pro). Core-shell model fitting: r(core) ~13 nm; thickness (shell) ~43 nm.
Figure 22:
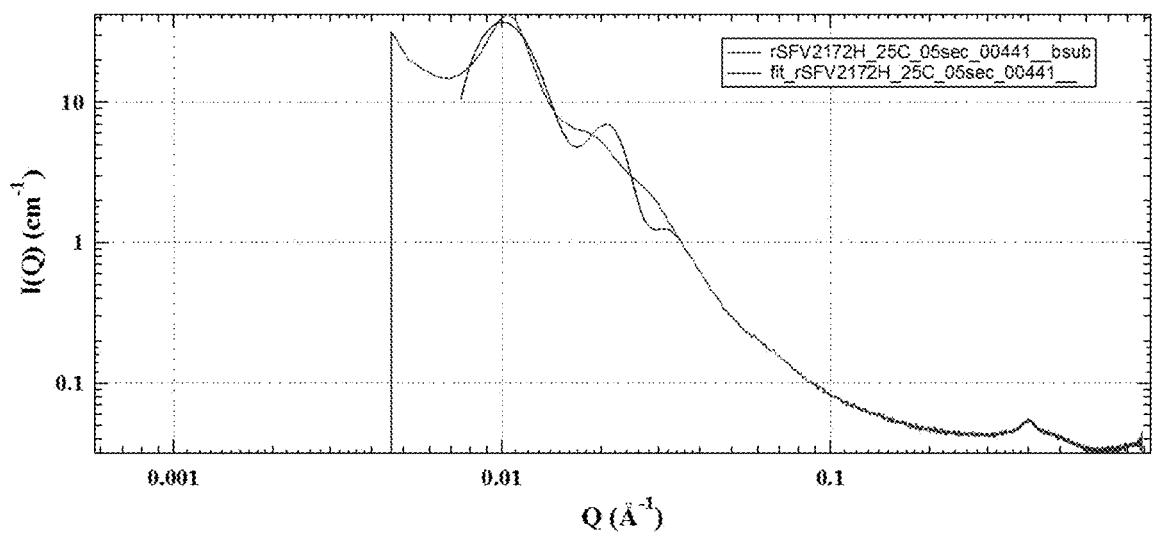
Figure 23:
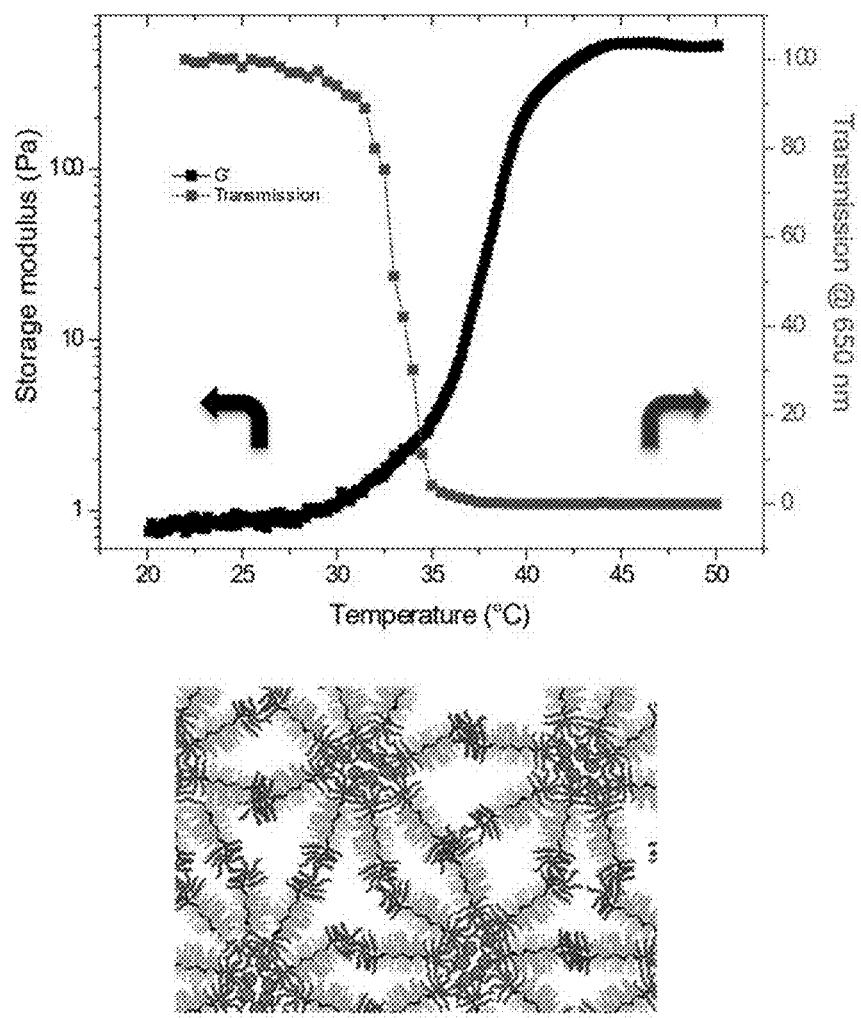
FIG. 23 shows thermoresponsive behavior of particles described herein. Replotted ABC rheology with optical density data.
Figure 24:
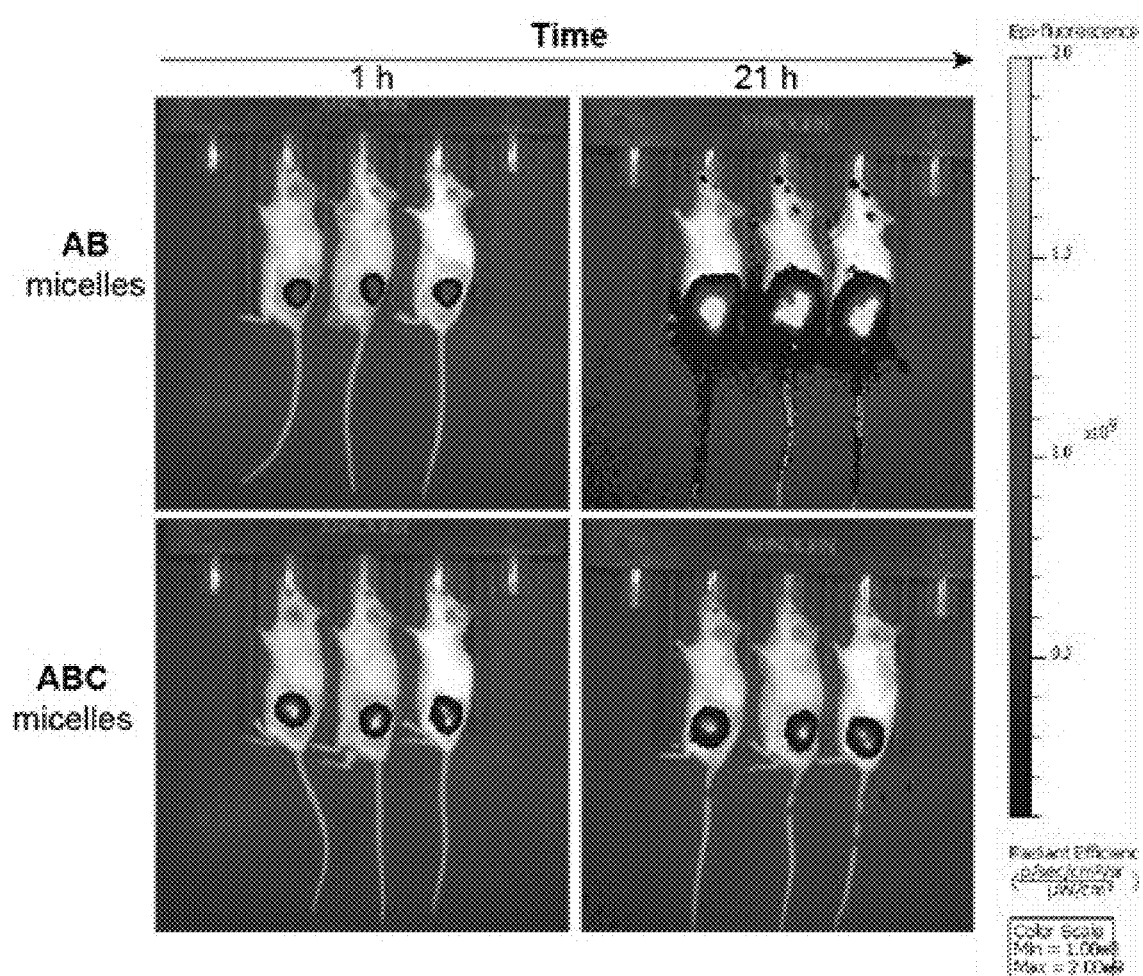
FIG. 24. Local depot formation; ABC vs. AB (Cy$_{7.5}$ label). Diblock and thermoresponsive triblock systems were compared. As a negative control, non-geling AB was used. The AB bottlebrush two-block copolymer forms micelles in water but because it lacks PNIPAM block, it does not undergo gelation. This exemplifies the gel forming capability of the ABC in vivo. Solutions of copolymers (100 mg/mL in PBS) were injected at hind flank of mice (n=3). Mice were imaged using Caliper IVIS Spectrum at 1 hour and 21 hour after injection.

For other synthetic examples, see, e.g., FIGS. 17A-17C.

Drug-Loaded Particle Preparation and Characterization

Preparation of Drug/PLA-PEG-PNIPAM Particles

Figure 4:
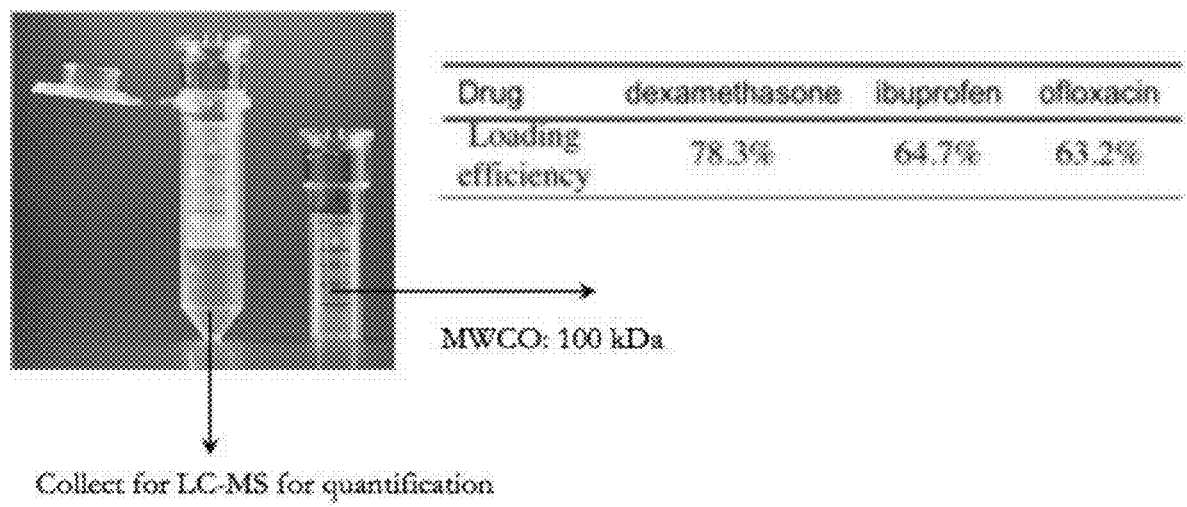
FIG. 4 shows nanoprecipitation for the formation of particles. Drugs dissolved either in DMSO or pH 10 buffer were mixed with polymer in DMSO, followed by nanoprecipitation in PBS (pH 7.4). DMSO and free drugs were removed by centrifugal filtration.

The nanoprecipitation technique was employed for encapsulation of drugs into PLA-PEG PNIPAM formulated particles. Herein, the triblock polymer brush of PLA-PEG-PNIPAM (50 mg) and ibuprofen (50 mg) was separately dissolved in 100 μl DMSO. Then, aliquot of 10 μl ibuprofen solution was added to the entire PLA-PEG-PNIPAM solution, followed by dropwise addition of mixture into aqueous PBS (100 ml. pH 7.4) under vigorous stirring at 25° C. Following 30 min stirring, the samples was transferred to centrifugal filtration with MWCO 100 kDa under 2,000 RPM for 20 min. The filtration process was performed for 5 times by using PBS as elution carrier with aim of completely removal of DMSO. Ultimately, the particle fraction was collected with 3 times PBS washing, which was subjected to evaporation to obtain desirable concentration. The resulted formulation was characterized by DLS measurement. The drug loading efficiency was quantified by LC-MS measurement by comparing the ibuprofen concentration in the filtrate to the total feed ibuprofen. Furthermore, the same procedure of nanoprecipitation was followed to prepare dexamethasone/PLA-PEG-PNIPAM particle. A slightly modified procedure [merely using 100 mM $NaHCO_3$ buffer (pH 10) to dissolve ofloxacin with respect to poor solubility of ofloxacin in DMSO] of nanoprecipitation was utilized to prepare ofloxacin/PLA-PEG-PNIPAM particle. See, e.g., FIG. 4. The solution of each obtained polymeric formulation solution, subjected to air-dry either at 25° C. or 37° C., was transferred to TEM measurement.

Dynamic Light Scattering (DLS) Measurement

Figures 5A, 5B:
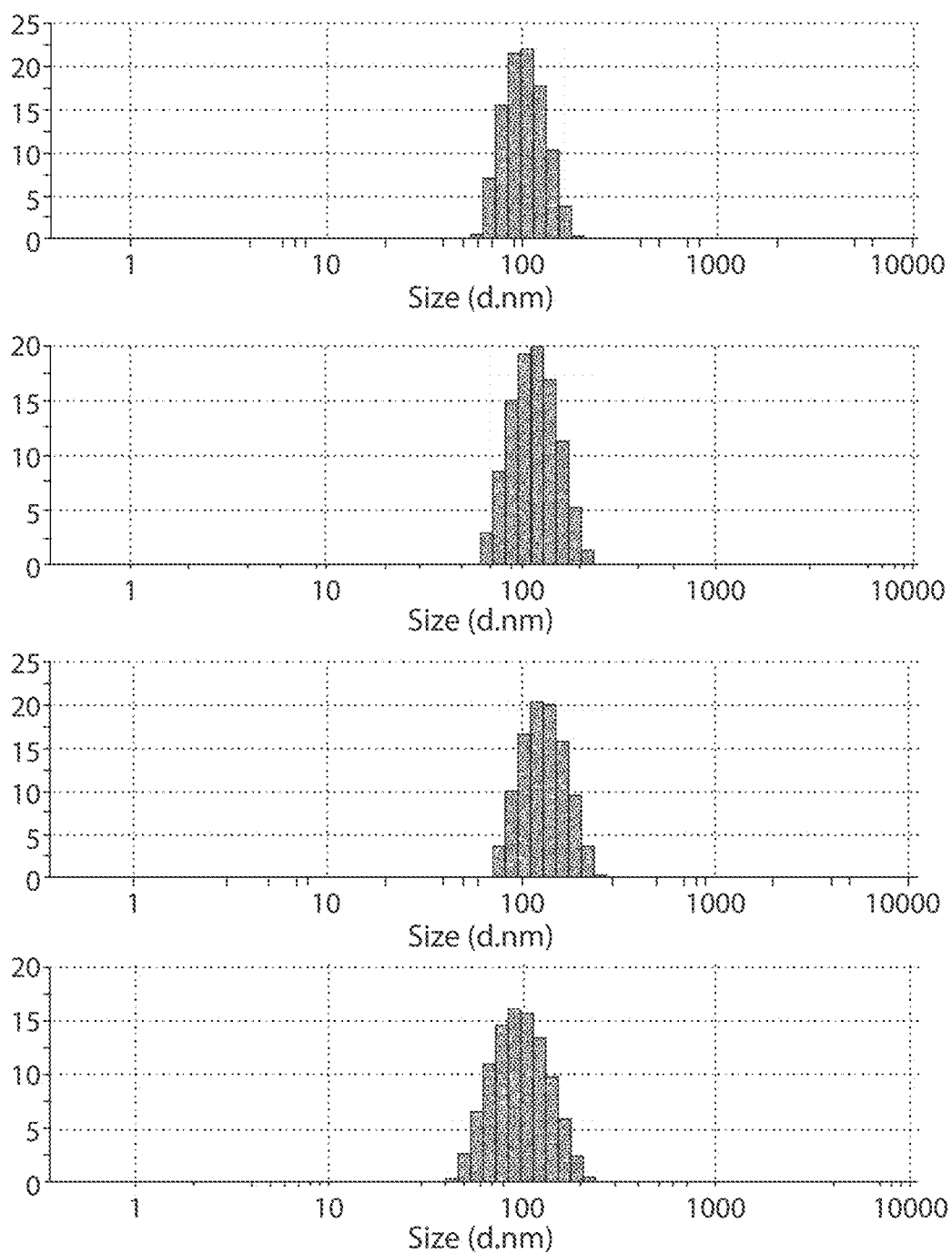
FIGS. 5A and 5B show characterization of particles from self-assembly of polymer brush/drug mixtures.

The size and the polydispersity index (PDI) of diverse formulations, including blank PLA-PEG-PNIPAM formulation, ibuprofen loaded PLA-PEG-PNIPAM formulation, dexamethasone loaded PLA-PEG-PNIPAM formulation and ofloxacin loaded PLA-PEG-PNIPAM formulation at entire PLA-PEG-PNIPAM concentration of 1 mg/ml, were evaluated by DLS using Nano ZS (ZEN3600, Malvern Instruments, Ltd., UK). A He—Ne ion laser (633 nm) was used as the incident beam. Each sample (1 mL) was prepared and analyzed by the cumulant method to obtain the particle Z-average diameter and the PDI. The results were expressed as the mean of three independent measurements. See, e.g., FIGS. 5A-5B.

Gelation

Figure 6:
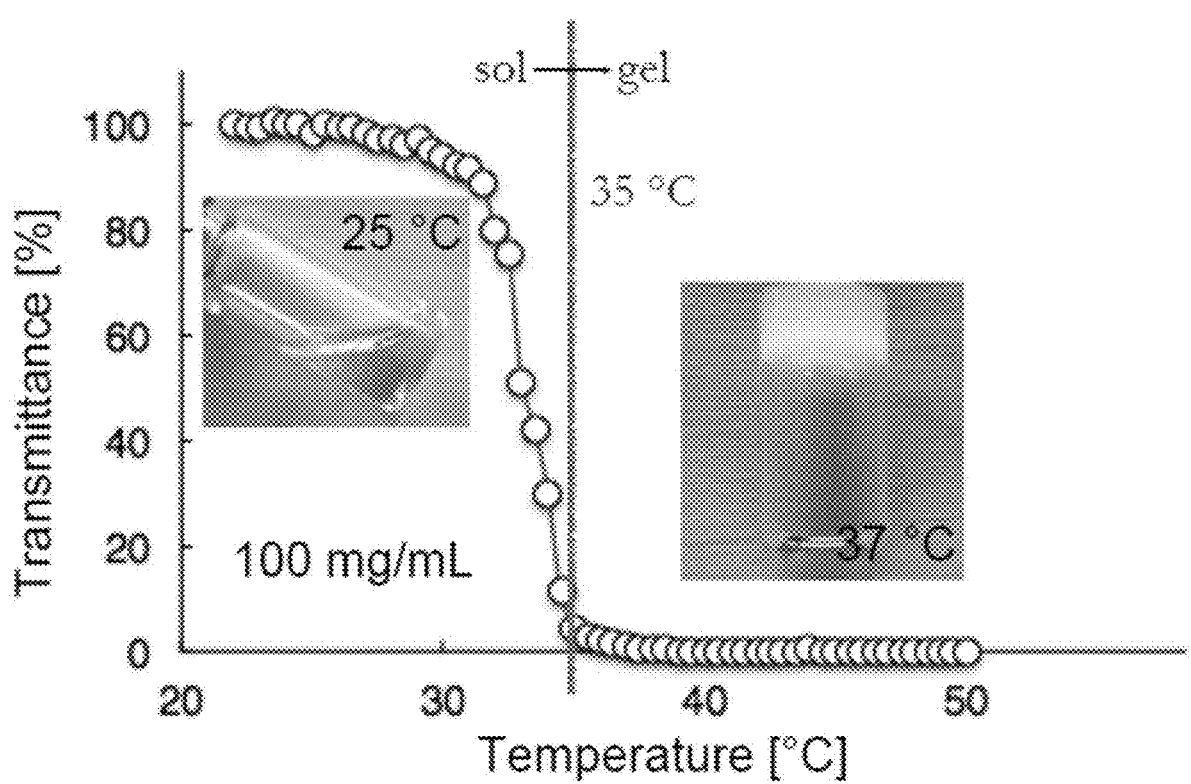
FIG. 6 shows thermal-responsive gelation behavior of the particle hydrogel.
Figure 7:
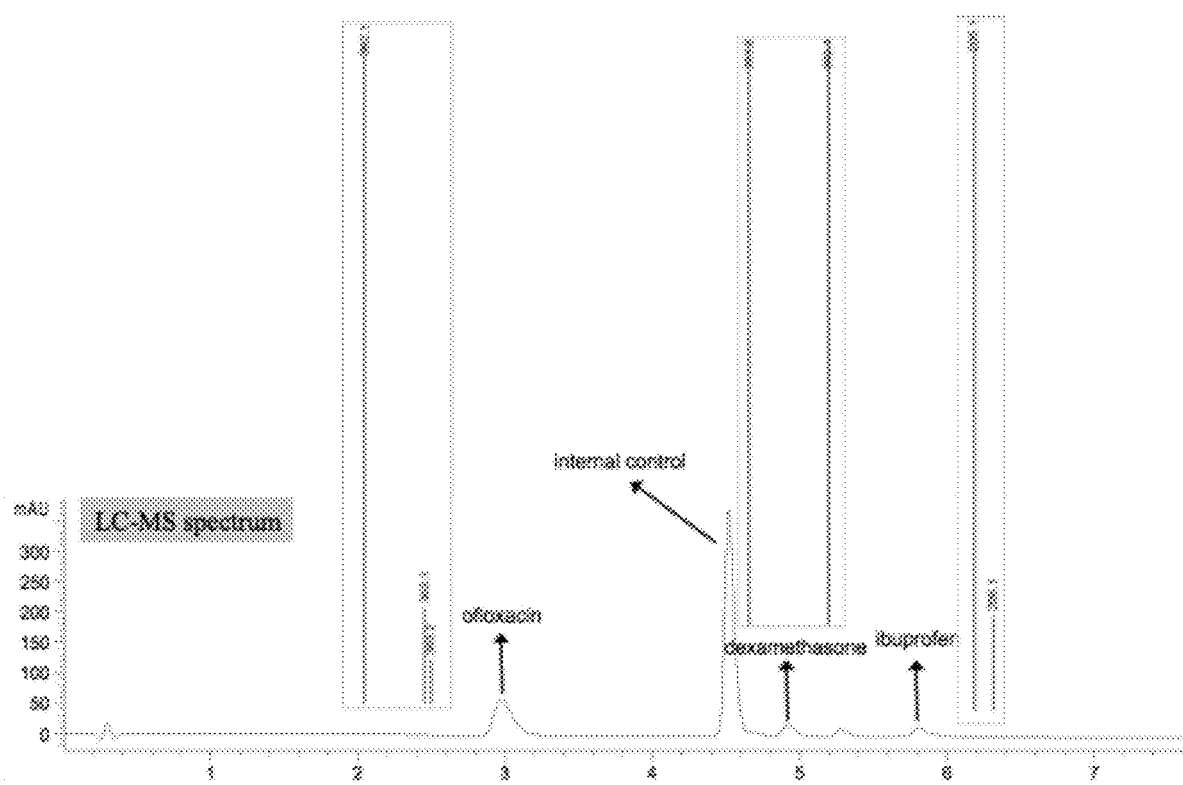
FIG. 7 shows drug quantification (ofloxacin, dexamethasone, and ibuprofen) by liquid chromatography (LC).

The prepared nanoformulations were concentrated to a concentration of 100 mg/ml through centrifugal filtration through MWCO 100 kDa. Then, aliquot of each nanoformulation encapsulated by each drug were mixed at equal volume ratio. See, e.g., FIG. 6.

Drug Releasing Profile

Figure 8:
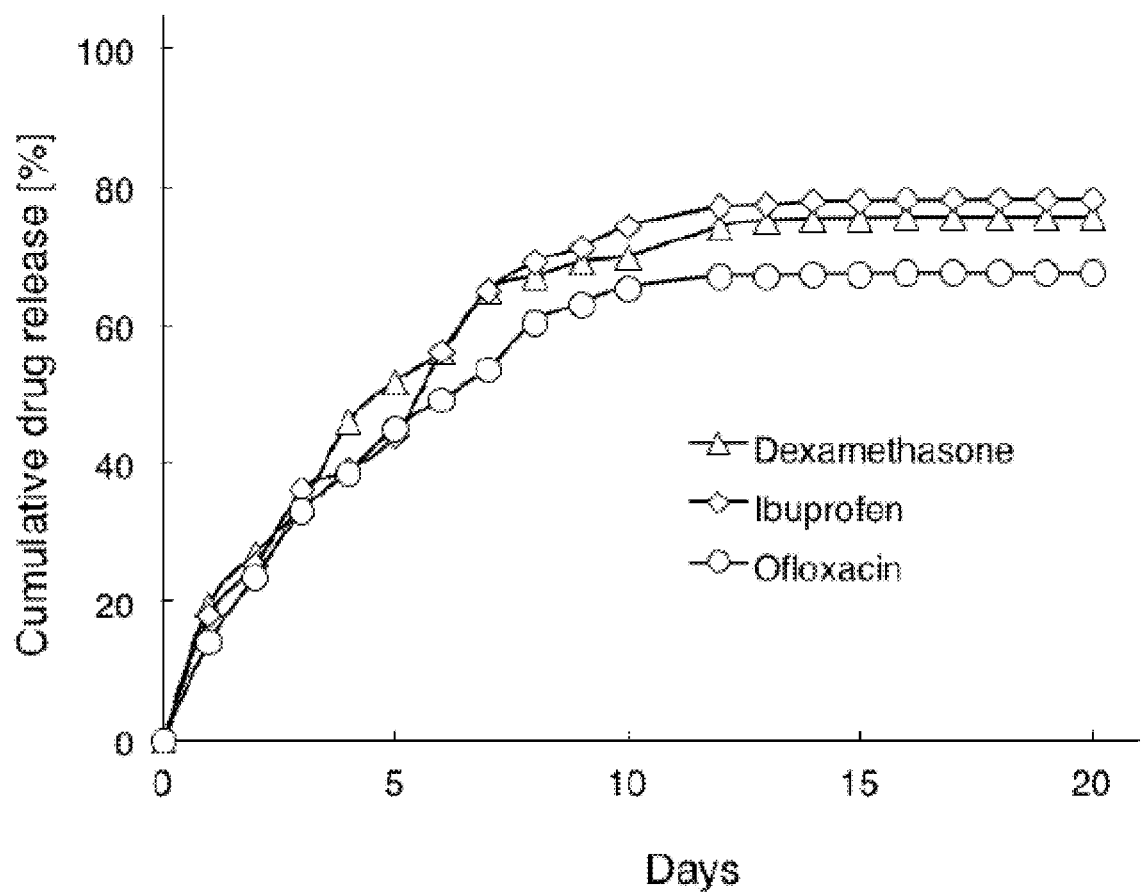
FIG. 8 shows cumulative drug release profiles. Particles containing individual drug were mixed at equal volume, followed by incubation at 37° C. for gelation. Drug release in PBS at 37° C. was quantified by LC-MS.

The mixture of drug-encapsulated polymeric formulation (300 uL) was incubated in 2 mL PBS solution at 37° C. Aliquot of the eluted drug PBS medium (100 uL) was collected every 24 h for LC-MS measurement for quantification of drug release rate. Note, the collected volume was replaced with fresh buffer. See, e.g., FIG. 8.

LDH Assay

Figure 9:
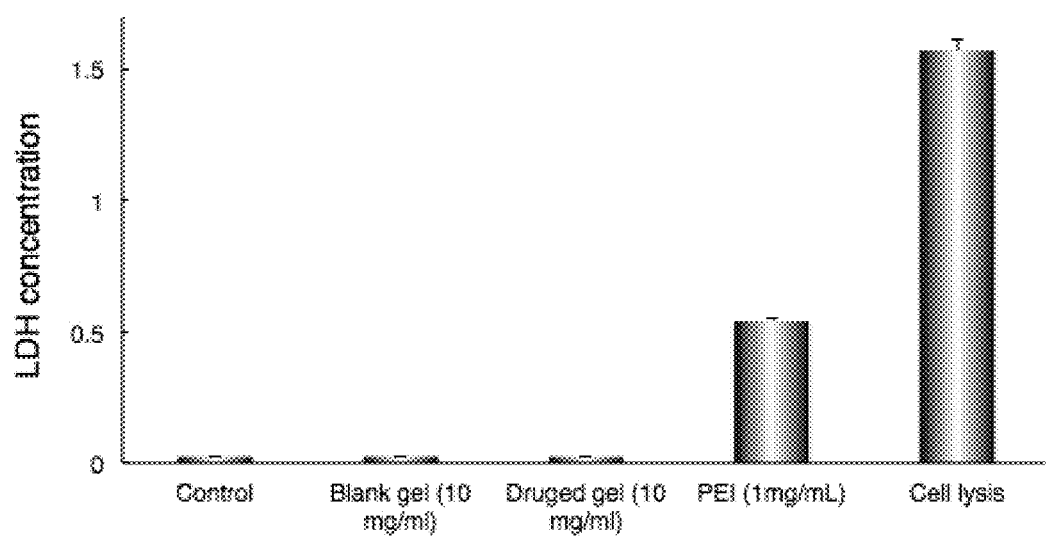
FIG. 9 shows biocompatibility of the particle hydrogel. Samples were added to medium for human umbilical vein endothelial cells (HUVEC), the biocompatibility was evaluated by quantification of LDH in the medium after 48 h incubation.

HUVEC were seeded in 24-well culture plates (20,000 cells/well) and incubated overnight in 400 μL MCDB131 containing 10% FBS and 10 ng/mL b-FGF. The medium was replaced with 400 μL of fresh medium, followed by addition of 30 μL sample h solution in PBS (133.3 mg/ml, 25° C.). After 72 h incubation at 37° C., the biocompatibility of the sample to HUVEC was investigated by quantification of lactate dehydrogenase (LDH) released from the cells according to a LDH assay. As control, cells treated with jetPEI (1 mg/mL) and cell lysis buffer was also investigated. See, e.g., FIG. 9.

Targeted Delivery and Sustained Release of Anti-Cancer Agents

Discovery of highly potent chemotherapeutic drugs for treatment of cancers have saved millions and improved patients' quality of life. While use of a single drug for treatment can in some cases result in emergence of resistance in cancers (adenoma lung, for example), combination therapies targeting dissimilar cellular pathways lead to higher rates of complete remission. However, efficacy of an approved small molecule anticancer medicines and immunomodulators, as well as of the drug candidates currently in clinical development is often restricted by several important limitations. To elicit their therapeutic activity, drug molecules need be in diseased tissue at sufficient concentrations for prolonged periods. Because of their low water solubility and short circulation life-times, many chemotherapeutics, such as SN-38 and PTX, are injected intravenously in repeated fashion, often in conjunction with an encapsulating agent to improve their solubility.

The systemic administration and importantly narrow therapeutic window, are associated with severe side-effects. Similar challenges are surfacing in promising field of immunochemotherapy that augments chemotherapeutics with body's own immune system to fight malignant cells. Antigens produced from cancer cells killed by chemotherapeutic are not processed efficiently by immune cells because of immune-suppressing microenvironment inside the tumors. Immunomodulators such as Resiquimod can stimulate immune cells to process tumor-specific antigens and recruit immune cells into fight against tumor. However, if administered systemically the immune modulators can lead to dramatic side effects collectively described as cytokine storm.

An ideal delivery system enables a single dose administration and maximize concentration of therapeutic at tumor site for prolonged periods, at the same time minimizing unwanted exposure to healthy tissues, thereby reducing serious side-effects. Covalent attachment of drugs via cleavable linkers to macromolecules that take advantage of enhanced permeation and retention effect (EPR) (BASP, Abraxane) or active targeting biomolecules have been shown to be promising delivery platforms that improve therapeutic window. However, in both approaches the vascularization at the tumor site plays an important role for efficient delivery. Conjugates are administered systemically and the cytotoxic drugs are successfully accumulated and released in tumor types with predominantly rich blood supply. An alternative to systemic dosing is use of drug-loaded delivery vehicles that can be directly injected at the tumor site allowing local drug release. Local administration is also desired for ophthalmologic treatments, as described above.

In context of immunotherapy is it has been shown that dosing immunomodulators such as cytokines at concentrations higher than optimal produces undesired effects as initial cytokine storm that can be followed by immune-numbing, where the immune cells become insensitive to activation. Hence, development of such combination therapies requires availability of smart vehicles for drug delivery that can maintain optimal concentrations of chemotherapeutics and immunomodulators to achieve healing effects.

Figure 10:
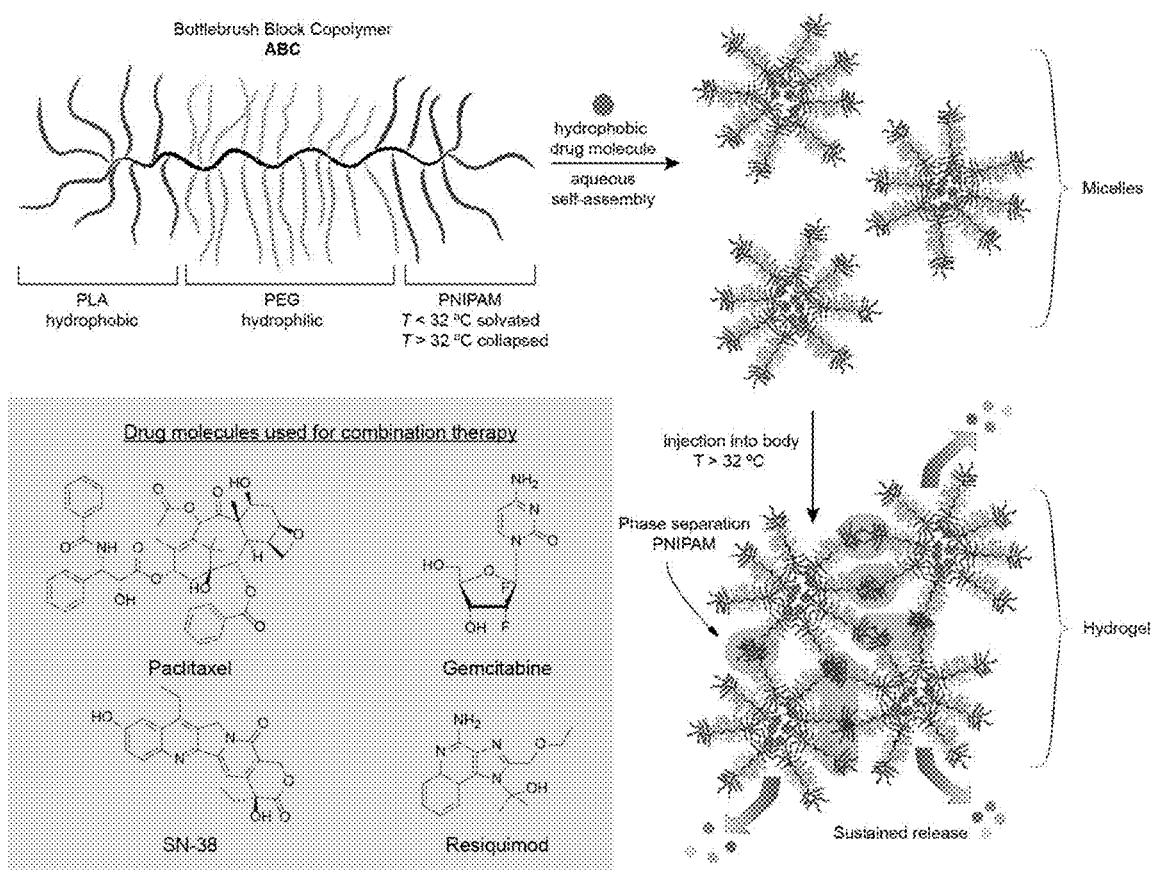
FIG. 10 shows an exemplary ABC bottlebrush copolymer, encapsulation of hydrophobic drug molecules (e.g., anti-proliferative agents), and assembly of the nanoparticles into thermoresponsive hydrogels. Structures of exemplary hydrophobic drug molecules (e.g., anti-proliferative agents) are shown: paclitaxel (PTX), gemcitabine, SN-38, and resiquimod (R848).
Figure 11:
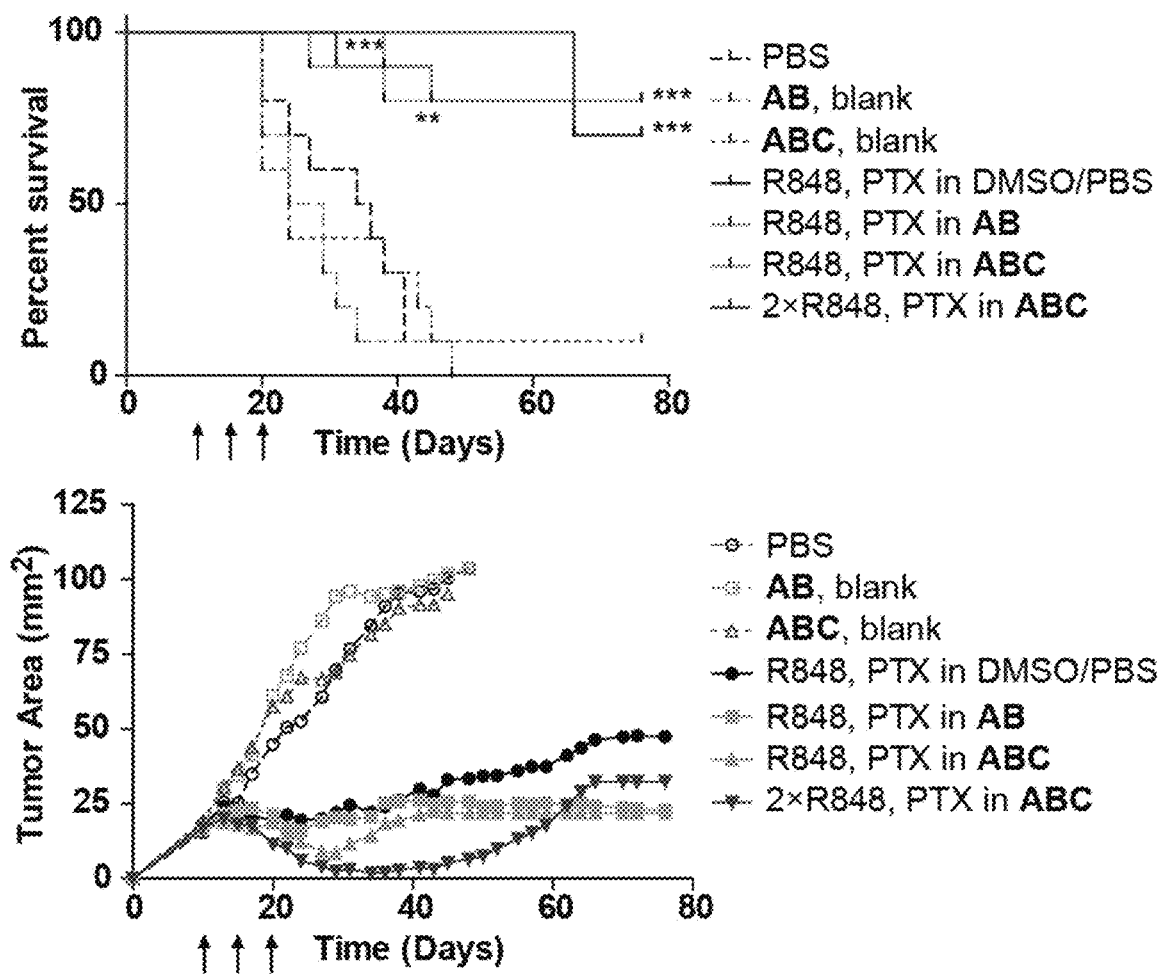
FIG. 11. PTX+R848 hydrogel combo for CT-26 (0.5 M inoc.) tumor treatment. CT-26 is a colon carcinoma cell line. Resiquimod (R848) Low=1.5 mg/kg; High=3 mg/kg; 10 mg/kg of PTX in all treatment groups.
Figure 12:
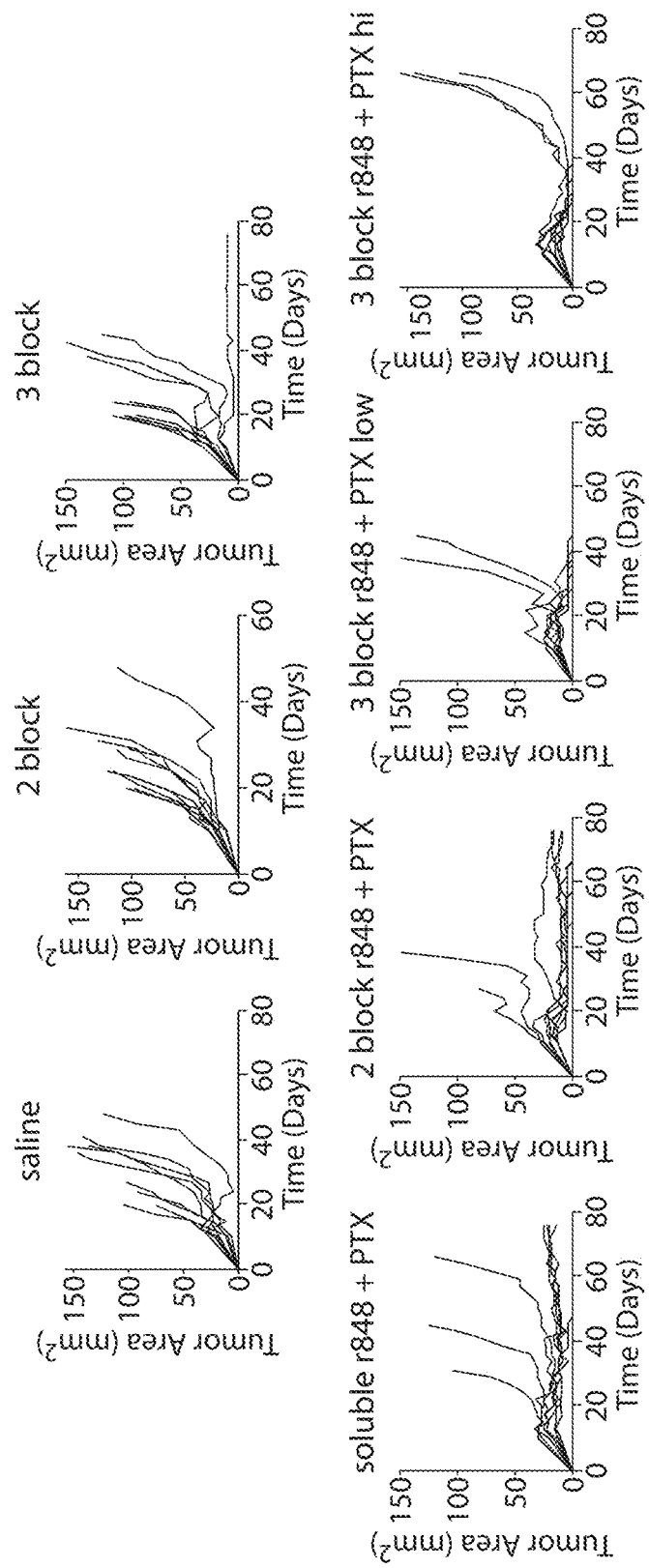
FIG. 12. PTX+R848 hydrogel combo for CT-26 (0.5 M inoc.) tumor treatment. Resiquimod (R848) Low=1.5 mg/kg; High=3 mg/kg.
Figure 13:
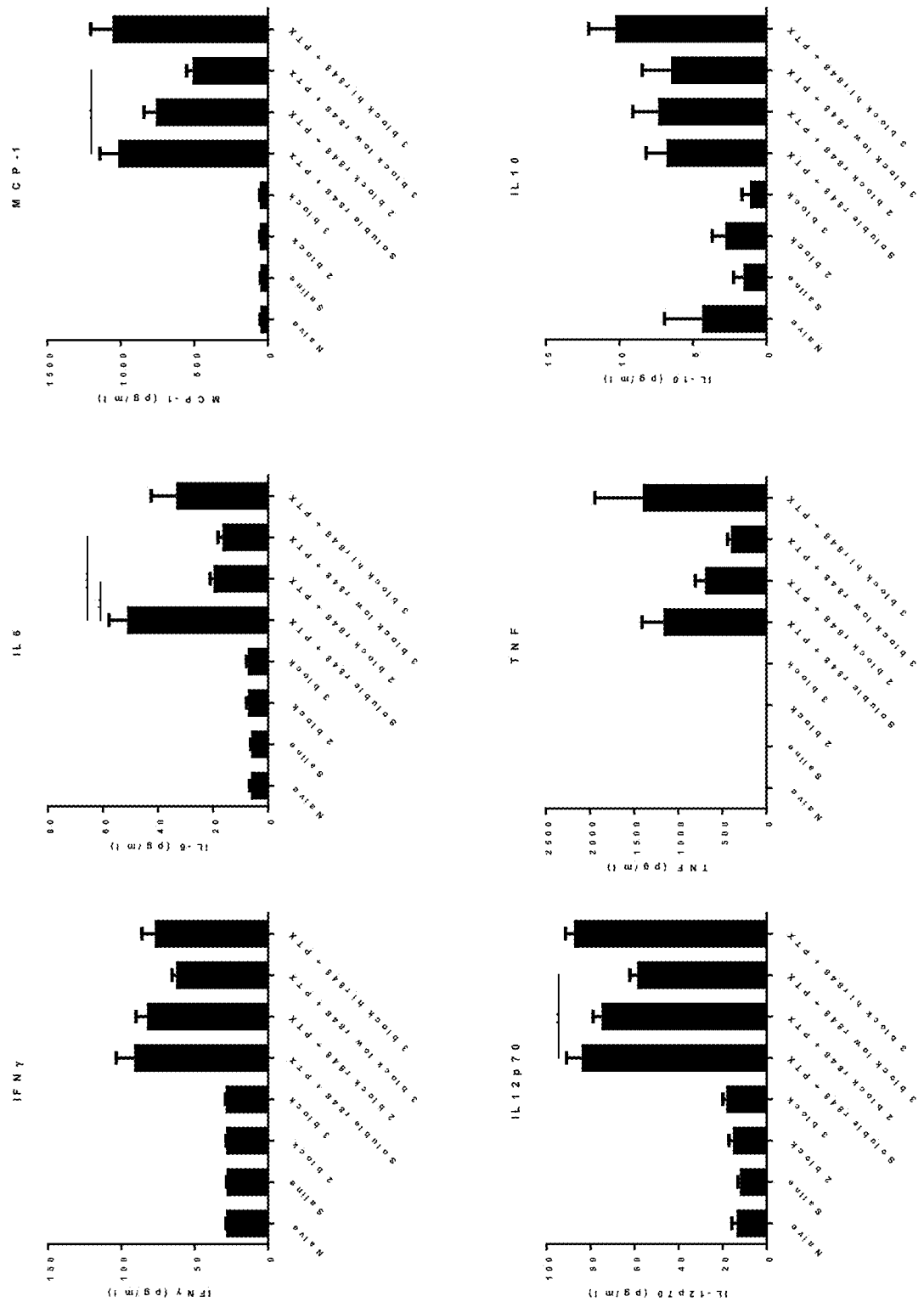
FIG. 13 shows that sustained release reduces systemic inflammation. The serum samples were analyzed by cytometric bead array using the CBA Mouse Inflammation Kit from BD biosciences to quantitatively measure protein levels of IL-6, IL-10, MCP-1, IFN-g, TNF, and IL-12p70 following manufacturer's instructions. Undiluted serum was mixed with capture beads (6 types of beads, each of different APC intensities, one for each cytokine, all mixed together) and phycoerythrin (PE) labeled detection reagent. The mixture was incubated for 2 hours at room temperature followed by two washes. Presence of cytokine was then measured by flow cytometric detection of PE intensity. Mean fluorescence intensity was then compared to a standard curve for each cytokine. For each cytokine ANOVA was performed on the soluble, drug combo in AB, drug combo in ABC low, and drug combo in ABC high groups. Then Dunnett's multiple comparison test was performed comparing each drug in copolymer group to the soluble drug group. Resiquimod (R848) Low=1.5 mg/kg; High=3 mg/kg. The Dunnett's comparison test significance values are noted on the graphs with stars:  $P<0.005$; * $P<0.0005$.
Figure 14:
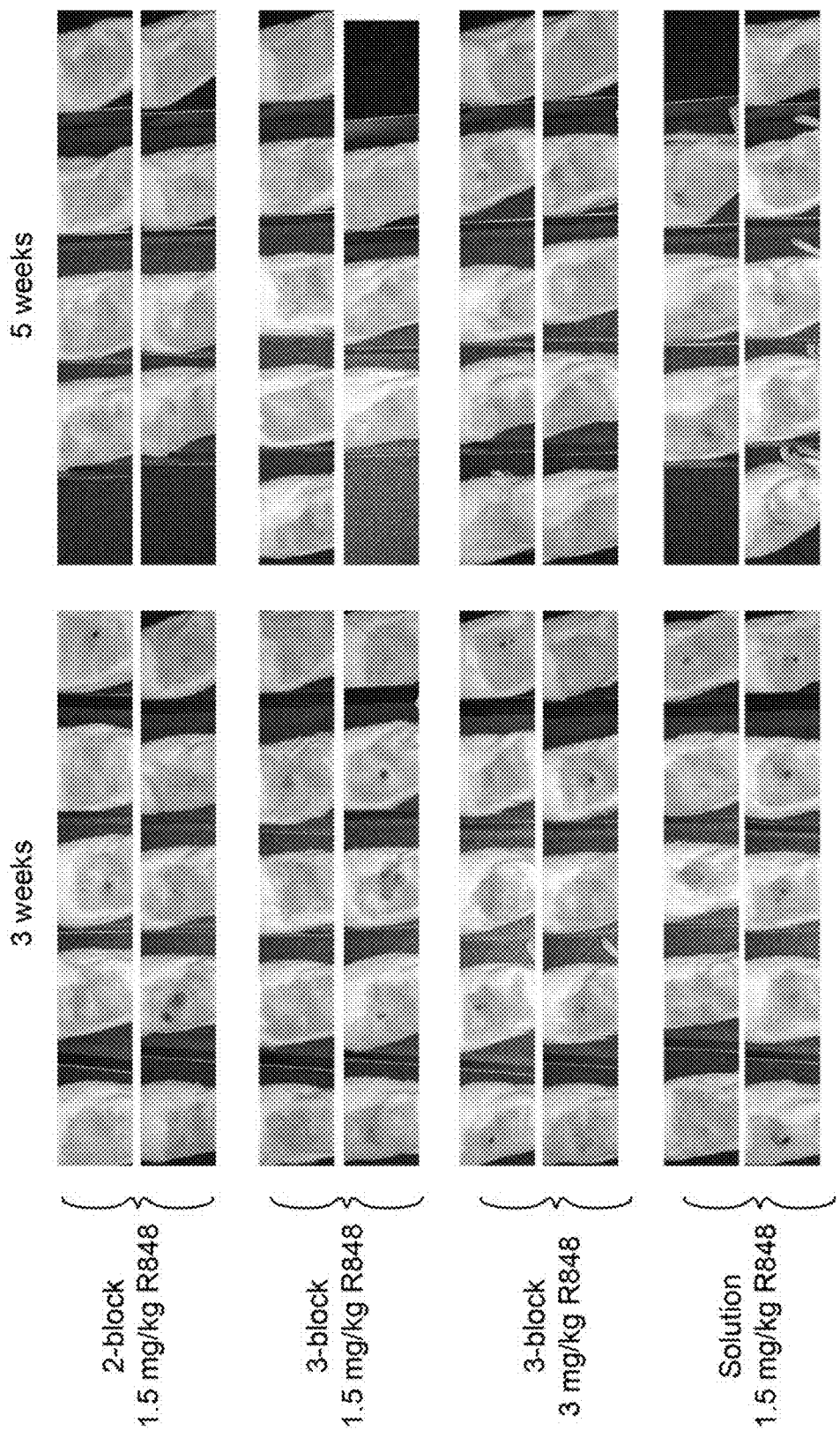
FIG. 14 shows that sustained release reduces local ulceration in mice. AB bottlebrush copolymer=2 block; ABC bottlebrush copolymer=3 block.
Figure 15:
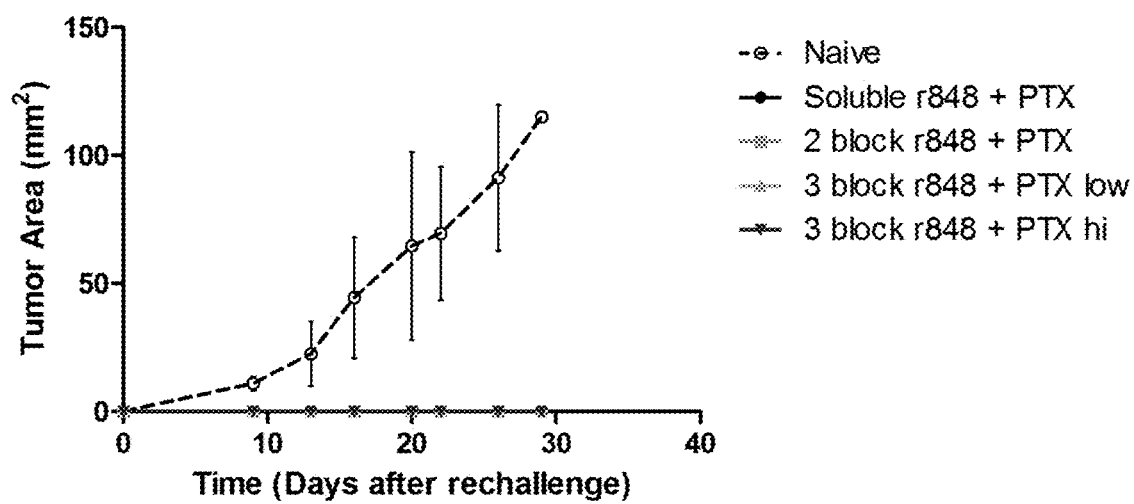
FIG. 15. Cured mice re-challenged with CT-26 (0.1 M inoc.). In order to test whether cured mice had acquired immunity against CT-26 tumor, animals that were completely cured were re-challenged with 0.1 million of CT-26 cells on the other side of at hind flank. A group of naïve mice were also inoculated as a control for CT-26 tumor growth. Resiquimod (R848) Low=1.5 mg/kg; High=3 mg/kg.
Figure 16A:
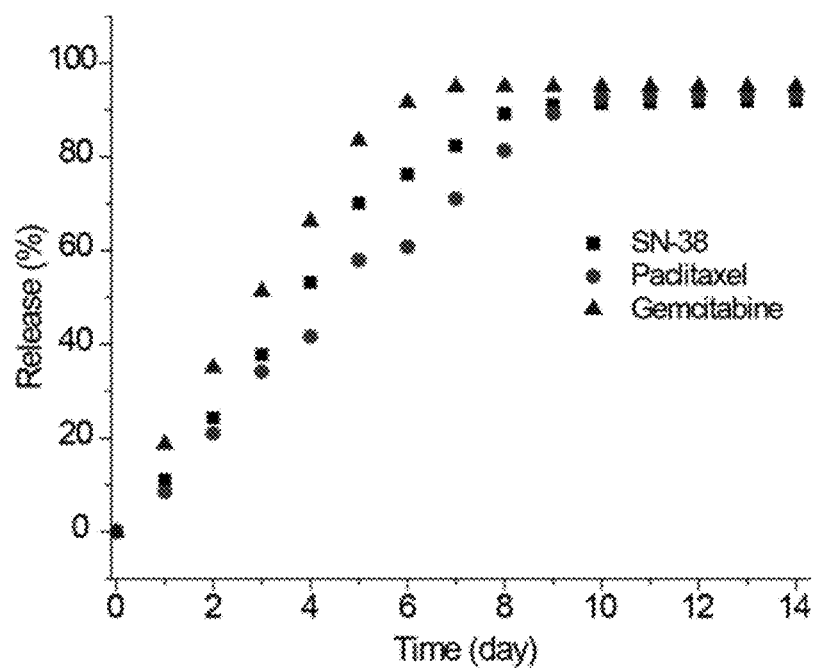
FIGS. 16A-16B. 3-drug combination treatment of A549 tumor (10 M inoc.). A549 cells are human lung adenocarcinoma cells.
Figure 16B:
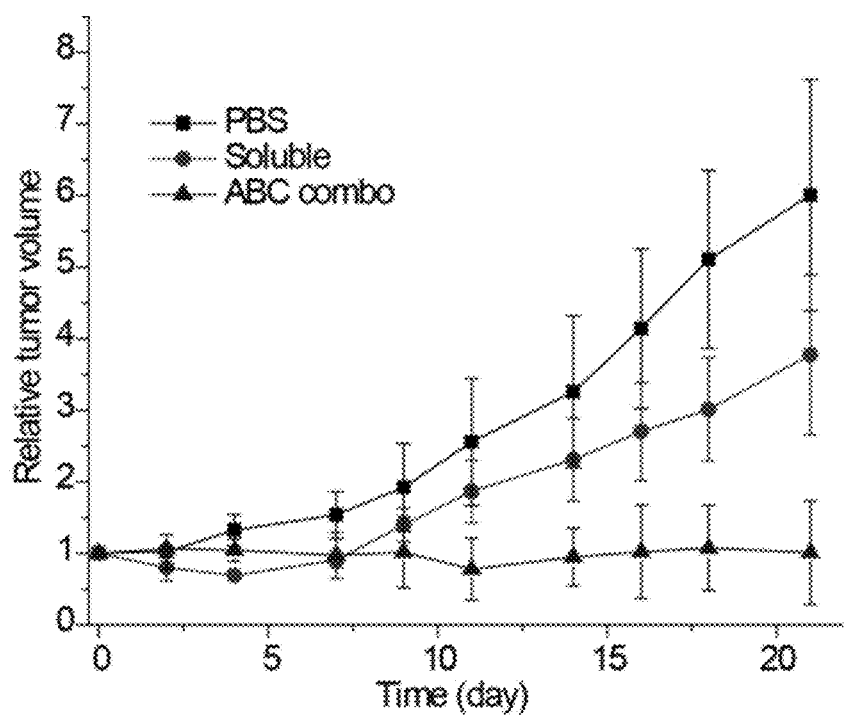

For example, a thermoresponsive three block bottlebrush copolymer (ABC) can serve as a versatile platform for local delivery of anticancer medicines. The ABC is an amphiphilic copolymer that self-assembles into micelles at room temperature enabling solvation of hydrophobic drugs into water and provides straightforward administration using a syringe for direct injection at the tumor site. Efficient loading of three widely used chemotherapeutics is achieved: Paclitaxel, Gemcitabine, and SN-38 (see FIG. 10). The drug-loaded ABC demonstrated rapid gelation when heated to 37° C., and in vitro and in vivo experiments confirmed formation of a local reservoir for sustained release of medicines (see, e.g., FIGS. 19-23). Intratumor injection of combination drug-loaded ABC hydrogel resulted in eradication of A549, human lung cancer cells, in mice (see, e.g., FIGS. 16A-16B). ABC hydrogels were further used in immunochemotherapy, delivering Paclitaxel and Resiquimod, an important immunomodulator, intratumorally to achieve significant inhibition in proliferation of aggressive colon cancer cells, CT-26 (see, e.g., FIGS. 11, 12, 15, 24). Furthermore, systemic and local side effects of immune-modulator use were minimized, corroborating the polymers' ability to provide controlled release of drug molecules. (see, e.g., FIGS. 13, 14).

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein.

It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A triblock copolymer comprising Block A, Block B, and Block C, wherein:
    the triblock copolymer comprises a backbone polymer of repeating units covalently linked to polymeric sidechains;
    Block A, Block B, and Block C of the copolymer comprise the polymeric sidechains covalently linked to the repeating units of the backbone polymer; and
    the polymeric sidechains of Block A, Block B, and Block C are each independently selected from polyethers, polyesters, and polyacrylamides;
    provided that no two of Block A, Block B, and Block C comprise polymeric sidechains of the same polymer type.

2. The copolymer of claim 1, wherein Block A comprises polyester sidechains.

3. The copolymer of claim 2, wherein the polyester sidechains of Block A are polyglycolic acid (PGA), polylactic acid (PLA), poly(lactic-co-glycolic acid) (PLGA), polycaprolactone (PCL), polyhydroxyalkanoate (PHA), polyhydroxybutryate (PHB), polyethylene adipate (PEA), polybutylene succinate (PBS), or poly(3-hydroxybutyrate-co-3-hydroxyvalerate) (PHBV).

4. The copolymer of claim 3, wherein the polyester sidechains of Block A are polylactic acid (PLA).

5. The copolymer of claim 1, wherein Block B comprises polyether sidechains.

6. The copolymer of claim 5, wherein the polyether sidechains of Block B are polyethylene glycol (PEG), polyoxymethylene (POM), polypropylene glycol (PPG), polytetramethylene glycol (PTMG), poly(ethyl ethylene) phosphate (PEEP), or poly(oxazoline).

7. The copolymer of claim 6, wherein the polyether sidechains of Block B are polyethylene glycol (PEG).

8. The copolymer of claim 1, wherein Block C comprises polyacrylamide sidechains.

9. The copolymer of claim 8, wherein the polyacrylamide sidechains are poly(N-isopropylacrylamide) (PNIPAM).

10. The copolymer of claim 1, wherein the copolymer is of Formula (I):

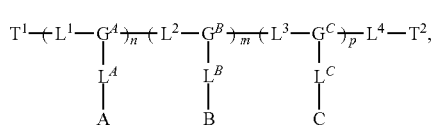
(I)

wherein:
    each of $G^A$, $G^B$, and $G^C$ is independently optionally substituted alkylene, optionally substituted heteroalkylene, optionally substituted carbocyclylene, optionally substituted heterocyclylene, optionally substituted arylene, optionally substituted heteroarylene, or a combination thereof;
    each of $L^1$, $L^2$, $L^3$, and $L^4$ is independently a linker selected from the group consisting of optionally substituted alkylene, optionally substituted heteroalkylene, optionally substituted alkenylene, optionally substituted alkynylene, and combinations thereof;
    each of $L^A$, $L^B$, and $L^C$ is independently a linker selected from the group consisting of optionally substituted alkylene, optionally substituted heteroalkylene, optionally substituted carbocyclylene, optionally substituted heterocyclylene, optionally substituted arylene, optionally substituted heteroarylene, and combinations thereof;
    each of $T^1$ and $T^2$ is independently a terminal group selected from the group consisting of hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted hydroxyl, optionally substituted amino, and optionally substituted thiol;
    A, B, and C are each independently polymers selected from polyethers, polyesters, and polyacrylamides, wherein each of A are the same polymer, each of B are the same polymer, and each of C are the same polymer;
    provided that A, B, and C are different polymer types; and
    each of n, m, and p is independently an integer between 1 and 4000, inclusive.

11. The copolymer of claim 10, wherein each of A, each of B, or each of C is a polyester selected from the group consisting of polyglycolic acid (PGA), polylactic acid (PLA), poly(lactic-co-glycolic acid) (PLGA), polycaprolactone (PCL), polyhydroxyalkanoate (PHA), polyhydroxybutryate (PHB), polyethylene adipate (PEA), polybutylene succinate (PBS), and poly(3-hydroxybutyrate-co-3-hydroxyvalerate) (PHBV).

12. The copolymer of claim 11, wherein the polyester is polylactic acid (PLA).

13. The copolymer of claim 10, wherein each of A, each of B, or each of C is a polyether selected from the group consisting of polyethylene glycol (PEG), polyoxymethylene (POM), polypropylene glycol (PPG), polytetramethylene glycol (PTMG), poly(ethyl ethylene) phosphate (PEEP), and poly(oxazoline).

14. The copolymer of claim 13, wherein the polyether is polyethylene glycol (PEG).

15. The copolymer of claim 10, wherein each of A, each of B, or each of C is poly(N-isopropylacrylamide) (PNIPAM).

16. The copolymer of claim 10, wherein the copolymer is of Formula (I-a):

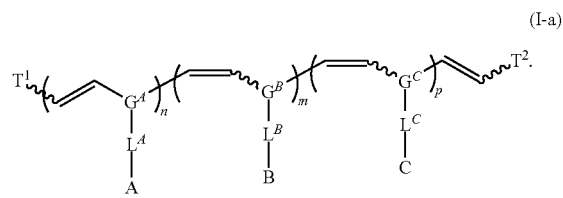
(I-a)

17. The copolymer claim 10, wherein the copolymer is of Formula (I-d):

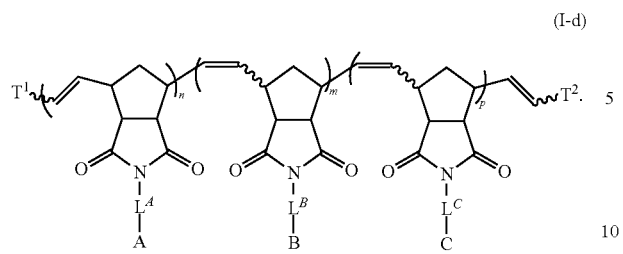

18. The copolymer of claim 10, wherein each A, each B, or each C is a polyester of the following formula:

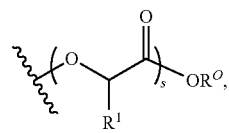

wherein:
R¹ is hydrogen, optionally substituted alkyl, optionally substituted alkenyl, optionally substituted alkynyl, optionally substituted aryl, optionally substituted heteroaryl, optionally substituted carbocyclyl, optionally substituted heterocyclyl, or optionally substituted acyl;
R^O is hydrogen, optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted acyl, or an oxygen protecting group; and
s is an integer between 5 and 2000, inclusive.

19. The copolymer of claim 10, wherein each A, each B, or each C is a polyether of the following formula:

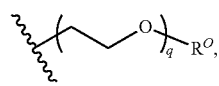

wherein:
R^O is hydrogen, optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted acyl, or an oxygen protecting group; and
q is an integer between 5 and 2000, inclusive.

20. The copolymer of claim 10, wherein each A, each B, or each C is a polyacrylamide group of the following formula:

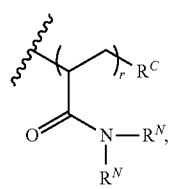

wherein:
each instance of R^N is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two R^N on the same nitrogen atom are taken together with the intervening atoms to form optionally substituted heterocyclyl or optionally substituted heteroaryl;
R^C is hydrogen, halogen, CN, optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted acyl, optionally substituted amino, optionally substituted hydroxyl, or optionally substituted thiol; and
r is an integer between 5 and 2000, inclusive.

21. The copolymer of claim 10, wherein each A is a polyester, each B is a polyether, and each C is a polyacrylamide.

22. The copolymer of claim 21, wherein:
each A is selected from the group consisting of polyglycolic acid (PGA), polylactic acid (PLA), poly(lactic-co-glycolic acid) (PLGA), polycaprolactone (PCL), polyhydroxyalkanoate (PHA), polyhydroxybutryate (PHB), polyethylene adipate (PEA), polybutylene succinate (PBS), and poly(3-hydroxybutyrate-co-3-hydroxyvalerate) (PHBV);
each B is selected from the group consisting of polyethylene glycol (PEG), polyoxymethylene (POM), polypropylene glycol (PPG), polytetramethylene glycol (PTMG), poly(ethyl ethylene) phosphate (PEEP), and poly(oxazoline); and
each C is poly(N-isopropylacrylamide) (PNIPAM).

23. The copolymer of claim 10, wherein each A is polylactic acid (PLA), each B is polyethylene glycol (PEG), and each C is poly(N-isopropylacrylamide) (PNIPAM).

24. The copolymer of claim 10, wherein at least one of A, B, and C is a polymer that exhibits lower critical solution temperature (LCST) behavior.

25. A particle comprising a copolymer of claim 1.

26. The particle of claim 25, wherein the particle is formed via self-assembly of the copolymer.

27. The particle of claim 25, wherein the particle has a diameter from 1 nm to 500 nm, inclusive.

28. The particle of claim 25, wherein the particle has a diameter from 70 nm to 130 nm, inclusive.

29. A hydrogel comprising a copolymer of claim 1.

30. The hydrogel of claim 29, wherein the hydrogel is thermally-responsive.

31. The hydrogel of claim 29, wherein the hydrogel gels at a temperature from 30-40° C., inclusive.

32. The hydrogel of claim 29, wherein the hydrogel gels at physiological temperature.

33. A formulation comprising a copolymer of claim 1, one or more therapeutic agents, and optionally a carrier or excipient.

34. The formulation of claim 33, wherein at least one therapeutic agent is a non-steroidal anti-inflammatory drug (NSAID).

35. The formulation of claim 33, wherein at least one therapeutic agent is a steroid.

36. The formulation of claim 33, wherein at least one therapeutic agent is an antibiotic.

37. The formulation of claim 33, wherein the formulation comprises a non-steroidal anti-inflammatory drug (NSAID), a steroid, and an antibiotic.

38. The formulation of claim 37, wherein the formulation comprises ibuprofen, dexamethasone, and ofloxacin.

39. The formulation of claim 33, wherein the formulation comprises one or more anti-proliferative or anti-cancer agents.

40. The formulation of claim 33, wherein the formulation provides extended release of the one or more therapeutic agents.

41. A method of preparing a copolymer of claim 1, the method comprising forming the copolymer via polymerization reactions.

42. The method of claim 41, comprising the steps of:
(a) providing a first macromonomer comprising a first polymer and one or more reactive moieties;
(b) providing a second macromonomer comprising a second polymer and one or more reactive moieties;
(c) providing a third macromonomer comprising a third polymer and one or more reactive moieties;
(d) reacting the macromonomer provided in step (a) under conditions suitable to effect a polymerization reaction and yield a homopolymer;
(e) reacting the homopolymer formed in step (d) with the macromonomer provided in step (b) under conditions suitable to effect a polymerization reaction and yield a diblock copolymer;
(f) reacting the diblock copolymer formed in step (e) with the macromonomer provided in step (c) under conditions suitable to effect a polymerization reaction and yield the triblock copolymer.

43. The method of claim 42, wherein the polymerization reactions are ring-opening metathesis polymerization (ROMP).

44. The copolymer of claim 1, wherein at least one of Block A, Block B, and Block C comprises polymeric sidechains that exhibit lower critical solution temperature (LCST) behavior.

45. The copolymer of claim 1, wherein the repeating backbone units of Block A, Block B, and Block C are the same repeating units.

46. The copolymer of claim 1, wherein the polyester sidechains are polylactic acid (PLA); the polyether sidechains are polyethylene glycol (PEG); and the polyacrylamide sidechains of are poly(N-isopropylacrylamide) (PNIPAM).

47. The copolymer of claim 1, wherein Block A comprises polyester sidechains; Block B comprises polyether sidechains; and Block C comprises polyacrylamide sidechains.

48. The copolymer of claim 47, wherein:
Block A comprises polyester sidechains selected from the group consisting of polyglycolic acid (PGA), polylactic acid (PLA), poly(lactic-co-glycolic acid) (PLGA), polycaprolactone (PCL), polyhydroxyalkanoate (PHA), polyhydroxybutryate (PHB), polyethylene adipate (PEA), polybutylene succinate (PBS), and poly(3-hydroxybutyrate-co-3-hydroxyvalerate) (PHBV);
Block B comprises polyether sidechains selected from the group consisting of polyethylene glycol (PEG), polyoxymethylene (POM), polypropylene glycol (PPG), polytetramethylene glycol (PTMG), poly(ethyl ethylene) phosphate (PEEP), and poly(oxazoline); and
Block C comprises polyacrylamide sidechains, wherein the polyacrylamide sidechains are poly(N-isopropylacrylamide) (PNIPAM).

49. The copolymer of claim 48, wherein the polyester sidechains of Block A are polylactic acid (PLA); the polyether sidechains of Block B are polyethylene glycol (PEG); and the polyacrylamide sidechains of Block C are poly(N-isopropylacrylamide) (PNIPAM).

50. The copolymer of claim 1, wherein the ratio of polyester to polyether to polyacrylamide is (5 to 15):(30 to 50):(5 to 15).

51. The copolymer of claim 1, wherein the ratio of polyester to polyether to polyacrylamide is about 10:40:10.

* * * * *